United States Patent
Gentles et al.

(10) Patent No.: US 7,521,441 B2
(45) Date of Patent: *Apr. 21, 2009

(54) CYCLOPROPYL FUSED INDOLOBENZAZEPINE HCV NS5B INHIBITORS

(75) Inventors: Robert G. Gentles, Wallingford, CT (US); Piyasena Hewawasam, Middletown, CT (US); Min Ding, Glastonbury, CT (US); Carl P. Bergstrom, Madison, CT (US); Scott W. Martin, Middletown, CT (US); Kap-Sun Yeung, Madison, CT (US); Thomas W. Hudyma, Durham, CT (US); Xiaofan Zheng, Cheshire, CT (US); John A. Bender, Middletown, CT (US); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/745,090

(22) Filed: May 7, 2007

(65) Prior Publication Data

US 2007/0270406 A1 Nov. 22, 2007

Related U.S. Application Data

(60) Provisional application No. 60/894,253, filed on Mar. 12, 2007, provisional application No. 60/802,368, filed on May 22, 2006.

(51) Int. Cl.
*A61P 31/00* (2006.01)
*A61K 31/407* (2006.01)
*C07D 487/00* (2006.01)

(52) U.S. Cl. .............................. 514/214.01; 540/576

(58) Field of Classification Search ............ 514/214.01; 540/576

See application file for complete search history.

(56) References Cited

U.S. PATENT DOCUMENTS

| 7,153,848 B2 | 12/2006 | Hudyma et al. ......... 514/214.01 |
| 2006/0166964 A1 | 7/2006 | Hudyma et al. ......... 514/211.09 |
| 2007/0060565 A1 | 3/2007 | Meanwell et al. ....... 514/214.01 |
| 2007/0078122 A1 | 4/2007 | Bergstrom et al. ...... 514/214.01 |
| 2007/0185083 A1 | 8/2007 | Bergstrom et al. ...... 514/214.01 |

FOREIGN PATENT DOCUMENTS

| WO | WO2005/080399 | 9/2005 |
| WO | WO2006/040039 | 4/2006 |
| WO | WO2006/046030 | 5/2006 |
| WO | WO2007/029029 | 3/2007 |

OTHER PUBLICATIONS

U.S. Appl. No. 11/752,354, filed May 23, 2007, Robert G. Gentles, et al.
U.S. Appl. No. 11/753,137, filed May 24, 2007, Carl P. Bergstrom.
U.S. Appl. No. 11/756,203, filed May 31, 2007, Kap-Sun Yeung, et al.

*Primary Examiner*—Brenda L Coleman
(74) *Attorney, Agent, or Firm*—James Epperson

(57) ABSTRACT

The invention encompasses compounds of formula I as well as compositions and methods of using the compounds. The compounds have activity against hepatitis C virus (HCV) and are useful in treating those infected with HCV.

12 Claims, No Drawings

CYCLOPROPYL FUSED INDOLOBENZAZEPINE HCV NS5B INHIBITORS

CROSS REFERENCE TO RELATED APPLICATIONS

This application claims the benefit of U.S. Provisional Application Ser. No. 60/802,368, filed May 22, 2006, and 60/894,253, filed Mar. 12, 2007.

BACKGROUND OF THE INVENTION

Hepatitis C virus (HCV) is a major human pathogen, infecting an estimated 170 million persons worldwide— roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

DESCRIPTION OF THE INVENTION

One aspect of the invention is a compound of formula I

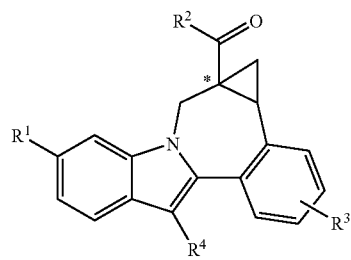

where:
$R^1$ is $CO_2R^5$ or $CONR^6R^7$;
$R^2$ is piperidinyl or piperazinyl and is substituted with 3 substituents selected from the group consisting of alkyl, haloalkyl, alkoxyalkyl, (phenyl)alkyl, alkylCO, haloalkylCO, alkoxyCO, (amino)CO, (alkylamino)CO, and (dialkylamino)CO;
$R^3$ is hydrogen, halo, alkyl, alkenyl, hydroxy, benzyloxy, or alkoxy;
$R^4$ is cycloalkyl;
$R^5$ is hydrogen or alkyl;
$R^6$ is hydrogen, alkyl, alkylSO$_2$, cycloalkylSO$_2$, haloalkylSO$_2$, $(R^7)(R^8)NSO_2$, or $(R^9)SO_2$;
$R^7$ is hydrogen or alkyl;
$R^8$ is hydrogen or alkyl;
$R^9$ is azetidinyl, pyrrolidinyl, piperidinyl, N—($R^{10}$)piperazinyl, morpholinyl, thiomorpholinyl, homopiperidinyl, or homomorpholinyl;
$R^{10}$ is hydrogen or alkyl; and
the carbon bearing the asterisk is of the (R) configuration or the (S) configuration;
or a pharmaceutically acceptable salt thereof.

Another aspect of the invention is a compound of formula I where $R^1$ is $CONHR^6$ and $R^6$ is alkylSO$_2$, cycloalkylSO$_2$, haloalkylSO$_2$, $(R^7)(R^8)NSO_2$, or $(R^9)SO_2$.

Another aspect of the invention is a compound of formula I where $R^2$ is

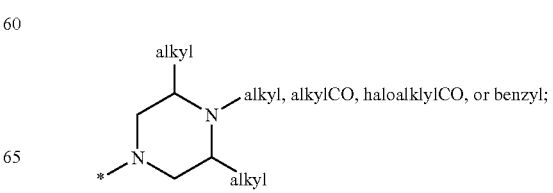

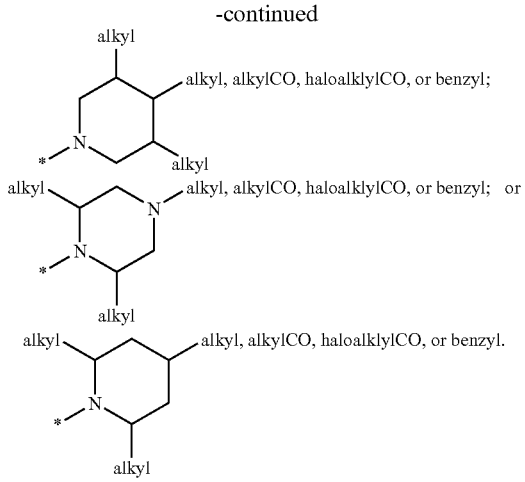

Another aspect of the invention is a compound of formula I where $R^3$ is hydrogen.

Another aspect of the invention is a compound of formula I where $R^3$ is methoxy.

Another aspect of the invention is a compound of formula I where $R^4$ is cyclohexyl.

Another aspect of the invention is a compound of formula I where $R^6$ is alkylSO$_2$, $(R^7)(R^8)$NSO$_2$, or $(R^9)$SO$_2$.

Another aspect of the invention is a compound of formula I where $R^6$ is (dimethylamino)SO$_2$.

Another aspect of the invention is a compound of formula I where $R^6$ is alkylSO$_2$.

Another aspect of the invention is a compound of formula I where $R^6$ is isopropylSO$_2$.

Another aspect of the invention is a compound of formula I where the carbon bearing the asterisk is of the (R) configuration.

Another aspect of the invention is a compound of formula I where the carbon bearing the asterisk is of the (S) configuration.

Any scope of any variable, including $R^1$, $R^2$, $R^3$, $R^4$, $R^5$, $R^6$, $R^7$, $R^8$, $R^9$, $R^{10}$, and the asterisk can be used independently with the scope of any other variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (for example, the structures below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods known in the art.

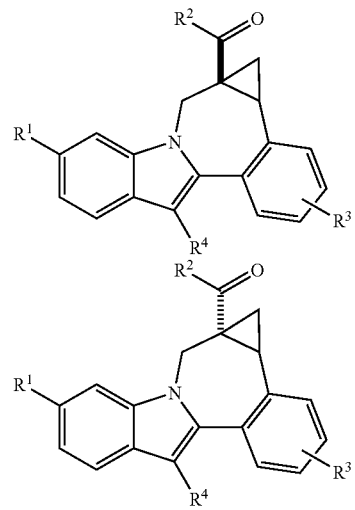

Synthetic Methods

The compounds may be made by methods known in the art including those described below. Some reagents and intermediates are known in the art. Other reagents and intermediates can be made by methods known in the art using readily available materials. The variables (e.g. numbered "R" substituents) used to describe the synthesis of the compounds are intended only to illustrate how to make and are not to be confused with variables used in the claims or in other sections of the specification. Abbreviations used within the schemes generally follow conventions used in the art.

Methyl 2-bromo-3-cyclohexyl-1H-indole-6-carboxylate can be hydrolyzed to 2-bromo-3-cyclohexyl-1H-indole-6-carboxylic acid (See Scheme 1). This compound can be condensed with a variety of sulfonyl ureas, using for example, 1,1'-carbonyldiimidazole in combination with 1,8-diazabicyclo[5.4.0]undec-7-ene in anhydrous THF. The resultant acyl sulfamides can be subjected to known coupling reactions with a diversity of 2-formyl boronic acids or esters, using for example, Suzuki coupling conditions, to provide cyclic hemiaminal intermediates of the type depicted. These compounds can be converted to indolobenzazepine derivatives by treatment with methyl 2-(dimethoxyphosphoryl)acrylate under the influence of cesium carbonate in DMF via consecutive Michael and Horner Emmons reactions.

Related fused cyclopropyl ester derivatives can be generated by methods known in the art, including treatment of the indolobenzazepine esters with trimethyl sulfoxonium iodide under strongly basic conditions in DMSO. The residual aliphatic ester moiety in the resultant fused cyclopropanes can be hydrolyzed and the product acids can be condensed with a variety of trisubstituted piperazines, using for example, O-(1H-benzotriazol-1-yl)-N,N,N',N'-tetramethyluronium tetrafluoroborate and diisopropyl ethyl amine in DMSO.

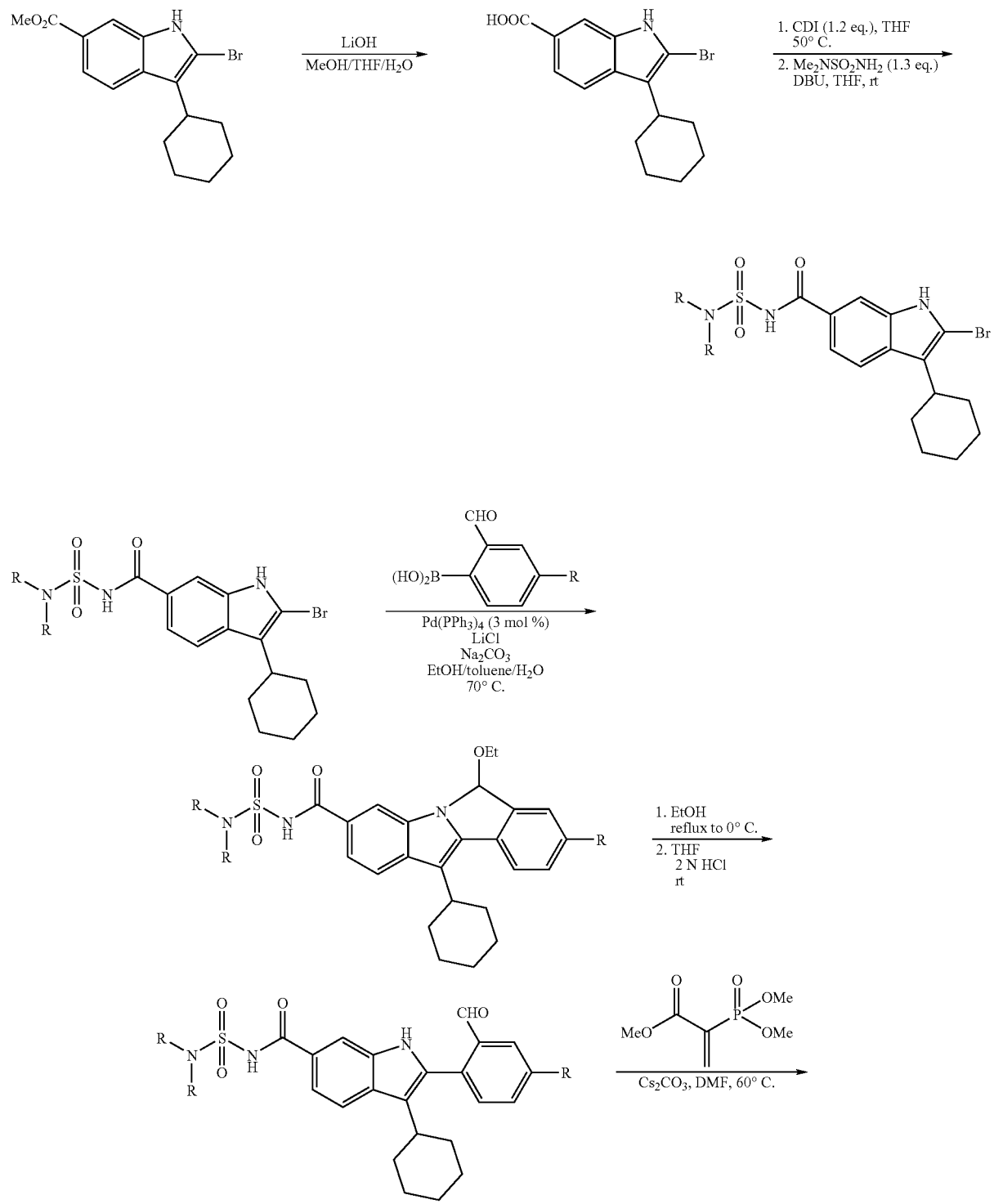

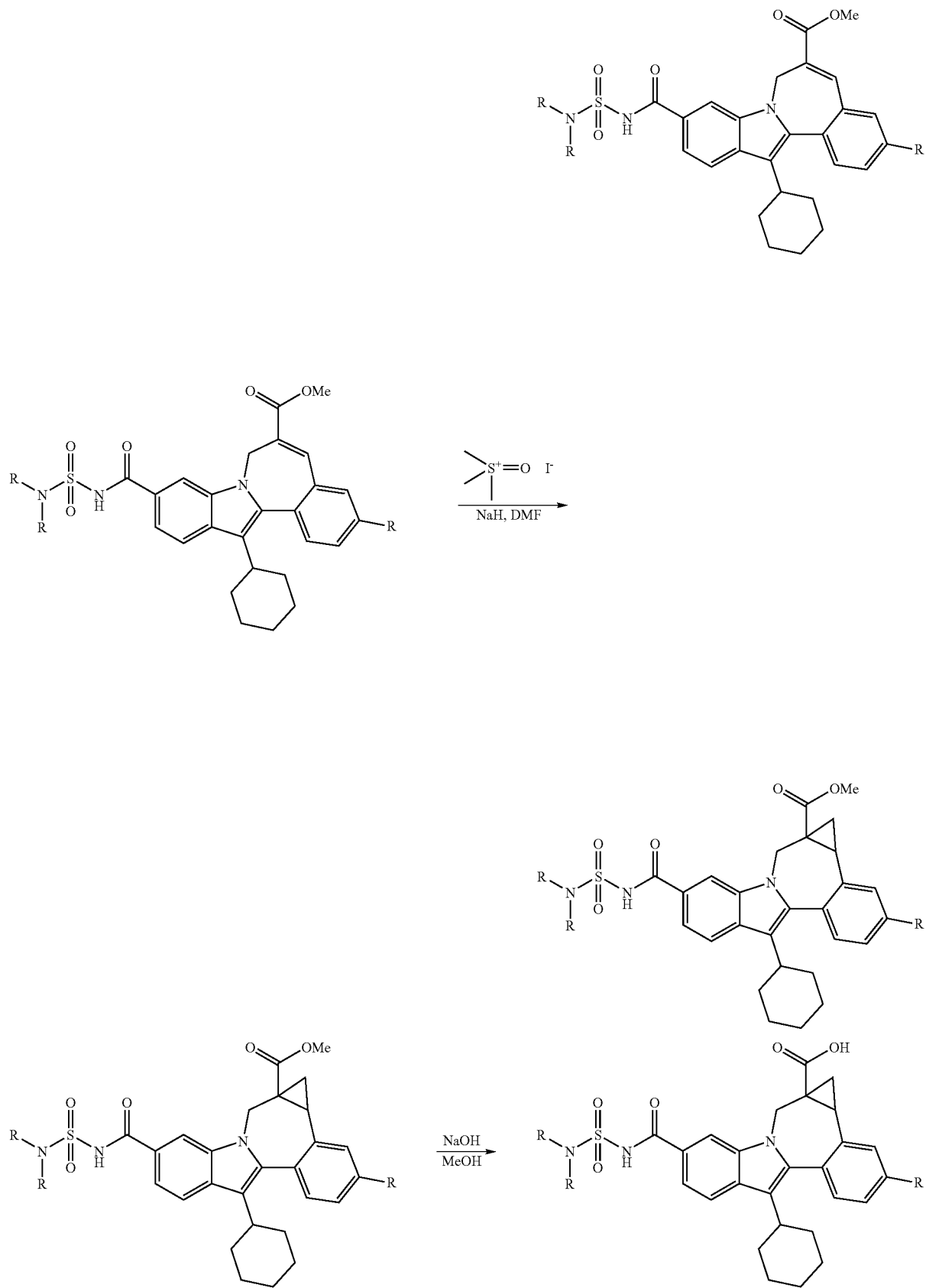

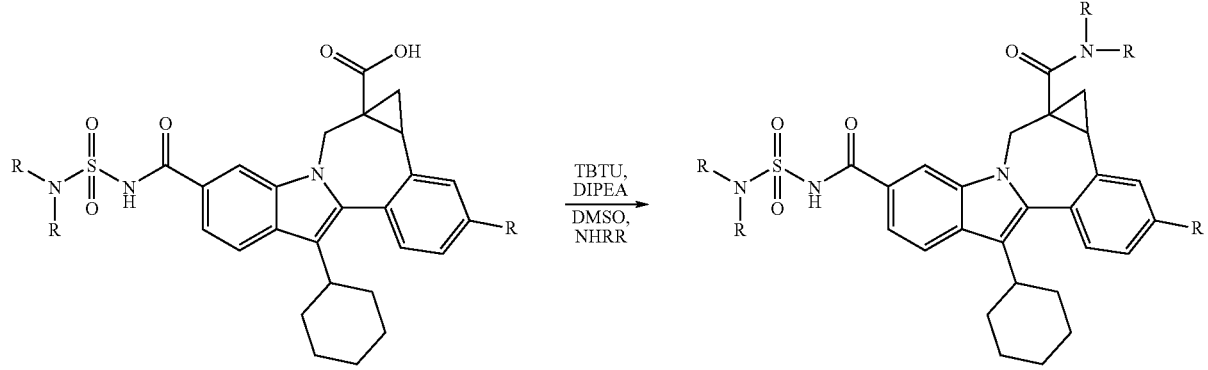
An intermediate useful for the synthesis of some compounds of the invention involves the preparation of the tert-butyl ester indolobenzazepine shown in Scheme 2.
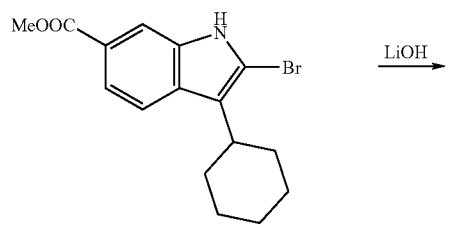
-continued
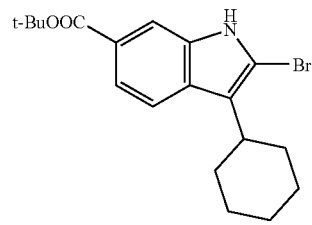
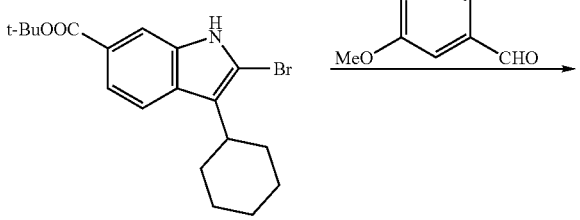
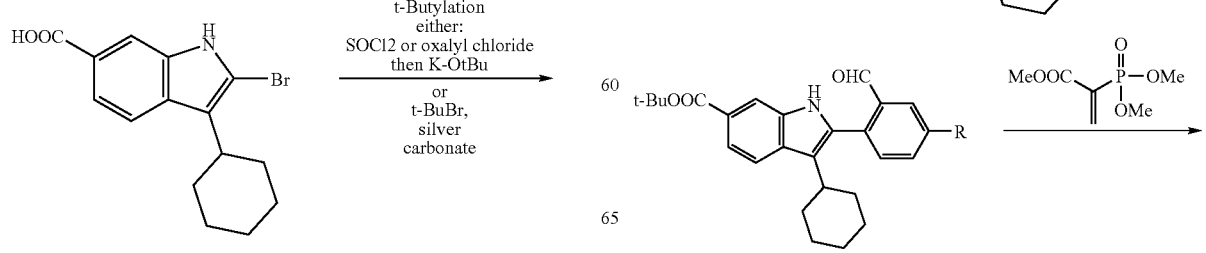

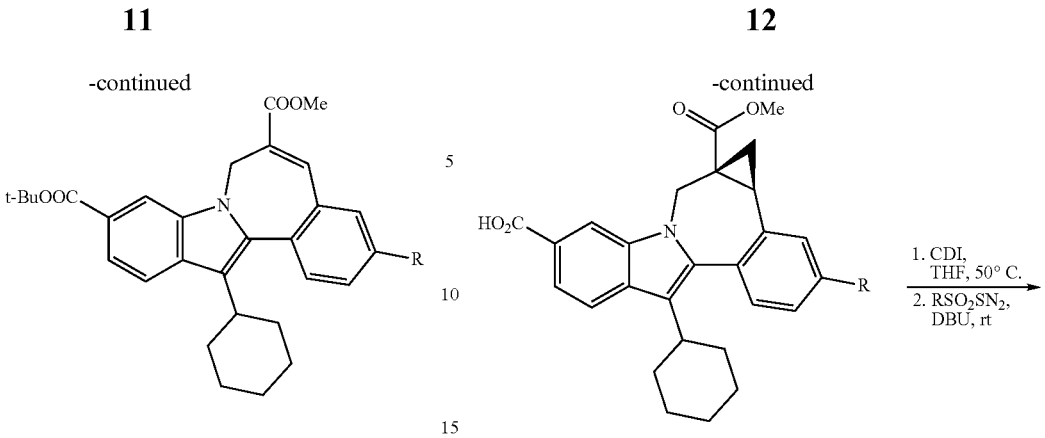

This methodology involves base catalyzed hydrolysis of the indole methyl ester shown, followed by its reaction with either; thionyl chloride and potassium tertiary butoxide, or alkylation with silver carbonate and tertiary butyl bromides. The resultant compound can be transformed using chemistry analogous to that outlined previously to provide the mixed ester indolobenzazepines shown above.

Some examples exist as stereoisomeric mixtures. The invention encompasses all stereoisomers of the compounds. Methods of fractionating stereoisomeric mixtures are well known in the art, and include but are not limited to; preparative chiral supercritical fluid chromatography (SFC) and chiral high performance liquid chromatography (HPLC). An example using this approach is shown in scheme 3.

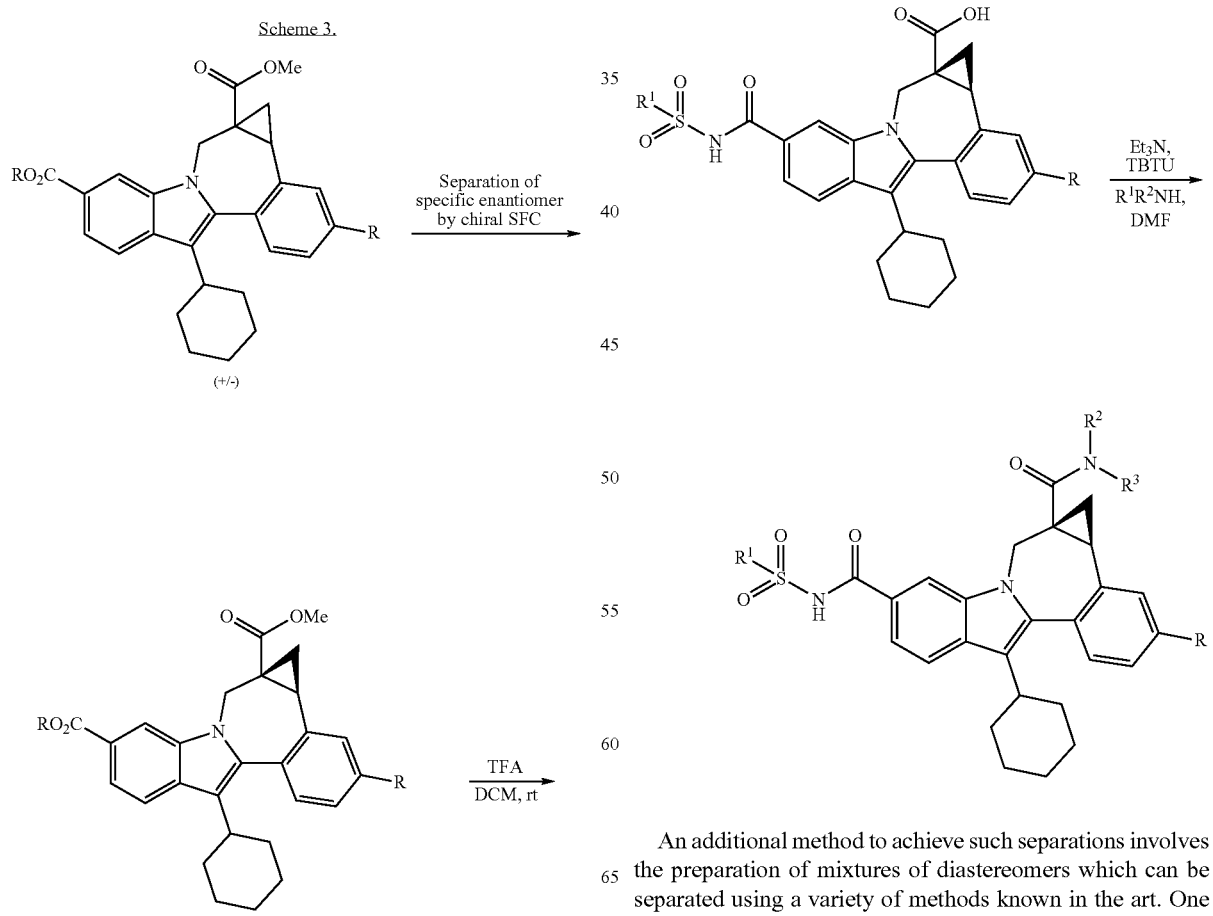

An additional method to achieve such separations involves the preparation of mixtures of diastereomers which can be separated using a variety of methods known in the art. One example of this approach is shown below (Scheme 4).

Scheme 4.
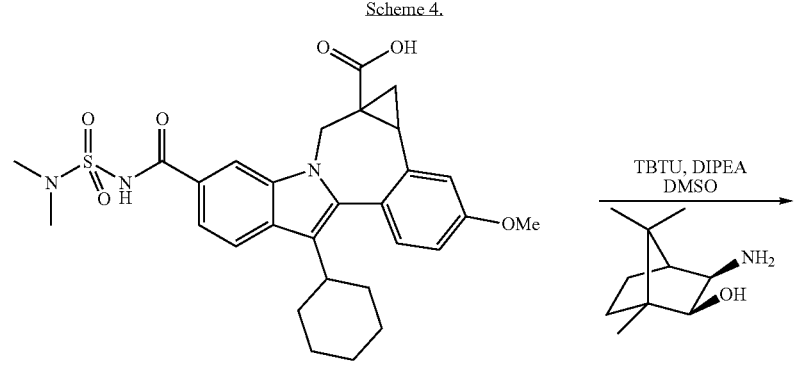
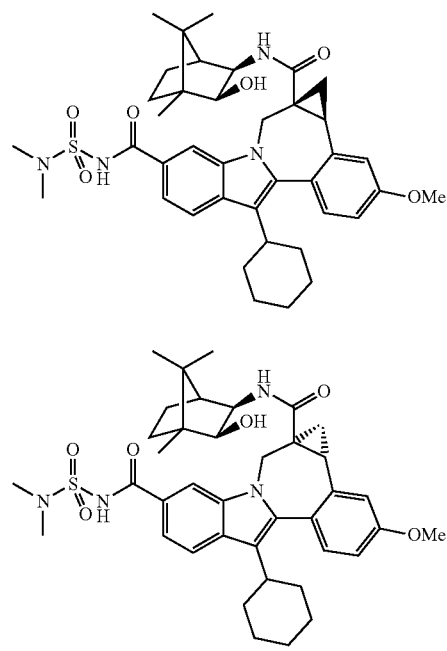
Diastereomers separated by reverse phase HPLC

Some diasteromeric amides can be separated using reverse phase HPLC. After hydrolysis, the resultant optically active acids can be coupled with tri-substituted piperazine derivatives (Scheme 5). For example, O-(1H-benzotriazol-1-yl)-N,N,N',N'-tetramethyluronium tetrafluoroborate and diisopropyl ethyl amine in DMSO can be used to give trisubstituted piperazine carboxamides. Other standard acid amine coupling methods can also be used to give optically active carboxamides.

Scheme 5.

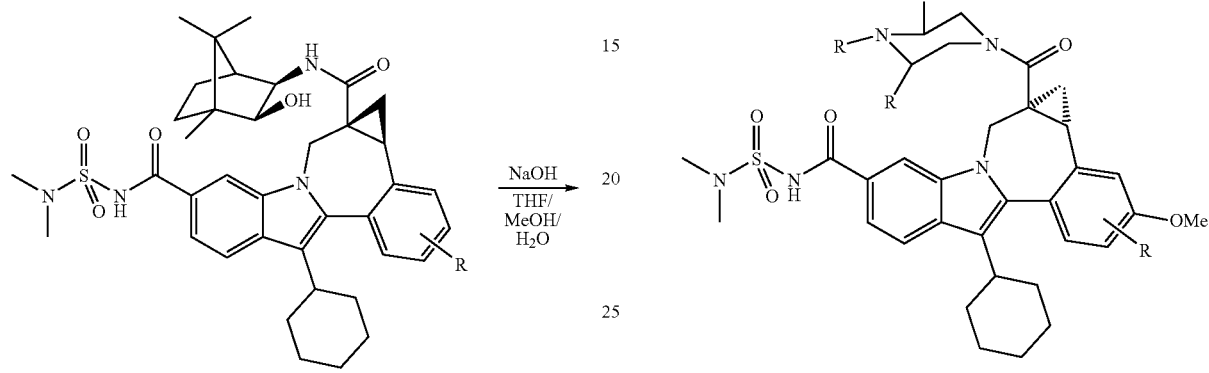

N-protected piperazines can also be coupled to the intermediate indolobenzazepine acids and the resultant piperazine carboxamides can be deprotected using methods known in the art and derivatized using a variety of synthetic protocols, some illustrative examples of which are shown below, (Scheme 6).

Scheme 6.

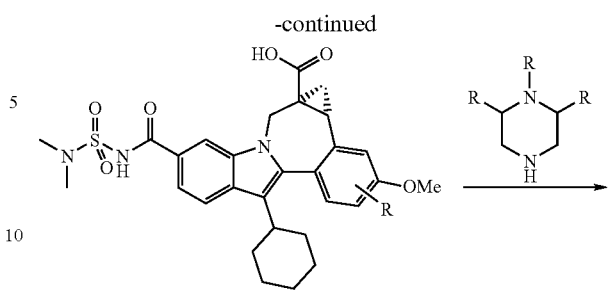

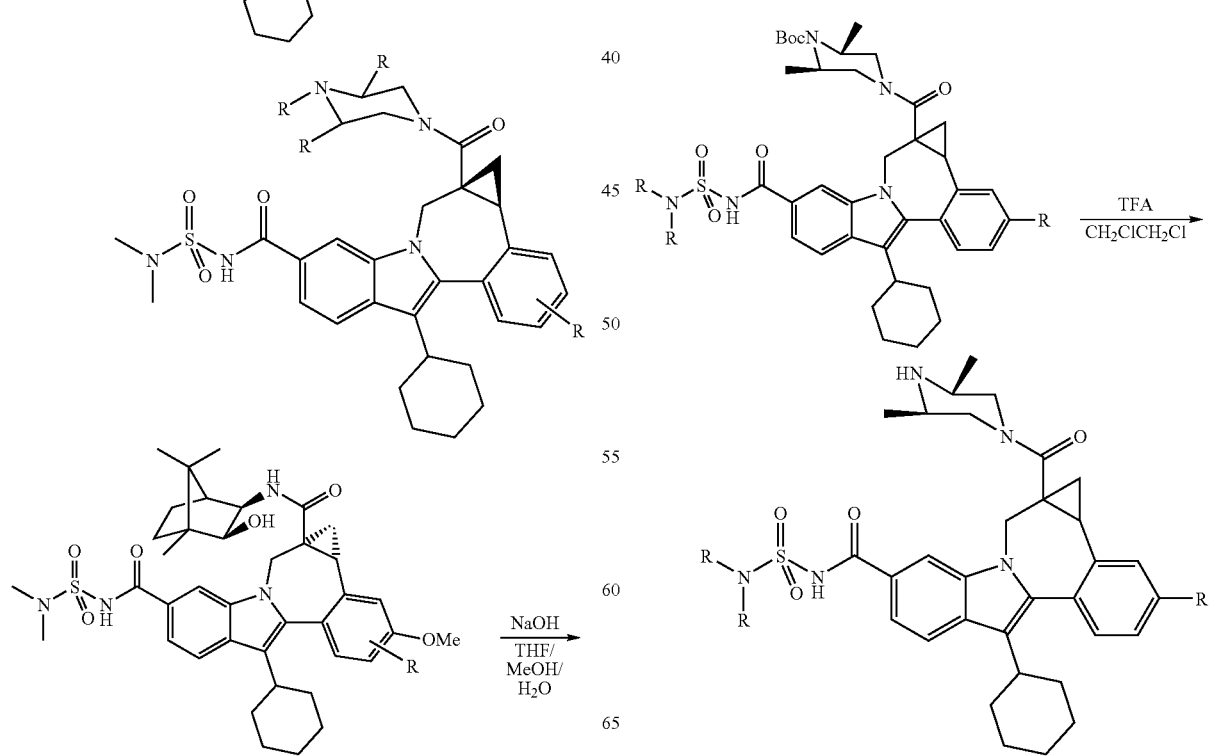

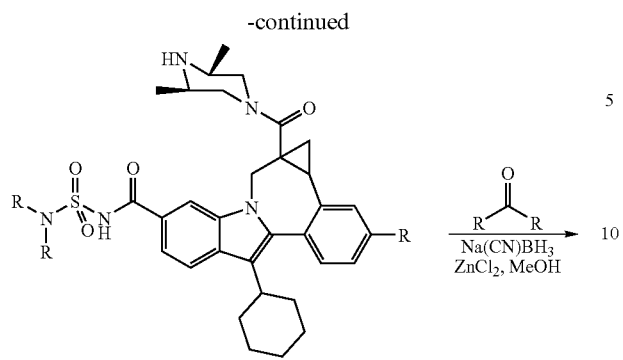

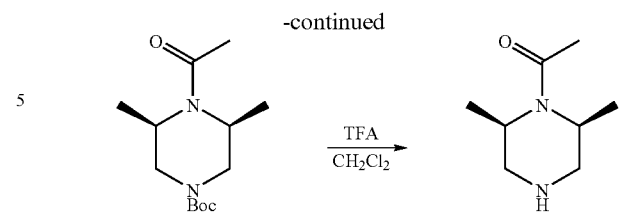

Certain disubstituted piperazines can be coupled directly to a cyclopropyl fused indolobenzazepine acid and can be subsequently derivatized to provide further examples using a variety of methods, one example of which is shown in Scheme 8.

Additionally, tri-substituted piperazine amines can be prepared prior to coupling to the indolobenzazepine cores using methodology known in the art, some examples of which are provided in scheme 7.

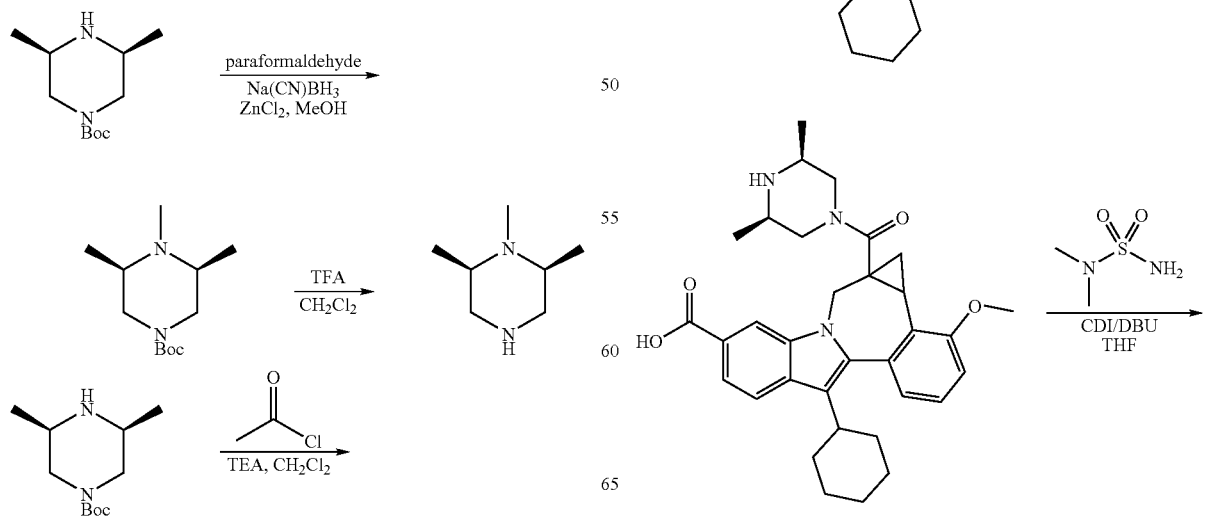

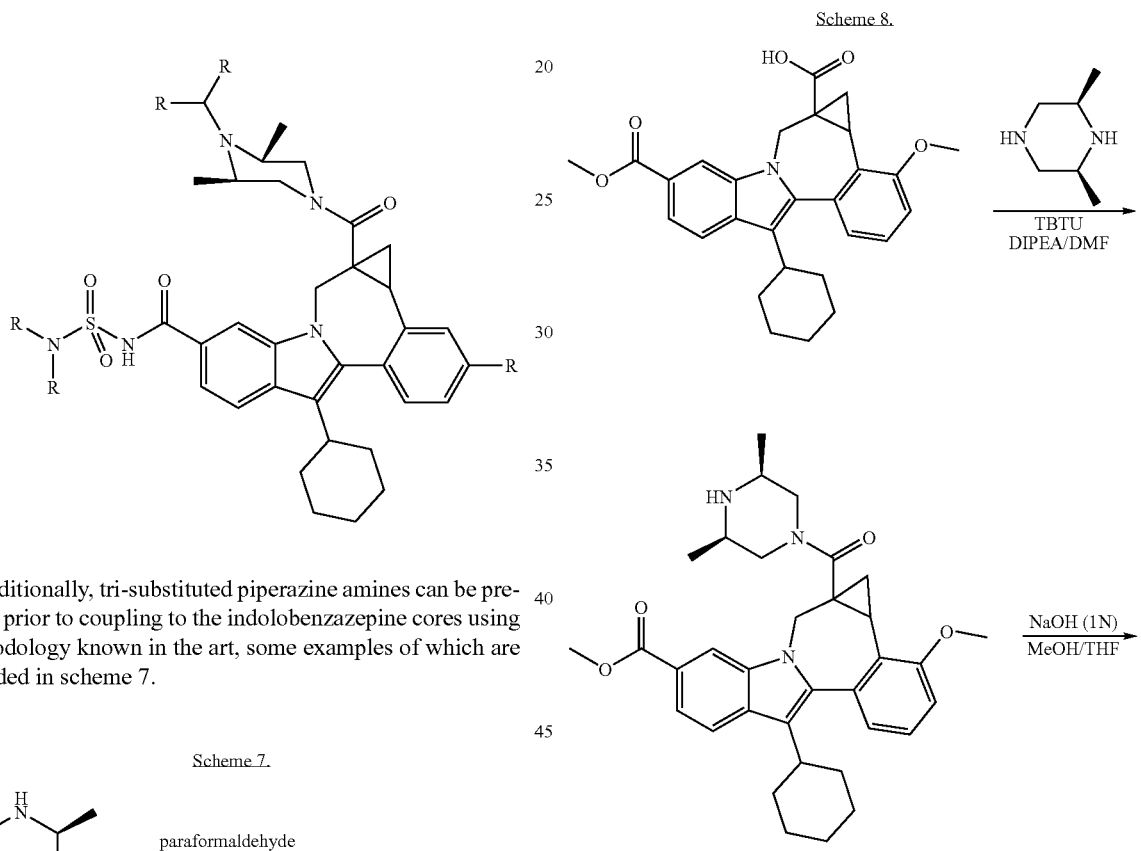

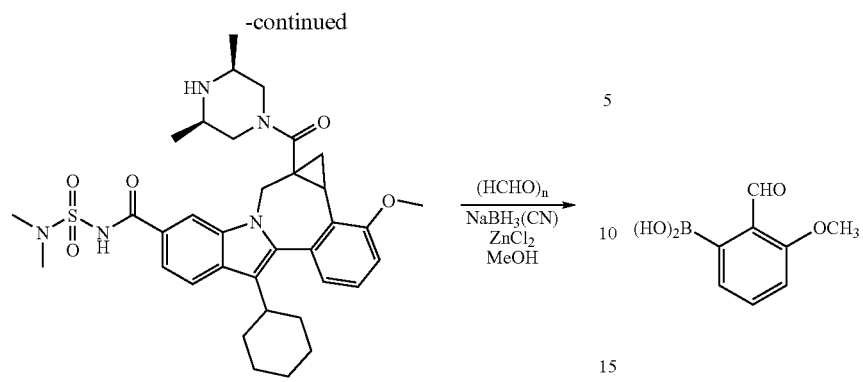

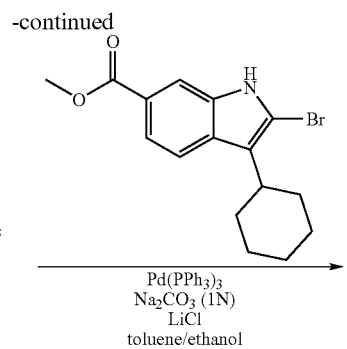

Alternative methodology that can be used for the preparation of intermediates useful for the synthesis of additional examples is shown in Scheme 9. Disubstituted aryl boronic acids can be prepared by methods known in the art, an example of which is directed lithiation of a suitable aryl precursor, and quenching the intermediate organolithium with triisopropyl borate. After hydrolysis, the resultant boronic acid can be coupled with suitably derivatized 2-bromo indoles, using for example, Suzuki coupling conditions. The product indoles can be further transformed to provide still other examples using methodology related to that shown previously in Scheme 1.

Scheme 9.

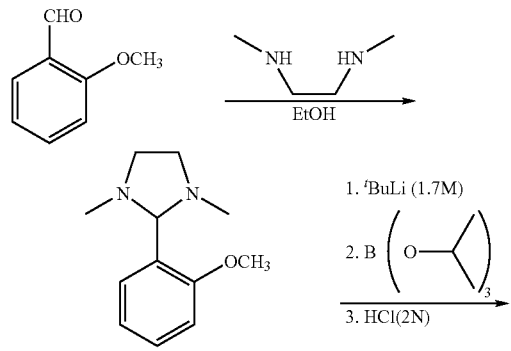

An additional intermediate useful for the synthesis of further examples is shown in Scheme 10. The t-butylester 2-bromoindole can be coupled under Suzuki conditions to (4-Benzyloxy-2-formyl)phenylboronic acid to provide the 2-arylated indole derivative shown. This can be can be converted to the related indolobenzazepine derivative by treatment with methyl 2-(dimethoxyphosphoryl)acrylate under the influence of cesium carbonate in DMF via consecutive Michael and Homer Emmons reactions. The resultant product can then be cyclopropanated using conditions know in the art, including treatment of the indolobenzazepine esters with trimethyl sulfoxonium iodide under strongly basic conditions in DMSO. Subsequent selective cleavage of the t-butyl ester moiety can then be achieved using, for example, treatment with trifluoroacetic acid in 1,2-dichloroethane, and the product acid can be condensed with N,N-dimethylsulfamide using for example, 1,1'-carbonyldiimidazole in combination with 1,8-diazabicyclo[5.4.0]undec-7-ene in anhydrous THF. The residual ester functionality can then be cleaved, using for example, tertiarybutylammonium hydroxide in a mixture of methanol and THF to provide the indolobenzazepine acid shown. This intermediate can then be coupled to a variety of trisubstituted piperazines using methods know in the art to provide further examples.

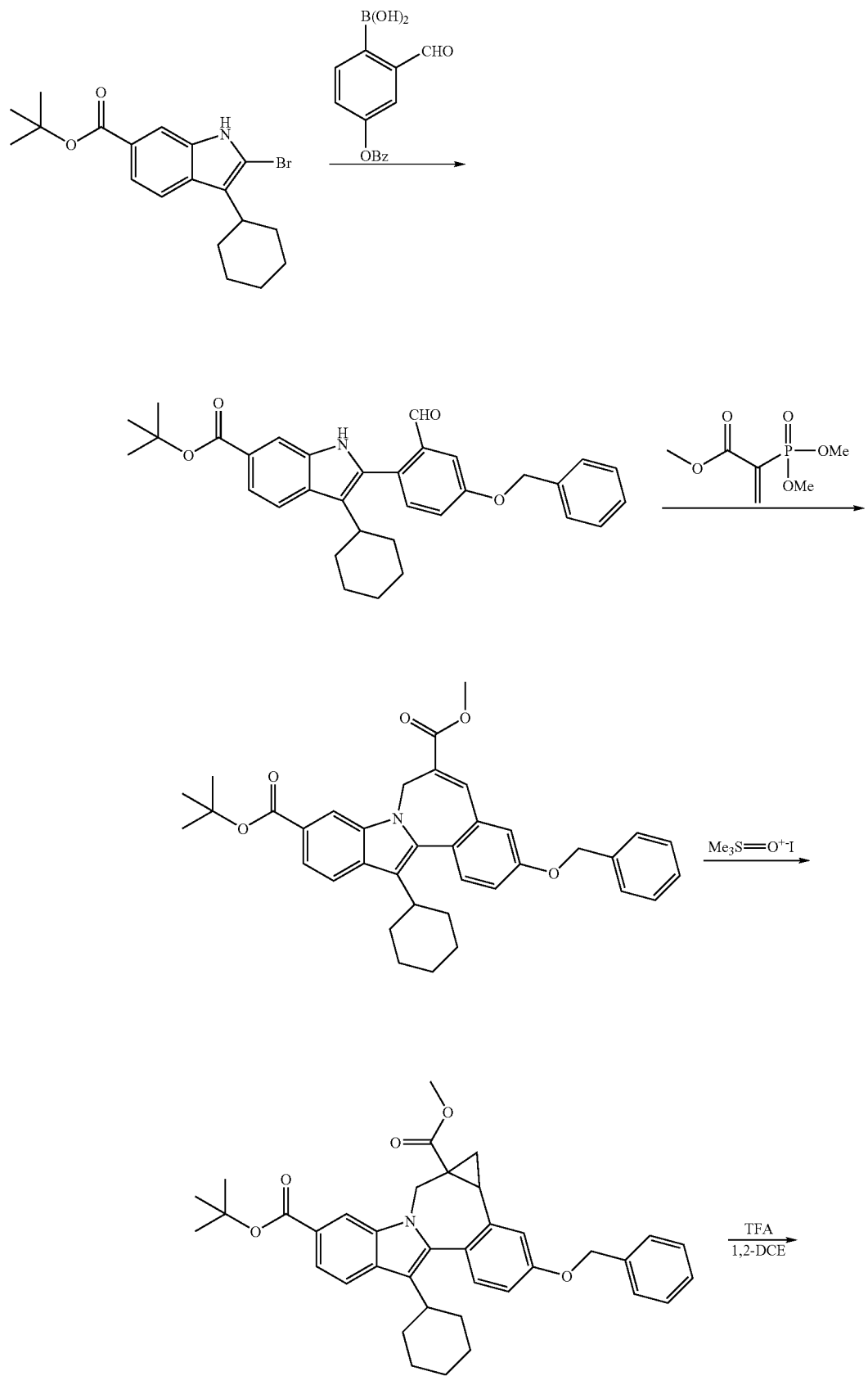
Scheme 10.

-continued
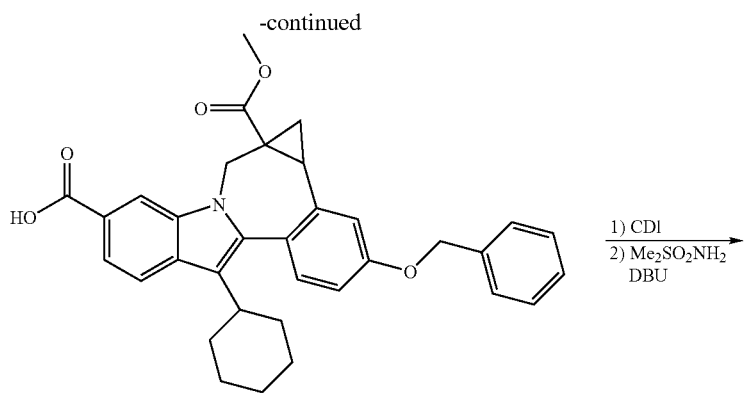
1) CDI
2) Me$_2$SO$_2$NH$_2$
DBU
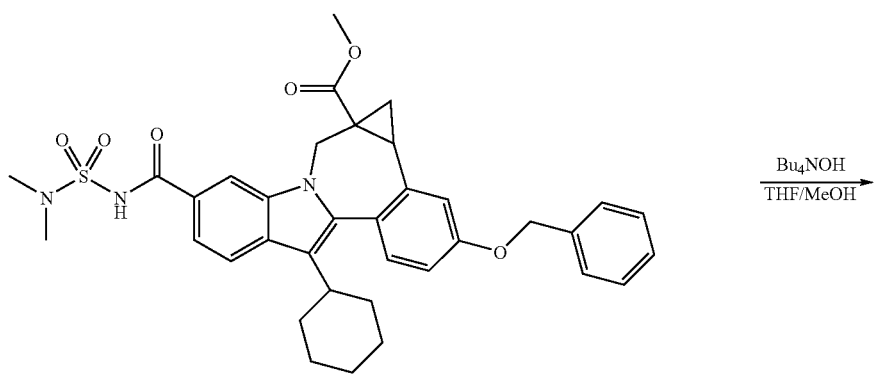
Bu$_4$NOH
―――――
THF/MeOH
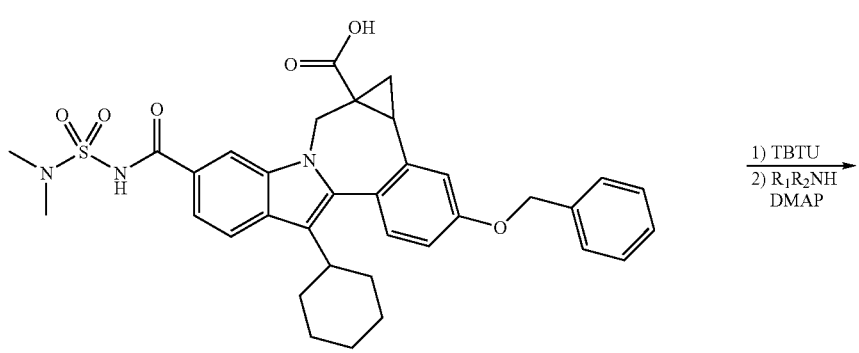
1) TBTU
2) R$_1$R$_2$NH
DMAP
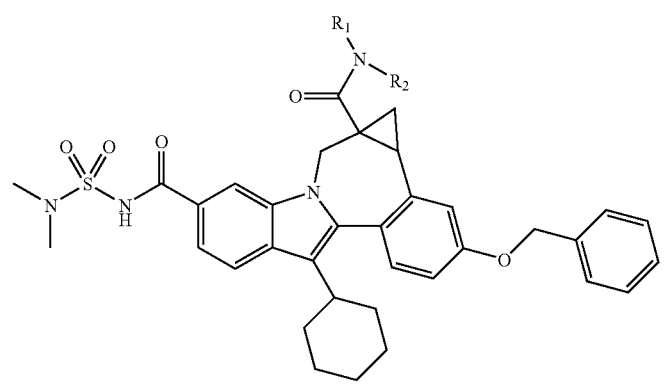

Further examples can be prepared by cyclopropanation of indolobenzazepine caboxamide intermediates of the type shown in Scheme 11. Indolobenzazepine acyl sulfamide acids of the type shown below can be coupled using methods known in the art to give the related trisubstituted piperazine carboxamides. These intermediates can be cyclopropanated to provide additional examples.

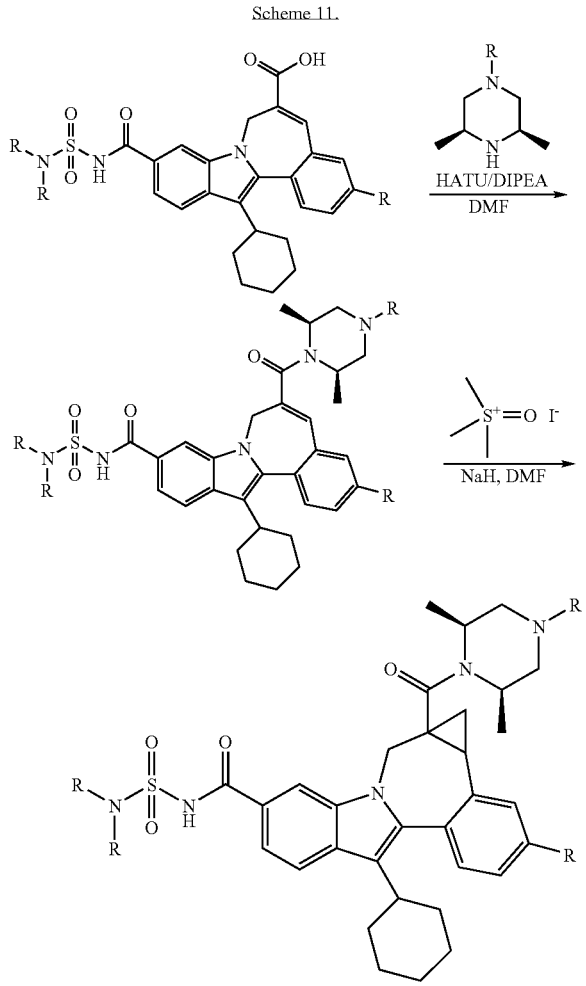

Biological Methods

The compounds demonstrated activity against HCV NS5B as determined in the following HCV RdRp assays.

HCVNS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 μg/ml and the cells were grown overnight at 20° C.

Cell pellets (3L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 μm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCVNS5B RdRp enzyme assay. HCV RdRp genotype 1b assays were run in a final volume of 60 μl in 96 well plates (Costar 3912). The assay buffer is composed of 20 mM Hepes, pH 7.5, 2.5 mM KCl, 2.5 mM MgCl2, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at 0.6 μCi (0.29 μM total UTP). Reactions were initiated by the addition of enzyme, incubated at 30° C. for 60 min, and stopped by adding 25 μl of 50 mM EDTA containing SPA beads (4 μg/μl, Amersham RPNQ 0007). Plates were read on a Packard Top Count NXT after >1 hr incubation at room temperature.

Modified HCVNS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 μg/μl beads. Order of addition in the assay: enzyme (14 nM) was added to diluted compound followed by the addition of a mixture of template (0.2 nM), 3H-UTP (0.6 μCi, 0.29 μM), and primer-bound beads, to initiate the reaction; concentrations given are final. Reactions were allowed to proceed for 4 hours at 30° C.

IC50 values for compounds were determined using seven different [I]. IC50 values were calculated from the inhibition using the formula $y=A+((B-A)/(1+((C/x)^D)))$.

FRET Assay Preparation. To perform the HCV FRET screening assay, 96-well cell culture plates were used. The FRET peptide (Anaspec, Inc.) (Taliani et al., *Anal. Biochem.* 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with dH$_2$O, NaCl added to 150 mM final, the FRET peptide diluted to 20 uM final from a 2 mM stock.

To prepare plates, HCV replicon cells, with or without a *Renilla* luciferase reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a CO$_2$ incubator at 37° C.

Assays. Subsequent to addition of the test compounds described above (FRET Assay Preparation), at various times the plate was removed and Alamar blue solution (Trek Diagnostics, #00-100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naïve Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. EC$_{50}$ values for a protease inhibitor titration were calculated as the concentration which caused a 50% reduction in FRET or luciferase activity. The two numbers generated for the compound plate, percent cytoxicity and percent activity were used to determine compounds of interest for further analysis.

Representative data for compounds are reported in Table 1.

TABLE 1

| Structure | IC$_{50}$(µM) | EC$_{50}$(µM) |
|---|---|---|
| | B | B |
| | B | B |

TABLE 1-continued

| Structure | IC$_{50}$(μM) | EC$_{50}$(μM) |
|---|---|---|
| (structure) | B | B |
| (structure) | B | B |
| (structure) | B | B |

TABLE 1-continued
| Structure | IC$_{50}$(μM) | EC$_{50}$(μM) |
|---|---|---|
| 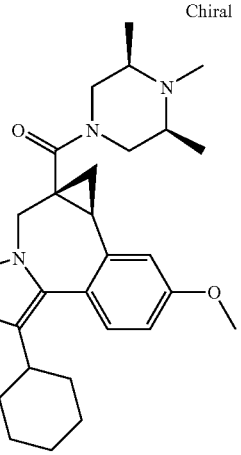 Chiral | B | B |
| 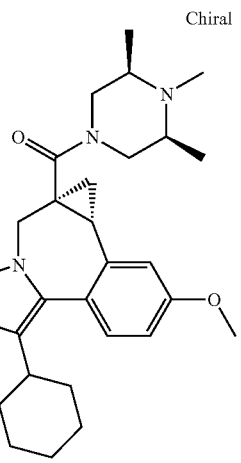 Chiral | B | B |
| 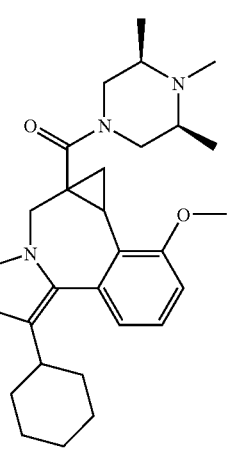 | B | B |

TABLE 1-continued

| Structure | IC$_{50}$(μM) | EC$_{50}$(μM) |
|---|---|---|
| | B | B |
| | B | B |
| | B | B |

TABLE 1-continued
| Structure | IC$_{50}$(μM) | EC$_{50}$(μM) |
|---|---|---|
| 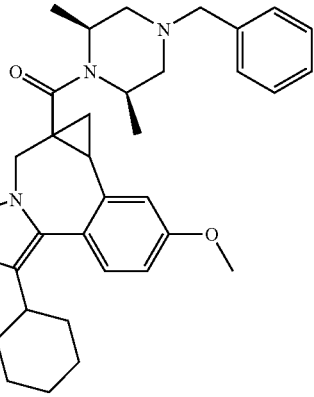 | E | D |
| 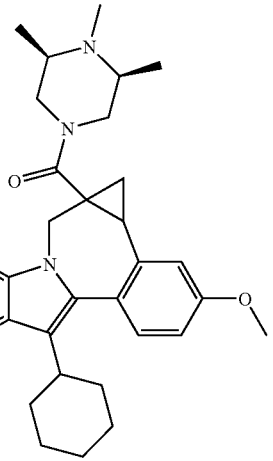 | B | B |
| 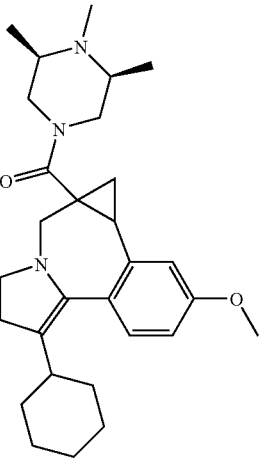 | B | B |
A >0.5 μM;
B 0.001 μm-0.5 μM;
C <0.02 μM but an exact value was not determined;
D >0.5 μM to 1 μM;
E >1 μM to 10 μM
IC$_{50}$ values were determined using the preincubation protocol.
EC$_{50}$ values were determined using the FRET assay.

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
|---|---|---|
| Omega IFN | IFN-ω | BioMedicines Inc., Emeryville, CA |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/SciClone Pharmaceuticals Inc, San Mateo, CA |
| Levovirin | IMPDH inhibitor | Ribapharm Inc., Costa Mesa, CA |
| Viramidine | IMPDH inhibitor | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| T67 | β-tubulin inhibitor | Tularik Inc., South San Francisco, CA |
| VX-497 | IMPDH inhibitor | Vertex Pharmaceuticals Inc., Cambridge, MA |
| VX-950/LY-570310 | serine protease inhibitor | Vertex Pharmaceuticals Inc., Cambridge, MA/Eli Lilly and Co. Inc., Indianapolis, IN |
| Omniferon | natural IFN-α | Viragen Inc., Plantation, FL |
| XTL-002 | monoclonal antibody | XTL Biopharmaceuticals Ltd., Rehovot, Isreal |

DESCRIPTION OF SPECIFIC EMBODIMENTS

Unless otherwise specified, analytical LCMS data on the following intermediates and examples were acquired using the following columns and conditions. Stop time: Gradient time+1 minute; Starting conc: 0% B unless otherwise noted; Eluent A: 5% $CH_3CN$/95% $H_2O$ with 10 mM $NH_4OAc$ (for columns A, D and E); 10% MeOH/90% $H_2O$ with 0.1% TFA (for columns B and C); Eluent B: 95% $CH_3CN$/5% $H_2O$ with 10 mM $NH_4OAc$ (for columns A, D and E); 90% MeOH/10% $H_2O$ with 0.1% TFA (for columns B and C); Column A: Phenomenex 10μ 4.6×50 mm C18; Column B: Phenomenex C18 10μ 3.0×50 mm; Column C: Phenomenex 4.6×50 mm C18 10μ; Column D: Phenomenex Lina C18 5μ 3.0×50 mm; Column E: Phenomenex 5μ 4.6×50 mm C18.

Intermediate 1

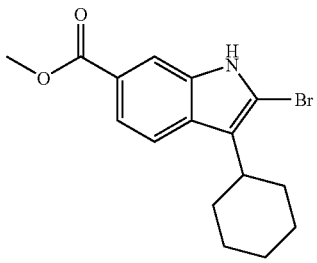

1H-Indole-6-carboxylic acid, 2-bromo-3-cyclohexyl-, methyl ester. Freshly recrystallized pyridinium tribromide (recrystallization from hot AcOH (5 mL per 1 g), rinsed with cold AcOH and dried under high vacuum over KOH) was added in portions (over 10 min.) to a stirred solution of methyl 3-cyclohexyl-1H-indole-6-carboxylate (60 g, 233 mmol) (prepared using procedures describe in WO2004/065367) in $CHCl_3$/THF (1:1, 1.25 L) at 2° C. The reaction solution was stirred at 0-5° C. for 2.5 h, and washed with sat. aq. $NaHSO_3$ (1 L), 1 N HCl (1 L) and brine (1 L). The organic layer was dried ($MgSO_4$) and concentrated. The resulting red oil was diluted with $Et_2O$ and concentrated. The resulting pink solid was dissolved into $Et_2O$ (200 mL) treated with hexanes (300 mL) and partially concentrated. The solids were collected by filtration and rinsed with hexanes. The mother liquor was concentrated to dryness and the procedure repeated. The solids were combined to yield 1H-indole-6-carboxylic acid, 2-bromo-3-cyclohexyl-, methyl ester (64 g, 190 mmol, 82%) as a fluffy pink solid, which was used without further purification. 1HNMR (300 MHz, $CDCl_3$) δ 8.47 (br s, 1H), 8.03 (d, J=1.4 Hz, 1H), 7.74 (dd, J=1.4, 8.8 Hz, 1H), 7.69 (d, J=8.8 Hz, 1H), 3.92 (s, 3H), 2.82 (tt, J=3.7, 11.7 Hz, 1H), 1.98-1.72 (m, 7H), 1.50-1.27 (m, 3H). 13CNMR (75 MHz, CDCl3) δ 168.2, 135.6, 130.2, 123.1, 120.8, 120.3, 118.7, 112.8, 110.7, 52.1, 37.0, 32.2(2), 27.0 (2), 26.1. LCMS: m/e 334 (M-H)⁻, ret time 3.34 min, column A, 4 minute gradient.

Intermediate 2

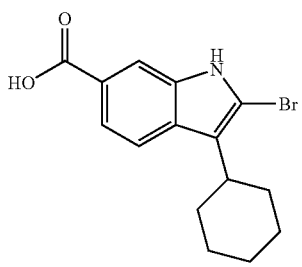

1H-Indole-6-carboxylic acid, 2-bromo-3-cyclohexyl-. A solution of methyl 2-bromo-3-cyclohexyl-1H-indole-6-carboxylate (20 g, 60 mmol) and LiOH (3.8 g, 160 mmol) in MeOH/THF/$H_2O$ (1:1:1, 300 mL) was heated at 90° C. for 2 h. The reaction mixture was cooled in an ice/$H_2O$ bath, neutralized with 1M HCl (~160 mL) diluted with $H_2O$ (250 mL) and stirred for 1 h at rt. The precipitates were collected by filtration, rinsed with $H_2O$ and dried to yield 1H-indole-6-carboxylic acid, 2-bromo-3-cyclohexyl- in quantitative yield, and was used without further purification.

An alternative procedure that can by used to provide 1H-indole-6-carboxylic acid, 2-bromo-3-cyclohexyl- is described below:

A solution of methyl 2-bromo-3-cyclohexyl-1H-indole-6-carboxylate (117 g, 349 mmol) and LiOH.$H_2O$ (26.4 g, 629 mmol) in MeOH/THF/$H_2O$ (1:1:1, 1.8 L) was heated at reflux for 3 h. The reaction mixture was cooled in an ice/$H_2O$ bath to ~2° C., and then neutralized with 1M HCl (~650 mL) that was added at such a rate that the temperature did not exceed 5° C. On addition, the mixture was diluted with $H_2O$ (1 L) and stirred while warming to ambient temperature. The resultant precipitates were collected by filtration, rinsed with $H_2O$ and dried to yield the mono THF solvate of 1H-indole-6-carboxylic acid, 2-bromo-3-cyclohexyl- (135.5 g, 345 mmol, 99%) as a yellow solid, which was used without further purification. 1HNMR (300 MHz, $CDCl_3$) δ 11.01 (br s, 1H), 8.77 (s, 1H), 8.07 (d, J=1.5 Hz, 1H), 7.82 (dd, J=1.5, 8.8 Hz, 1H), 7.72 (d, J=8.8 Hz, 1H), 3.84-3.74 (m, 4H), 2.89 (m, 1H), 1.98-1.72 (m, 11H), 1.50-1.24 (m, 3H). 13CNMR (75 MHz, CDCl3) δ 172.7, 135.5, 130.7, 122.3, 120.9(2), 118.8, 113.3, 111.1, 67.9(2), 37.0, 32.2(2), 27.0(2), 26.1, 25.5(2). LCMS: m/e 320 (M-H)⁻, ret time 2.21 min, column A, 4 minute gradient.

Intermediate 3

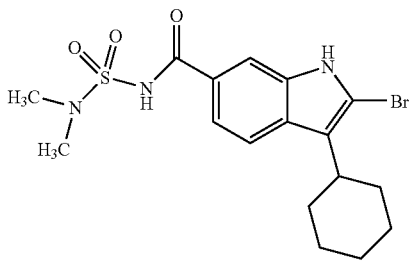

1H-Indole-6-carboxamide, 2-bromo-3-cyclohexyl-N-[(dimethylamino)sulfonyl]-. 1,1'-Carbonyldiimidazole (1.17 g, 7.2 mmol) was added to a stirred solution of 2-bromo-3-cyclohexyl-1H-indole-6-carboxylic acid (2.03 g, 6.3 mmol) in THF (6 mL) at 22° C. The evolution of $CO_2$ was instantaneous and when it slowed the solution was heated at 50° C. for 1 hr and then cooled to 22° C. N,N-Dimethylsulfamide (0.94 g, 7.56 mmol) was added followed by the dropwise addition of a solution of DBU (1.34 g ,8.8 mmol) in THF (4 mL). Stirring was continued for 24 hr. The mixture was partitioned between ethyl acetate and dilute HCl. The ethyl acetate layer was washed with water followed by brine and dried over $Na_2SO_4$. The extract was concentrated to dryness to leave the title product as a pale yellow friable foam, (2.0 g, 74%, >90% purity, estimated from NMR). $^1$H NMR (300 MHz, DMSO-D6) δ ppm 1.28-1.49 (m, 3H) 1.59-2.04 (m, 7H) 2.74-2.82 (m, 1H) 2.88 (s, 6H) 7.57 (dd, J=8.42, 1.46 Hz, 1H) 7.74 (d, J=8.78 Hz, 1H) 7.91 (s, 1H) 11.71 (s, 1H) 12.08 (s, 1H).

An alternative method for the preparation of 1H-indole-6-carboxamide, 2-bromo-3-cyclohexyl-N-[(dimethylamino)sulfonyl]- is described below.

2-bromo-3-cyclohexyl-1H-indole-6-carboxylic acid (102.0 g, 0.259 mol) and dry THF (300 mL). were added to a 1 L four necked round bottom flask equipped with a mechanical stirrer, a temperature controller, a $N_2$ inlet, and a condenser, and the mixture was placed under $N_2$. After stirring for 10 min, CDI (50.3 g, 0.31 mol) was added portion wise. The reaction mixture was then heated to 50° C. for 2 h. After cooling to 30° C., N,N-dimethylaminosulfonamide (41.7 g, 0.336 mol) was added in one portion followed by addition of DBU (54.1 mL, 0.362 mol) drop wise over a period of 1 h. The reaction mixture was then stirred at rt for 20 h. The solvent was removed in vacuo and the residue was partitioned between EtOAc and 1 N HCl (1:1, 2 L). The organic layer was separated and the aqueous layer was extracted with EtOAc (500 mL). The combined organic layers were washed with brine (1.5 L) and dried over MgSO₄. The solution was filtered, and then concentrated in vacuo to give the crude product (111.0 g). The crude product was suspended in EtOAc (400 mL) at 60° C., and heptane (2 L) was then added slowly. The resulting mixture was stirred and cooled to 0° C. It was then filtered. The filter cake was rinsed with a small amount of heptane and house vacuum air dried for 2 days. The product was collected as a white solid (92.0 g, 83%). $^1$H NMR (MeOD, 300 MHz) δ 7.89 (s, H), 7.77 (d, J=8.4 Hz, 1H), 7.55 (dd, J=8.4 and 1.8 Hz, 1H), 3.01 (s, 6H), 2.73-2.95 (m, 1H), 1.81-2.05 (m, 8H), 1.39-1.50 (m, 2H); m/z 429 (M+H)+.

nyl)- (52.8 g, 109 mmol, 87%) as a yellow powder which was used without further purification. 1HNMR (300 MHz, d6-DMSO) δ 11.66 (s, 1H), 8.17 (s, 1H), 7.75 (d, J=8.4 Hz, 1H), 7.74 (d, J=8.4 Hz, 1H), 7.59 (dd, J=1.4, 8.4 Hz, 1H), 7.23-7.16 (m, 2H), 7.08 (dd, J=2.6, 8.4 Hz, 1H), 6.54 (d, J=8.8 Hz, 1H), 3.86 (s, 3H), 3.22-3.08 (m, 1H), 2.91 (s, 6H), 2.00-1.74 (m, 7H), 1.60-1.38 (m, 3H). 13CNMR (75 MHz, CDCl3) δ 165.7, 158.8, 147.2, 139.1, 134.3, 132.0, 123.4, 122.0, 119.2, 118.2, 114.8, 112.3, 110.4, 109.8, 79.6, 45.9, 37.2(2), 34.7, 32.0(2), 25.9(2), 24.9. LCMS: m/e 482 (M−H)⁻, ret time 2.56 min, column A, 4 minute gradient.

Intermediate 4

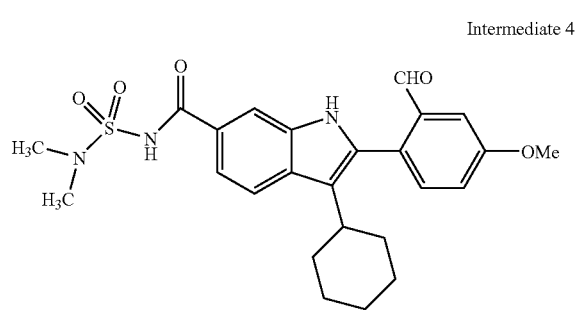

Intermediate 5

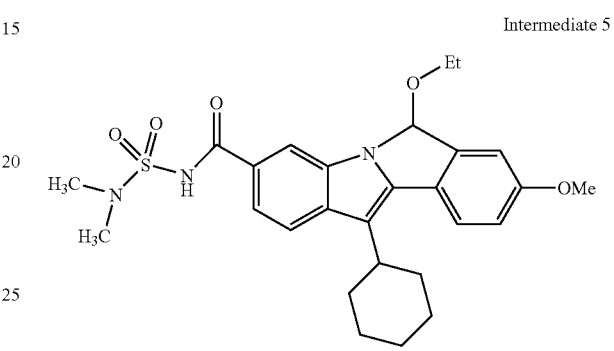

1H-Indole-6-carboxamide, 3-cyclohexyl-N-[(dimethylamino)sulfonyl]-2-(2-formyl-4-methoxyphenyl)-. A mixture of the 2-Bromo-3-cyclohexyl-N-[(dimethylamino)sulfonyl]-1H-indole-6-carboxamide (4.28g, 0.01 mol), 4-methoxy-2-formylphenyl boronic acid (2.7 g, 0.0 15 mol), 2-dicyclohexylphosphino-2',6'-dimethoxy-biphenyl (41 mg, 0.0001 mol), palladium acetate (11.2 mg), and finely ground potassium carbonate (4.24 g, 0.02 mol) in toluene (30 mL) was stirred under reflux under nitrogen for 30 min, at which time LC/MS analysis showed the reaction to be complete. The reaction mixture was then diluted with ethyl acetate and water, and then acidified with an excess of dilute HCl. The ethyl acetate layer was then collected and washed with dilute HCl, water and brine. The organic solution was then dried (magnesium sulfate), filtered and concentrated to give a gum. The gum was diluted with hexanes (250 ml) and ethyl acetate (25 mL), and the mixture was stirred for 20 hr at 22° C. during which time the product was transformed into a bright yellow granular solid (4.8 g) which was used directly without further purification.

An alternative procedure for the preparation of 1H-indole-6-carboxamide, 3-cyclohexyl-N-[(dimethylamino)sulfonyl]-2-(2-formyl-4-methoxyphenyl)- is provided below:

To a slurried solution of 2-bromo-3-cyclohexyl-N-[(dimethylamino)sulfonyl]-indole-6-carboxamide (54.0 g, 126 mmol), 4-methoxy-2-formylphenylboronic acid (29.5 g, 164 mmol) and LiCl (13.3 g, 315 mmol) in EtOH/toluene (1:1, 1 L) was added a solution of Na₂CO₃ (40.1 g, 379 mmol) in water (380 mL). The reaction mixture was stirred 10 min. and then Pd(PPh3)4 (11.3 g, 10.0 mmol) was added. The reaction solution was flushed with nitrogen and heated at 70° C. (internal monitoring) overnight and then cooled to rt. The reaction was diluted with EtOAc (1 L) and EtOH (100 mL), washed carefully with 1N aqueous HCl (1 L) and brine (500 mL), dried (MgSO₄), filtered and concentrated. The residual solids were stirred with Et₂O (600 mL) for 1 h and collected by filtration to yield 1H-indole-6-carboxamide, 3-cyclohexyl-N-[(dimethylamino)sulfonyl]-2-(2-formyl-4-methoxyphe- 6H-Isoindolo[2,1-a]indole-3-carboxamide, 11-cyclohexyl-N-[(dimethylamino)sulfonyl]-6-ethoxy-8-methoxy-.
To a 5 L four necked round bottom flask equipped with a temperature controller, a condenser, a N2 inlet and a mechanical stirrer, was charged toluene (900 mL), EtOH (900 mL), 2-bromo-3-cyclohexyl-N-(N,N-dimethylsulfamoyl)-1H-indole-6-carboxamide (90 g, 0.21 mol), 2-formyl-4-methoxyphenylboronic acid (49.2 g, 0.273 mol) and LiCl (22.1 g, 0.525 mol). The resulting solution was bubbled with N₂ for 15 mins. A solution of Na₂CO₃ (66.8 g, 0.63 mol) in H₂O (675 mL) was added and the reaction mixture was bubbled with N₂ for another (10 mins). Pd(PPh3)4 (7.0 g, 6.3 mmol) was added and the reaction mixture was heated to 70° C. for 20 h. After cooling to 35° C., a solution of 1 N HCl (1.5 L) was added slowly. The resulting mixture was transferred to a 6 L separatory funnel and extracted with EtOAc (2×1.5 L). The combined organic extracts were washed with brine (2 L), dried over MgSO4, filtered and concentrated in vacuo to give a yellow solid, which was triturated with 20% EtOAc in hexane (450 mL, 50° C. to 0° C.) to give 3-cyclohexyl-N-(N,N-dimethylsulfamoyl)-2-(2-formyl-4-methoxyphenyl)-1H-indole-6-carboxamide(65.9 g) as a yellow solid. HPLC purity, 98%.

The mother liquid from the trituration was concentrated in vacuo. The residue was refluxed with EtOH (50 mL) for 3 h. The solution was then cooled to 0° C. The precipitates were filtered and washed with cooled TBME (5° C.) (20 mL). The filter cake was house vacuum air dried to give a further quantity of the title compound as a white solid (16.0 g). HPLC purity, 99%. $^1$H NMR (CDCl3, 300 MHz) δ 8.75 (s, 1H), 7.96 (s, 1H), 7.73 (d, J=8.4 Hz, 1H), 7.67 (d, J=8.4 Hz, 1H), 7.45 (dd, J=8.4 and 1.4 Hz, 1H), 7.09 (d, J=2.2 Hz, 1H), 6.98 (dd, J=8.4 and 2.2Hz, 1H), 6.50 (s, 1H), 3.86 (s, 3H), 3.05 (s, 6H), 2.92-3.13 (m, 3H), 1.85-1.93 (m, 7H), 1.40-1.42 (m, 3H), 1.05 (t, J=7.1 Hz, 3H). m/z 512 (M+H)+.

Intermediate 4

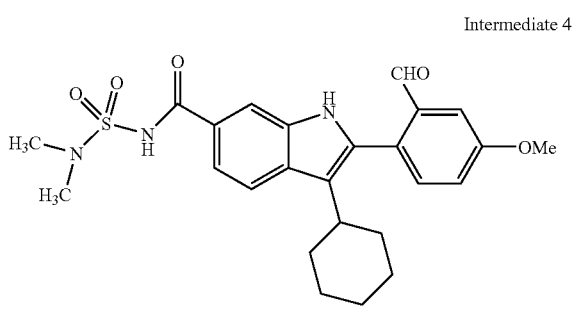

1H-indole-6-carboxamide, 3-cyclohexyl-N-[(dimethylamino)sulfonyl]-2-(2-formyl-4-methoxyphenyl)-. 11-cyclohexyl-N-(N,N-dimethylsulfamoyl)-6-ethoxy-8-methoxy-6H-isoindolo[2,1-a]indole-3-carboxamide was dissolved in THF (75 mL). To the solution was added a solution of 2 N HCl (300 mL). The mixture was vigorously stirred under N2 at rt for 16 h. The resulting suspension was filtered and washed with cooled TBME (2×30 mL). the filer cake was vacuum air dried overnight to give the title compound as a yellow solid. HPLC purity, 99% $^1$H NMR (DMSO-d6, 300 MHz) δ 11.65 (s, 1H), 8.16 (s, 1H), 7.76 (d, J=5.9 Hz, 1H), 7.73 (d, J=5.9 Hz, 1H), 7.58 (dd, J=8.5 and 1.5 Hz, 1H), 7.17-7.20 (m, 2H), 7.08 (dd, J=8.5 and 1.4 Hz, 1H), 6.55 (d, J=8.6 Hz, 1H), 3.86 (s, 3H), 3.14-3.18 (m, 1H), 2.91 (s, 6H), 1.75-1.99 (m, 7H), 1.48-1.60 (m, 3H); m/z 484 (M+H)+.

Intermediate 6

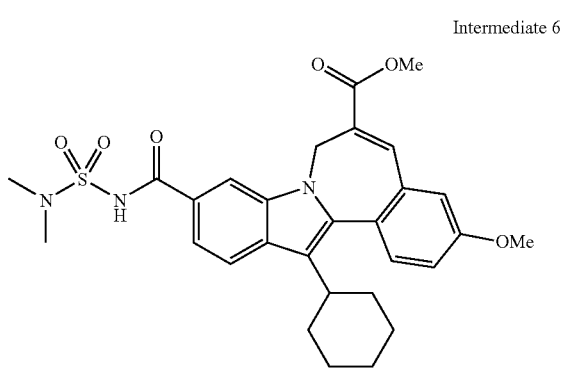

7H-Indolo[2,1a][2]benzazepine-6-carboxylic acid, 13-cyclohexyl-10-[[[(dimethylamino)sulfonyl]amino]carbonyl]-3-methoxy-, methyl ester. A mixture of the 3-cyclohexyl-N-(N,N-dimethylsulfamoyl)-2-(2-formyl-4-methoxyphenyl)-1H-indole-6-carboxamide (4.8 g, 0.01 mol), methyl 2-(dimethoxyphosphoryl)acrylate (9.7 g, 0.02 mol) and cesium carbonate (7.1 g, 0.02 mol) in DMF (28mL) was stirred for 20 hr at an oil bath temperature of 55° C. The mixture was poured into ice-water and acidified with dilute HCl to precipitate the crude product. The solid was collected, dried and flash chromatographed on SiO$_2$ (110 g) using an ethyl acetate and methylene chloride (1:10) solution containing 2% acetic acid. Homogeneous fractions were combined and evaporated to afford the title compound as a pale yellow solid (3.9 g, 71% yield). MS: 552 (M=H+).

An alternate procedure for the preparation of 7H-indolo[2,1-a][2]benzazepine-6-carboxylic acid, 13-cyclohexyl-10-[[[(dimethylamino)sulfonyl]amino]carbonyl]-3-methoxy-, methyl ester is provided below.

A solution of 11-cyclohexyl-N-[(dimethylamino)sulfonyl]-6-hydroxy-8-methoxy-6H-isoindolo[2,1-a]indole-3-carboxamide (cyclic hemiaminal) (63.0 g, 130 mmol), methyl 2-(dimethoxyphosphoryl)acrylate (60 g, 261 mmol), cesium carbonate (106 g, 326 mmol) in DMF (400 mL) was heated at 60° C. (bath temp) for 4.5 h. Additional methyl 2-(dimethoxyphosphoryl)acrylate (15 g, 65 mmol) and cesium carbonate (21.2 g, 65 mmol) were added and the reaction was heated at 60° C. overnight then and cooled to rt. The stirring reaction mixture was diluted with H$_2$O (1 L), slowly neutralized with 1N aqueous HCl (800 mL), stirred 3 h, and then the precipitates were collected by filtration. The solids were triturated with Et2O (800 mL) and dried to yield methyl 7H-indolo[2,1-a][2]benzazepine-6-carboxylic acid, 13-cyclohexyl-10-[[[(dimethylamino)sulfonyl]amino]carbonyl]-3-methoxy-, methyl ester (70.2 g, 127 mmol, 98%) as a yellow solid which was used without further purification. 1HNMR (300 MHz, CDCl3) δ 8.67 (s, 1H), 8.09 (s, 1H), 7.86 (d, J=8.4 Hz, 1H), 7.80 (s, 1H), 7.50 (d, J=8.4 Hz, 1H), 7.42 (d, J=8.8 Hz, 1H) 7.08 (dd, J=2.6, 8.8 Hz, 1H), 6.98 (d, J=2.6 Hz, 1H), 5.75-5.51 (m, 1H), 4.29-4.01 (m, 1H), 3.89 (s, 3H), 3.82 (s, 3H), 3.05 (s, 6H), 2.87-2.73 (m, 1H), 2.11-1.12 (m, 10H). LCMS: m/e 550 (M−H)−, ret time 3.21 min, column A, 4 minute gradient.

Intermediate 7

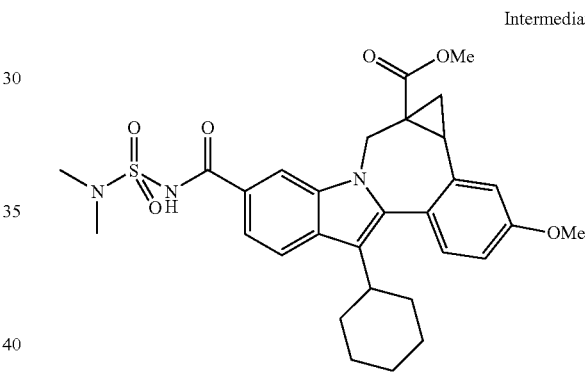

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, methyl ester, (+/−)-. DMSO (5 mL) was added to a mixture of trimethylsulfoxonium iodide (199 mg, 0.906 mmol) and NaH (38 mg in 60% oil dispersion, 0.953 mmol) in a round-bottomed flask. The reaction mixture was stirred at rt for 0.5 hr. 7H-Indolo[2,1-a][2]benzazepine-6-carboxylic acid, 13-cyclohexyl-10-[[[(dimethylamino)sulfonyl]amino]carbonyl]-3-(methoxy)-, methyl ester (125 mg, 0.227 mmol) was then added and the reaction mixture was stirred at rt. for 3 hr., and then at 50° C. for a further 3 hr. The reaction was then quenched with water and acidified with 1N HCl solution. The crude product then precipitated as a light yellow solid which was collected by filtration and air dried, (106 mg, 83% yield). 6 mg of this material was then purified by Prep. HPLC to afford the title compound as a light yellow solid (1.8 mg). MS m/z 566(MH$^+$), Retention time: 3.850 min.1H NMR (500 MHz, MeOD) δ ppm 0.28 (m, 0.36H) 1.19-2.20 (m, 11.64H) 2.70-3.02 (m, 2H) 3.03 (s, 2.16H) 3.05 (s, 3.84H) 3.49 (d, J=15.26 Hz, 0.64H) 3.54 (s, 1.92H) 3.83 (s, 1.08H) 3.91 (s, 3H) 4.08 (d, J=15.26 Hz, 0.36H) 5.29 (d, J=15.26 Hz, 0.36H) 5.50 (d, J=14.95 Hz, 0.64H) 6.98-7.06 (m, 1H) 7.16 (d, J=2.44 Hz, 0.36H) 7.23 (d, J=2.44 Hz, 0.64H) 7.30 (d, J=8.55 Hz, 0.64H) 7.34 (d, J=8.55 Hz, 0.36H) 7.56 (dd, J=8.55, 1.53 Hz, 0.64H) 7.63 (dd, J=8.55, 1.53 Hz, 0.36H) 7.88 (d, J=8.55 Hz, 0.64 H) 7.91 (d, J=8.55 Hz, 0.36H) 8.12 (s, 0.36H) 8.33 (d, J=1.53 Hz, 0.64H).

An alternative procedure for the preparation of the title compounds is provided below.

To a flame dried, four necked, 1 L round bottom flask equipped with a mechanical stirrer, N2 inlet and a thermometer, under N2, was charged sodium hydride (95%) (3.09 g, 129.2 mmol) and dry DMF (200 mL). With vigorous stirring, trimethylsulfoxonium iodide (32.5 g, 147.3 mmol) portion wise during which time the temperature rose to 30° C. After stirring for 30 mins, a solution of 7H-Indolo[2,1-a][2]benzazepine-6-carboxylic acid, 13-cyclohexyl-10-[[[(dimethylamino)sulfonyl]amino]carbonyl]-3-(methoxy)-, methyl ester (33.8 g, 61.3 mmol) in dry DMF (70 mL) was added quickly. The reaction mixture was stirred below 30° C. for 30 mins and then poured into an ice cold solution of 1 N HCl (130 mL) in H2O (2 L) portion wise. After the resulting suspension was mechanically stirred for 1 h, the precipitates were filtered and the filter cake was washed with H2O (100 mL). The filter cake was partitioned between EtOAc and 0.5 N HCl (1:1, 4 L). The organic phase was separated, washed with H2O (1 L) and brine (1 L), dried over MgSO$_4$, filtered and concentrated in vacuo. The residue was dissolved in EtOAc (150 mL), and the solution was filtered through a silica gel pad (300 g in hexane) and rinsed with 50% EtOAc in hexane (5 L). The filtrate was concentrated in vacuo to give a slightly yellow solid which was triturated with 10% EtOAc in TBME (220 mL) from 50° C. to 0° C. to give cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, methyl ester, (+/−)- as a white solid (26.1 g, 75% yield). HPLC purity, 100%. $^1$H NMR (DMSO-d$_6$, 300 MHz) δ 11.61 (s, 1H), 8.47 (s, 0.5H), 8.25 (s, 0.5H), 7.81-7.88 (m, 1H), 7.57-7.63 (m, 1H), 7.23-7.29 (m, 2H), 7.01-7.07 (m, 1H), 5.43 (d, J=15.0 Hz, 3.75 (s, 1H), 3.08-3.47 (m, 0.5H), 3.29 (s, 3H), 2.73-2.92 (m, 8H), 1.11-1.99 (m, 10.5H), 0.20 (m, 0.5H); m/z 566 (M+H)$^+$.

Intermediate 8

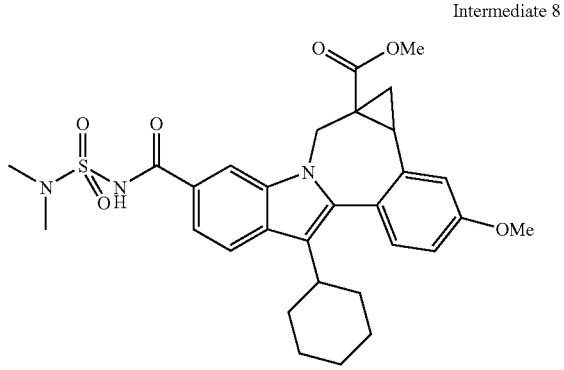

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, methyl ester, (−)-. A sample of (+/−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-methyl ester was dissolved in EtOH/CH$_3$CN 1/1+0.5% DEA at a concentration of 50 mg/ml. [The addition of DEA ensures the compound remains in solution during the injection process]. This solution was then injected onto a Thar SFC-350 preparative SFC under the conditions shown below.

Preparative conditions on Thar SFC-350: Column: Chiralcel OJ-H 5×25 cm; mobile phase: 25% MeOH/ CH3CN (1/1) in CO2; pressure (bar): 100; flow rate (ml/min): 240; solution concentration (mg/ml): 50; injection amount (ml): 4.5-5; Cycle time (min/inj): 6.5-7; Temperature (° C.): 45; throughput (g/hr): ~2; Detector wavelength (nm): 254.

From 371.4 g of racemic starting material, a total of 177.3 g of the desired second eluting (−) isomer was obtained, containing ~1 Meq of diethylamine. This material was purified using the following procedure. The mixture (24.7 g) dissolved in dichloromethane (800 mL)) was washed sequentially with; 0.5 N HCl (1×400 mL, 1×240 mL), H$_2$O (2× 240 mL), and brine (2×240 mL). The organic layer was then dried (Anhy. Na$_2$SO$_4$), filtered and evaporated to give 22.33 g of (cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, methyl ester, (−)- as a yellow solid (92% recovery). HPLC$^1$>99% (Rt 2.38 min); LC/MS (ES$^+$) 566.51 (M+H, 100); [α]$_D^{25C}$−194.64° (c 1.03, MeOH). Anal. Calcd for C$_{30}$H$_{35}$N$_3$O$_6$S.0.33H$_2$O: C, 63.04;H, 6.29; N, 7.35; S, 5.61; H$_2$O, 1.04. Found: C, 63.07; H, 6.01; N, 7.24; S, 5.58; H$_2$O, 1.03. The NMR shows the absence of Et$_2$NH. The EE of this material was determined to be >99% using the following analytical HPLC procedure.

Analytical conditions of ee determination on Thar analytical SFC. Analytical Column: Chiralcel OJ (0.46×25cm, 10 µl); BPR pressure: 100 bars; Temperature: 35° C.; Flow rate: 3.0 ml/min; Mobile Phase: 15% MeOH/CH$_3$CN (1/1) in CO$_2$; Detector Wavelength: 254 nm; Retention time (min): 4, 6.5.

Intermediate 9

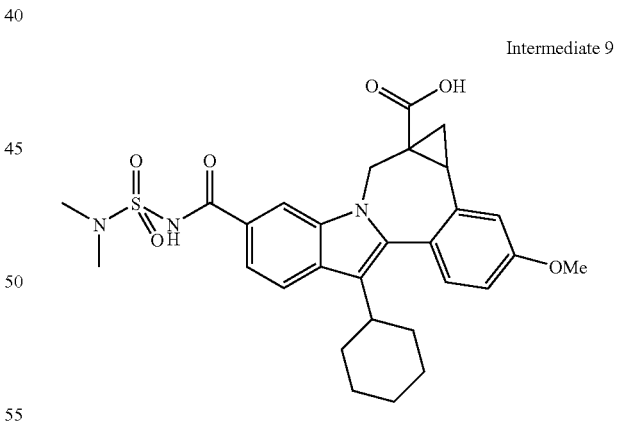

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, (−)-. To a solution of (−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, methyl ester (22.33 g, 39.5 mmol) in MeOH (300 mL) was added 1 N NaOH (120 mL) slowly over 20 min., while maintaining the reaction temperature <30° C. The mixture was stirred at rt under N$_2$ for 18 h. The HPLC indicated the reaction was complete. To the reaction solution was added 1

N HCl (130 mL). After addition was complete, the pH of the reaction mixture was about 2. The methanol in the reaction mixture was evaporated. Water (300 mL) was added to the mixture which was then extracted with $CH_2Cl_2$ (1×600 mL, 1×200 mL). The combined extracts were washed with $H_2O$ (2×300 mL), brine (2×300 mL), dried ($Na_2SO_4$) and evaporated to give 20.82 g (96% yield) of the title compound as a yellow solid. HPLC conditions column: Phenomenoex Synergi Polar-RP 4 um 4.6×50 mm; UV: 220 nm; gradient time: 4 min; flow rate: 4 mL/min, 75-100% B; solvent A: 10% MeOH/90% $H_2O$ with 0.2% $H_3PO_4$, solvent B: 90% MeOH/10% $H_2O$ with 0.2% $H_3PO_4$. HPLC>99% (Rt 1.80 min.) LC/MS ($ES^+$) 552.25 (M+H, 100); $[\alpha]_D^{25C}$ −166.99° (c 1.00, MeOH). GC analysis: $CH_2Cl_2$ 4.94%; Anal. Calcd for $C_{29}H_{33}N_3O_6S.0.16H_2O.0.35\ CH_2Cl_2$: C, 60.37; H, 5.87; N, 7.20; S, 5.49; $H_2O$, 0.49; $CH_2Cl_2$, 5.02. Found: C, 59.95; H, 5.89; N, 7.03; S, 5.38; $H_2O$, 0.47; $CH_2Cl_2$, 4.94

Intermediate 10

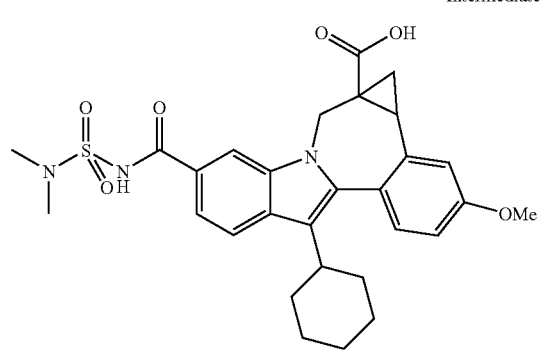

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, (+/−)-. To a solution of (+/−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, methyl ester (100 mg, 0.177 mmol) in THF/Methanol mixture (2.0 mL/2.0 mL), 2N NaOH solution (1.0 mL) was added. The reaction mixture was heated at 90° C. under microwave conditions for 5 min. It was then concentrated, acidified with 1N HCl solution and extracted with ethyl acetate (2×20 mL). The organic layers were combined, dried ($MgSO_4$), filtered and concentrated. The residue was purified by preparative HPLC to afford the desired product as a light yellow solid, (59 mg, 60% yield). MS m/z 552(MH$^+$), Retention time: 3.850 min. 1H NMR (300 MHz, MeOD) δ ppm 0.25 (m, 0.38H) 1.14-2.22 (m, 11.62H) 2.69-2.98 (m, 2H) 3.02 (s, 2.28H) 3.02 (s, 3.72H) 3.41 (d, J=15.00 Hz, 0.62H) 3.88 (s, 3H) 4.01 (d, J=15.00 Hz, 0.38 H) 5.26 (d, J=15.00 Hz, 0.38H) 5.45 (d, J=14.64 Hz, 0.62H) 6.94-7.02 (m, 1H) 7.13 (d, J=2.56 Hz, 0.38H) 7.21 (d, J=2.20 Hz, 0.62H) 7.26 (d, J=8.42 Hz, 0.62H) 7.30 (d, J=8.78 Hz, 0.38H) 7.53 (dd, J=8.42, 1.46 Hz, 0.62H) 7.61 (dd, J=8.60, 1.65 Hz, 0.38H) 7.85 (d, J=8.42 Hz, 0.62H) 7.89 (d, J=8.42 Hz, 0.38H) 8.10 (s, 0.38H 8.28 (d, J=1.46 Hz, 0.62H).

Intermediate 11

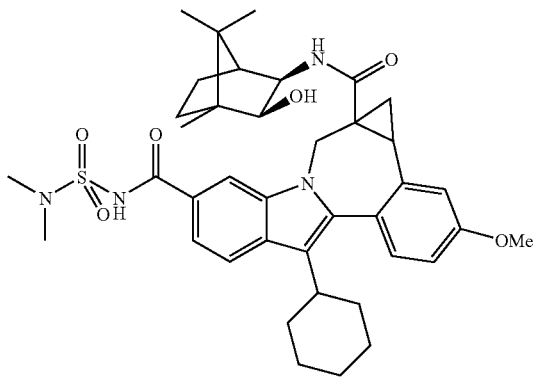

Cycloprop[d]indolo[2,1-a][2]benzazepine-1a,5(2H)-dicarboxamide, 8-cyclohexyl-$N^5$-[(dimethylamino)sulfonyl]-1,12b-dihydro-$N^{1a}$-[(2R, 3S)-3-hydroxy-4,7,7-trimethylbicyclo[2.2.1]hept-2-yl]-11-methoxy-, (1aR)-[partial]-. TBTU (437 mg, 1.36 mmol) and DIPEA (0.95 mL, 5.436 mmol) were added to a solution of (+/−) cycloprop[d]indolo[2,1-a][2]benzazepine-1a(2H)-carboxylic acid, 8-cyclohexyl-5-[[[(dimethylamino)sulfonyl]amino]carbonyl]-1, 12b-dihydro-11-methoxy- (500 mg, 0.906 mmol) in DMSO (20.0 mL). The reaction mixture was stirred at rt for 15 min. (2S,3R)-3-Amino-1,7,7-trimethylbicyclo[2.2.1]heptan-2-ol (280 mg, 1.36 mmol) was then added and the reaction mixture was stirred at rt overnight. The reaction mixture was quenched with water and acidified with 1N HCl solution. A brown solid separated which was collected by filtration. This material was then fractionated by Preparative HPLC under the following conditions. Column: Waters Sunfire 19 mm×100 mm; Solvent A: 10% CH3CN-90% H2O-0.1% TFA; Solvent B: 90% CH3CN-10% H2O-0.1% TFA; Program: Start with 65% solvent B, initial hold time for 5 min, then gradually increase to 90% solvent B in 30 min with flow rate 25 mL/min. Load: 50-60 mg/run.

Cycloprop[d]indolo[2,1-a][2]benzazepine-1a,5(2H)-dicarboxamide, 8-cyclohexyl-$N^5$-[(dimethylamino)sulfonyl]-1,12b-dihydro-$N^{1a}$-[(2R,3S)-3-hydroxy-4,7,7-trimethylbicyclo[2.2.1]hept-2-yl]-11-methoxy-, (1aR)-[partial]-elutes before Cycloprop[d]indolo[2,1-a][2]benzazepine-1a,5(2H)-dicarboxamide, 8-cyclohexyl-$N^5$-[(dimethylamino)sulfonyl]-1,12b-dihydro-$N^{1a}$-[(2R,3S)-3-hydroxy-4,7,7-trimethylbicyclo[2.2.1]hept-2-yl]-11-methoxy-, (1aS)-[partial]- under the HPLC conditions described above. Product obtained as a light yellow solid, 230 mg, 36% yield). MS m/703(MH$^+$), Retention time: 3.936 min. 1H NMR (500 MHz, MeOD) δ ppm 0.14-0.24 (m, 2.64H) 0.51 (s, 2.46H) 0.72-2.21 (m, 20.9H) 2.49 (m, 0.18 H) 2.62 (m, 0.82H) 2.85 (m, 0.18H) 2.96 (m, 0.82H) 3.03 (s, 6H) 3.39 (m, 0.82H) 3.49-3.58 (m, 1.64H) 3.71-3.80 (m, 0.36H) 3.90 (s, 3H) 4.17 (d, J=14.65Hz, 0.18H) 5.06 (d, J=14.65 Hz, 0.18H) 5.37 (d, J=14.95 Hz, 0.82H) 6.73 (d, J=5.49 Hz, 0.82H) 6.98-7.05 (m, 1H) 7.08 (d, J=4.58 Hz, 0.18H) 7.10 (d, J=2.44 Hz, 0.18H) 7.21 (d, J=2.44 Hz, 0.82H) 7.31 (d, J=8.55 Hz, 0.82H) 7.34 (d, J=8.55 Hz, 0.18H) 7.59-7.64 (m, 1H) 7.87-7.93 (m, 1H) 7.99 (s, 0.18H) 8.09 (d, J=1.22 Hz, 0.82H).

Intermediate 12

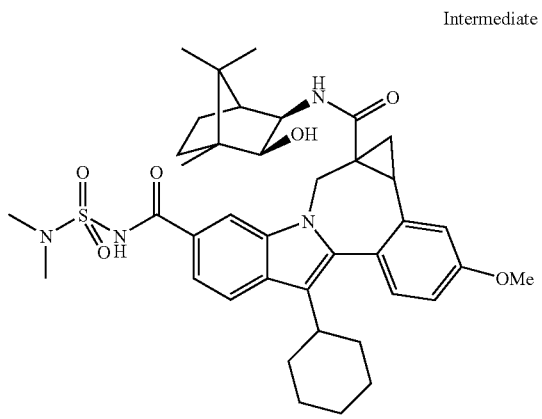

Cycloprop[d]indolo[2,1-a][2]benzazepine-1a, 5(2H)-dicarboxamide, 8-cyclohexyl-$N^5$-[(dimethylamino)sulfonyl]-1,12b-dihydro-$N^{1a}$-[(2R,3S)-3-hydroxy-4,7,7-trimethylbicyclo[2.2.1]hept-2-yl]-11-methoxy-, (1aS)-[partial]-. TBTU (437 mg, 1.36 mmol) and DIPEA (0.95 mL, 5.436 mmol) were added to a solution of (+/−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy- (500 mg, 0.906 mmol) in DMSO (20.0 mL). The reaction mixture was stirred at rt for 15 min. Then (2S,3R)-3-amino-1,7,7-trimethylbicyclo[2.2.1]heptan-2-ol (280 mg, 1.36 mmol) was added, and the reaction mixture was stirred at rt overnight. The reaction mixture was quenched with water and then acidified with 1N HCl solution. A brown colored solid separated that was collected by filtration. This material was then fractionated by preparative HPLC under the following conditions. Column: Waters Sunfire 19 mm×100 mm; Solvent A: 10% CH3CN-90% H2O-0.1% TFA; Solvent B: 90% CH3CN-10% H2O-0.1% TFA; Program: Start with 65% solvent B, initial hold time for 5 min, then gradually increase to 90% solvent B in 30 min with flow rate 25 mL/min. Load: 50-60 mg/run.

Cycloprop[d]indolo[2,1-a][2]benzazepine-1a,5(2H)-dicarboxamide, 8-cyclohexyl-$N^5$-[(dimethylamino)sulfonyl]-1,12b-dihydro-$N^{1a}$-[(2R,3S)-3-hydroxy-4,7,7-trimethylbicyclo[2.2.1]hept-2-yl]-11-methoxy-, (1aS-[partial]- elutes after cycloprop[d]indolo[2,1-a][2]benzazepine-1a,5(2H)-dicarboxamide, 8-cyclohexyl-$N^5$-[(dimethylamino)sulfonyl]-1,12b-dihydro-$N^{1a}$-[(2R,3S)-3-hydroxy-4,7,7-trimethylbicyclo[2.2.1]hept-2-yl]-11-methoxy-, (1aR)-[partial]- under the HPLC conditions described above. Product obtained as a light yellow solid, 215 mg, 34% yield). MS m/703(MH+), Retention time: 4.038 min. 1H NMR (500 MHz, MeOD) δ ppm 0.20 (m, 0.38H) 0.75 (s, 1.86H) 0.76 (s, 1.86H) 0.84 (s, 1.86H) 0.85 (s, 1.14H) 0.89-2.18 (m, 18.9H) 2.52 (m, 0.38H) 2.70 (m, 0.62H) 2.85 (m, 0.38H) 2.97 (m, 0.62H) 3.03 (s, 2.28H) 3.04 (s, 3.72H) 3.33-3.39 (m, 0.62H) 3.43-3.51 (m, 1.24H) 3.73-3.77 (m, 0.38H) 3.78-3.84 (m, 0.38H) 3.90 (s, 1.86H) 3.90 (s, 1.14 H) 4.14 (d, J=14.65 Hz, 0.38H) 5.11 (d, J=14.65 Hz, 0.38H) 5.44 (d, J=15.26 Hz, 0.62H) 6.68 (d, J=4.88 Hz, 0.62H) 6.96-7.03 (m, 1H) 7.07 (d, J=5.19 Hz, 0.38H) 7.12 (d, J=2.44 Hz, 0.38H) 7.23 (d, J=2.14 Hz, 0.62H) 7.27 (d, J=8.54 Hz, 0.62H) 7.33 (d, J=8.54 Hz, 0.38H) 7.55 (dd, J=8.39, 1.68 Hz, 0.62H) 7.62 (dd, J=8.55, 1.53 Hz, 0.38H) 7.87 (d, J=8.54 Hz, 0.62H) 7.91 (d, J=8.55 Hz, 0.38H) 8.08 (d, J=1.22 Hz, 0.38H) 8.10 (d, J=1.22 Hz, 0.62H).

Intermediate 9

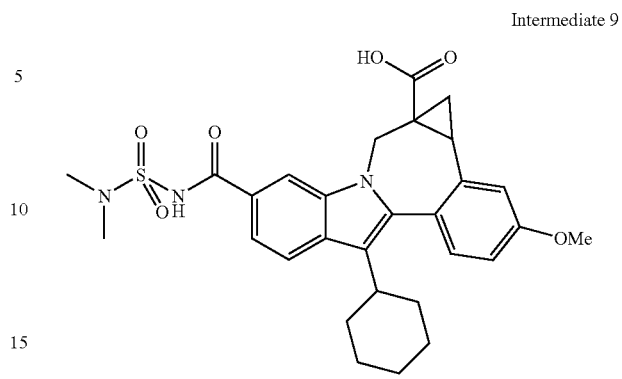

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, (−)-. 10 N NaOH (2.0 mL, 20 mmol) solution and 4 mL of water were added to a solution of cycloprop[d]indolo[2,1-a][2]benzazepine-1a,5(2H)-dicarboxamide, 8-cyclohexyl-$N^5$-[(dimethylamino)sulfonyl]-1,12b-dihydro-$N^{1a}$-[(2R,3S)-3-hydroxy-4,7,7-trimethylbicyclo[2.2.1]hept-2-yl]-11-methoxy-, (1aR)-[partial]-(160 mg, 0.228 mmol) in THF/MeOH (7 mL/7 mL). The reaction mixture was heated at 120° C. under microwave conditions for 1 hr. It was then concentrated, acidified with conc. HCl solution and extracted with ethyl acetate twice (2×30 mL). The organic layers were combined, dried (MgSO4), filtered and concentrated in vacuo to an orange oil. The crude product was then purified by Prep. HPLC column to afford the product a light yellow solid, (80 mg, 64% yield). Average specific rotation −130.85°; Solvent MeOH; Wavelength 589 nm; 50 mm cell. MS m/552(MH+), Retention time: 3.760 min. 1H NMR (500 MHz, MeOD) δ ppm 0.27 (m, 0.38H) 1.14-2.22 (m, 11.62H) 2.76 (m, 0.38H) 2.80-2.92 (m, 1H) 2.92-3.09 (m, 6.62H) 3.45 (d, J=14.95 Hz, 0.62H) 3.90 (s, 1.86H) 3.91 (s, 1.14H) 4.04 (d, J=15.26 Hz, 0.38H) 5.28 (d, J=15.26 Hz, 0.38H) 5.47 (d, J=15.26 Hz, 0.62H) 6.95-7.05 (m, 1H) 7.15 (d, J=2.75 Hz, 0.38H) 7.23 (d, J=1.83 Hz, 0.62H) 7.28 (d, J=8.55 Hz, 0.62H) 7.33 (d, J=8.54 Hz, 0.38H) 7.54 (dd, J=8.39, 1.68 Hz, 0.62H) 7.63 (dd, J=8.55, 1.53 Hz, 0.38H) 7.86 (d, J=8.55 Hz, 0.62H) 7.91 (d, J=8.55 Hz, 0.38H) 8.11 (d, J=1.22 Hz, 0.62H) 8.29 (d, J=1.22 Hz, 0.38H).

Intermediate 13

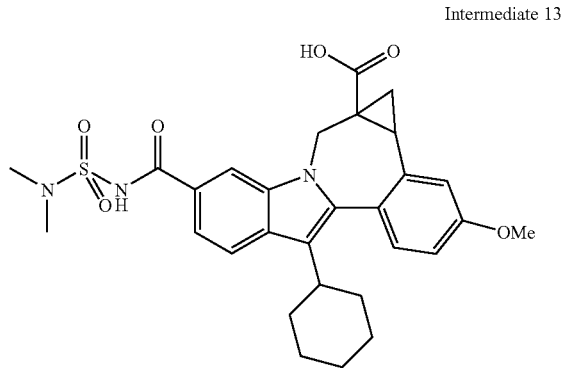

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, (+)-. 10 N NaOH (1.8 mL, 18 mmol) solution and 4 mL of water were added to a solution of cycloprop[d]indolo[2,1-a][2]benzazepine-1a,5(2H)-dicarboxamide, 8-cyclohexyl-$N^5$-[(dimethylamino)sulfonyl]-1,12b-dihydro-$N^{1a}$-[(2R,3S)-3-hydroxy-4,7,7-trimethylbicyclo[2.2.1]hept-2-yl]-11-methoxy-, (1aS)-[partial]-(130 mg, 0.185 mmol) in bTHF/MeOH (7 mL/7 mL). The reaction mixture was heated at 120° C. under microwave conditions for 1 hr. It was concentrated, acidified with conc. HCl solution and extracted with ethyl acetate twice (2×30 mL). The organic layers were combined, dried (MgSO$_4$), filtered and concentrated in vacuo to give an orange oil. The crude product was then purified by Prep. HPLC column to afford the product as a light yellow solid, (68 mg, 67% yield). Average specific rotation +174.73°; Solvent MeOH; Wavelength 589 nm; 50 mm cell MS m/552 (MH$^+$), Retention time: 3.773 min. 1H NMR (500 MHz, MeOD) δ ppm 0.27 (m, 0.38H) 1.14-2.22 (m, 11.62H) 2.76 (m, 0.38H) 2.80-2.92 (m, 1H) 2.92-3.09 (m, 6.62H) 3.45 (d, J=14.95 Hz, 0.62H) 3.90 (s, 1.86H) 3.91 (s, 1.14H) 4.04 (d, J=15.26 Hz, 0.38H) 5.28 (d, J=15.26 Hz, 0.38H) 5.47 (d, J=15.26 Hz, 0.62H) 6.95-7.05 (m, 1H) 7.15 (d, J=2.75 Hz, 0.38H) 7.23 (d, J=1.83 Hz, 0.62H) 7.28 (d, J=8.55 Hz, 0.62H) 7.33 (d, J=8.54 Hz, 0.38H) 7.54 (dd, J=8.39, 1.68 Hz, 0.62H) 7.63 (dd, J=8.55, 1.53 Hz, 0.38H) 7.86 (d, J=8.55 Hz, 0.62H) 7.91 (d, J=8.55 Hz, 0.38H) 8.11 (d, J=1.22 Hz, 0.62H) 8.29 (d, J=1.22 Hz, 0.38H).

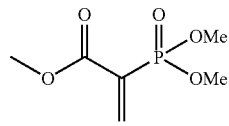

Intermediate 14

2-Propenoic acid, 2-(dimethoxyphosphinyl)-, methyl ester. To a 5 L four necked round bottom flask equipped with a mechanical stirrer, a condenser, a temperature controller and a N2 inlet, was charged paraformaldehyde (40.5 g, 1.35 mol), MeOH (2 L) and piperidine (2 mL). The reaction mixture was heated to reflux under N2 for 3 h. After cooling to 50° C., 2-(dimethoxyphosphoryl)acetate (150 g, 0.824 mol) was added in one portion. The reaction mixture was continued to reflux for 18 h. After cooling to rt, the reaction solution was concentrated in vacuo to give a clear colorless oil. The above oil was dissolved in dry toluene (1 L) in a 3 L four necked round bottom flask equipped a temperature controller, a N$_2$ inlet, a magnetic stirrer and a Dean-Stark apparatus. To the solution was added TsOH.H$_2$O (5.2 g). The reaction mixture was then refluxed azeotropically to remove methanol for 18 h. After cooling to rt, the solution was concentrated in vacuo to give a yellow oil which was vacuum distilled at 150-155° C./0.2 mmHg to afford the product as a colorless oil (135.0 g). Purity, 90% based on 1H NMR. $^1$H NMR (CDCl3, 300 MHz) δ 7.0 (dd, J=42.4 and 1.5 Hz, 1H), 6.73 (dd, J=20.5 and 1.8 Hz, 1H), 3.80 (s, 6H), 3.76 (s, 3H).

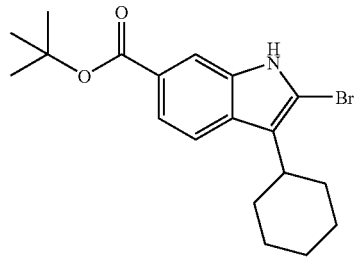

Intermediate 15

1H-Indole-6-carboxylic acid, 2-bromo-3-cyclohexyl-, 1,1-dimethylethyl ester. To a mechanically stirred solution of 2-bromo-3-cyclohexyl-1H-indole-6-carboxylic acid (80 g, 0.24 m) in dry methylene dichloride(1.2 L) and THF (100 mL) were added activated molecular sieves (4A, 80 g) and silver carbonate (275 g, 0.99 m). The reaction mixture was cooled to 0° C. and t-Butyl bromide (142 g, 1.04 m) was added drop wise. The mixture was stirred overnight at rt and monitored by TLC (Hexane-Ethyl acetate 80:20, R$_f$ (Product)= 0.7). If any bromo acid was left unconverted a further 10% of silver carbonate was added and stirring was continued for an addition 2-4 h. On completion, the reaction mixture was filtered through a thin bed of celite. The filtrand was washed with methylene dichloride (500 mL). The combined filtrates were concentrated in-vacuo, and the crude product thus obtained was purified by silica gel chromatography: (230-400 mesh, eluted with a gradient of ethyl acetate in pet ether 0-2%). Homogeneous fractions were combined and evaporated under reduced pressure to give 80 g (85%) of the title compound. HPLC: 90.1% (RT=6.56 min), Column: C18 BDS, (50×4.6 mm), Mobile Phase: Gradient of 0.1% TFA in water: ACN (30→100→30), Flow rate 0.8 mL/min. LCMS: 99.8% (RT=4.44 min), Column: Geneis, C18 50×4.6 mm Mobile Phase: Gradient of 0.1% Formic acid in water : ACN (70→95→70), Flow rate: 0.8 mL/min; M−1=376.5; $^1$H NMR CDCl$_3$) (400 MHz) δ 1.37-1.40 (m, 3H, cyc.Hexyl), 1.62 (s, 9H, t-Bu), 1.80-1.94 (two sets of m, 3H, & 4H respectively, cyc.Hexyl part), 2.81 (m, 1H, CH of cyc.Hexyl-benzylic), 7.70-7.75 (m, 2H, Indole-H$_{4\&5}$), 8.04 (s, 1H, Indole-H$_7$), 8.52 (s, 1H, Indole-NH).

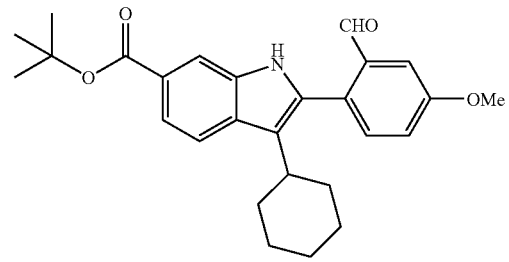

Intermediate 16

1H-Indole-6-carboxylic acid, 3-cyclohexyl-2-(2-formyl-4-methoxyphenyl)-, 1,1-dimethylethyl ester. tert-Butyl 2-bromo-3-cyclohexyl-1H-indole-6-carboxylate (72 g, 0.19 m) was dissolved in a 1:1 mixture of toluene and ethanol (720 mL) and degasified. LiCl (23.9 g, 0.51 m) was then added, followed by sodium carbonate (720 mL, 1.0 M solution degasified separately,) and Pd-tetrakis (13.1 g, 0.011 m).

After stirring for 0.25 h, 2-formyl-4-methoxyphenylboronic acid (41.1 g, 0.22 m) was added and the reaction mixture was heated to 85° C. for 4 h. The reaction was then monitored by TLC, (Hexane-Ethyl acetate 80:20, $R_f$ (Product)=0.55). On completion, the reaction mixture was cooled to rt and water (1.0 L) was added followed by ethyl acetate (1.0 L). The organic layer was washed with brine, and dried and concentrated under vacuum to afford the title compound as a yellow solid. Yield 75 g (74%). HPLC: 99.7% (RT=6.30 min), Column: C18 BDS (4.6×50 mm), SC-307, Mobile Phase: Gradient of 0.1% TFA in water: ACN (30→100→30), Flow rate 0.8 mL/min. LCMS: 98.0% (RT=5.28 min), Column: Geneis, C18 (50×4.6 mm), Mobile Phase: Gradient of 0.1% Formic acid in water: ACN (70→95→70), Flow rate: 0.8 mL/min; M−1=432.2; $^1$H NMR (DMSO-$d_6$) (400 MHz) δ 1.40-1.48 (m, 3H, cyc.Hexyl), 1.57 (s, 9H, t-Bu), 1.84-1.90 (m, 7H, cyc.Hexyl part), 3.09 (m, 1H, CH of cyc.Hexyl-benzylic), 3.84 (s, 3H, OCH$_3$), 6.55 (d, J=4 Hz, 1H, aryl H$_{2'}$), 7.06 (d, 1H, aryl H$_{3'}$), 7.08 (s, 1H, aryl H$_{6'}$), 7.23 (d, 1H, Indole-H$_5$), 7.53 (d, J=8 Hz, 1H, Indole-H$_4$), 7.70-7.75 (m, 2H, NH+Indole-H$_7$), 8.06 (s, 1H, CHO).

Intermediate 17

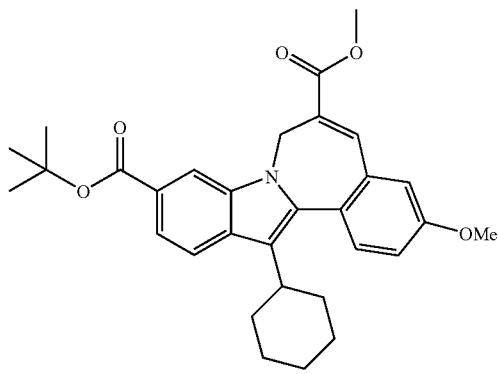

7H-Indolo[2,1-a][2]benzazepine-6,10-dicarboxylic acid, 13-cyclohexyl-, 10-(1,1-dimethylethyl) 6-methyl ester. tert-Butyl 3-cyclohexyl-2-(2-formyl-4-methoxyphenyl)-1H-indole-6-carboxylate (62.5 g, 0.144 m) was dissolved in dry DMF (1.2 L) and stirred mechanically. Cesium carbonate (84 g, 0.17 m) and methyl 2-(dimethoxyphosphoryl)acrylate (65-70% GC pure, 56.2 g, 0.18 m) were then added and the reaction mixture was heated to 65° C. for 4 h, and the reaction was monitored by TLC (Hexane-Ethyl acetate 80:20, $R_f$ (Product)=0.7). On completion, the mixture was cooled to rt, then quenched with water (1.0 L). A yellow solid precipitated, which was collected by filtration and air dried. This material was then slurried in methanol, filtered, and dried under vacuum to give the product as a yellow powder, (70 g, 90%). HPLC: 99.1% (RT=6.45 min), Column: C18 BDS (4.6×50 mm), Mobile Phase: Gradient of 0.1% TFA in water: ACN (30→100→30), Flow rate 0.8 mL/min. LCMS: 100% (RT=7.00 min), Column: Geneis, C18 (50×4.6 mm), Mobile Phase: Gradient of 0.1% Formic acid in water: ACN (70→95→70), Flow rate: 0.8 mL/min; M+1=502.2; $^1$H NMR (CDCl$_3$) (400 MHz) δ 1.10-1.30 (m, 3H, cyc.Hexyl), 1.64 (s, 9H, t-Bu), 1.77-2.07 (m, 7H, cyc.Hexyl part), 2.80 (m, 1H, CH of cyc.Hexyl-benzylic), 3.84 (s, 3H, OCH$_3$), 3.93 (s, 3H, COOCH$_3$), 4.15 & 5.65 (two br.peak., 1H each, allylic CH$_2$), 6.95 (s, 1H, aryl H$_{6'}$), 7.01 (d, 1H, aryl H$_{2'}$), 7.53 (d, J=8 Hz, 1H, aryl H$_{3'}$), 7.70 (d, J=4 Hz, 1H, Indole-H$_5$), 7.84 (s+d, 2H, olefinic H+Indole-H$_4$), 8.24 (s, 1H, indole–H$_7$); $^{13}$C NMR (CDCl$_3$) (100.0 MHz) δ 166.92, 165.71, 158.96, 142.28, 136.47, 13.50, 134.61, 132.43, 132.01, 129.73, 124.78, 124.68, 120.33, 119.39, 119.04, 115.62, 115.05, 111.27, 80.27, 55.49, 52.50, 39.09, 36.81, 33.40, 28.38, 27.15, 26.28.

Intermediate 18

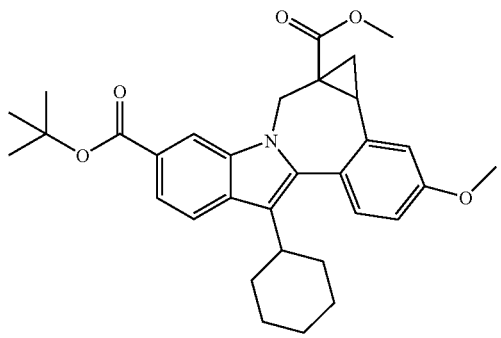

Cycloprop[d]indolo[2,1-a][2]benzazepine-1a,5(2H)-dicarboxylic acid, 8-cyclohexyl-1,12b-dihydro-11-methoxy-, 5-(1,1-dimethylethyl) 1a-methyl ester, (+/−) Sodium hydride (96 mg, 4 mmol) was added to a stirred suspension of trimethylsulfoxonium chloride (567 mg, 4.4 mmol) in anhydrous DMSO (10 mL) under nitrogen. The resultant mixture was stirred at rt for 30-45 min and then neat 7H-indolo[2,1-a][2] benzazepine-6,10-dicarboxylic acid, 13-cyclohexyl-3-methoxy-, 10-(1,1-dimethylethyl) 6-methyl ester (1.0, 2 mmol) was added in small portions. The suspension was diluted with DMSO (5 mL) and heated at 50° C. for 3-4 h. The reaction mixture was allowed to cool to rt and water was added. A solid separated, which was collected by filtration and washed with water and then air dried overnight to afford 1.15 g of crude product. This material was purified by flash column chromatography (silica gel, 3% MeOH in DCM) to provide pure title compound (0.96 g): LC/MS: Retention time 3.816 min; m/e 516 (MH$^+$). $^1$H NMR (400 MHz, CDCl$_3$): The product was observed to exist as inter-converting rotamers, as evidenced from the compound's NMR spectrum.

The following procedure is an example of a method to effect the resolution of racemic cycloprop[d]indolo[2,1-a][2] benzazepine-1a,5(2H)-dicarboxylic acid, 8-cyclohexyl-1, 12b-dihydro-11-methoxy-, 5-(1,1-dimethylethyl) 1a-methyl ester, (+/−). A sample of cycloprop[d]indolo[2,1-a][2]benzazepine-1a,5(2H)-dicarboxylic acid, 8-cyclohexyl-1,12b-dihydro-11-methoxy-, 5-(1,1-dimethylethyl) 1a-methyl ester, (+/−)- was dissolved in a mixture of isopropanol and acetonitrile (8:2) to give a final concentration of 20 mg/mL. This mixture was injected on a preparative chiral SFC chromatography system using the following conditions: Chiralcel OJ-H column, 4.6×250 mm, 5 µm; Mobile Phase: 8% MeOH in CO$_2$; Temp: 35° C.; Flow rate: 2 mL/min for 16 min; UV monitored @ 260 nm; Injection: 5 µL of ~20.0 mg/mL in IPA:ACN (8:2).

Intermediate 19

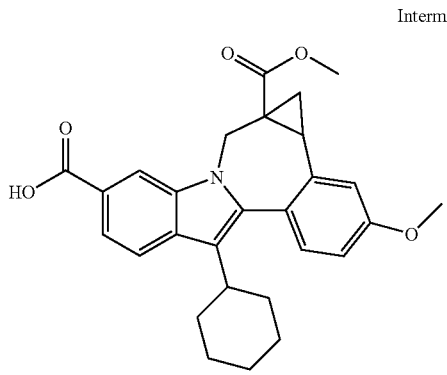

Cycloprop[d]indolo[2,1-a][2]benzazepine-1a,5(2H)-dicarboxylic acid, 8-cyclohexyl-1,12b-dihydro-11-methoxy-, 1a-methyl ester, (+/−)-. TFA (5 mL) was added to a solution of (+/−) 8-Cyclohexyl-1,1a,2,12b-tetrahydro-11-methoxy-1a-(methoxycarbonyl)-cycloprop[d]indolo[2,1-a][2]benzazepine-5-carboxylic acid, tert-butyl ester (515 mg, 1 mmol) in anhydrous DCM (10 mL). The resultant solution was stirred at rt for approximately 8 to 12 hr. The reaction was then evaporated to dryness to afford the title compound (0.47 g, 100%). LC/MS: Retention time 2.245 min; m/e 460 (MH$^+$). $^1$H NMR (400 MHz, CDCl$_3$): From the compounds NMR spectrum, the product was observed to exist as a mixture of interconverting rotamers.

Intermediate 20

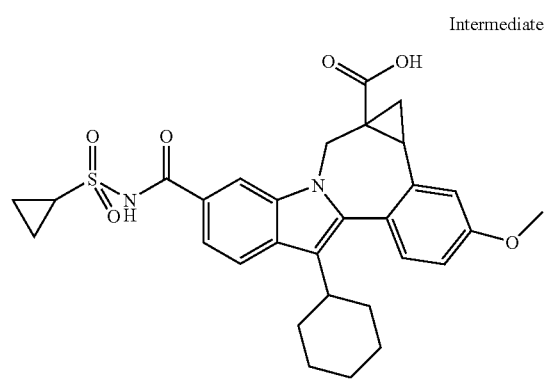

Cycloprop[d]indolo[2,1-a][2]benzazepine-1a(2H)-carboxylic acid, 8-cyclohexyl-5-[[(cyclopropylsulfonyl)amino]carbonyl]-1,12b-dihydro-11-methoxy-, (+/−)-. A mixture of (+/−) 8-cyclohexyl-1,1a,2,12b-tetrahydro-11-methoxy-1a-(methoxycarbonyl)-cycloprop[d]indolo[2,1-a][2]benzazepine-5-carboxylic acid (1 equiv), and carbonyldiimidazole (1.5 equiv) in anhydrous THF was heated at 50° C. for 30 min and allowed to cool to rt. Then 1 equiv of cyclopropanesulfonamide and 1,8-diazabicyclo[5.4.0]undec-7-ene (2 equiv) were added consecutively. The resultant mixture was stirred at rt overnight. After acidic aqueous workup, the isolated crude product was purified by prep. HPLC. The intermediate ester was then hydrolyzed using 1 N NaOH in THF-MeOH to afford the title compound. LC/MS: Retention time: 2.030 min; m/e 549 (MH$^+$). $^1$H NMR (400 MHz, CDCl$_3$): The product was observed to exist as inter-converting rotamers, as evidenced from the compound's NMR spectrum.

Intermediate 21

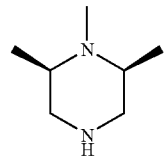

(2R,6S) and (2S,6R)-1,2,6-Trimethylpiperazine. To a solution of cis-3,5-dimethylpiperazine-1-carboxylic acid t-butylester (2.0 g, 9.22 mmol) in MeOH (25 mL), paraformaldehyde (0.84 g, 28 mmol) and zinc chloride (3.83 g, 28 mmol) were added. Then sodium cyanoborohydride (1.76 g, 28 mmol) was added in portions. The reaction mixture was stirred at rt. for 4 hr. Then insoluble solid was filtered out and the filtrated was concentrated. The residue was participated between saturated NaHCO$_3$ solution and CH$_2$Cl$_2$ (2×50 mL). The organic layers were combined, dried (MgSO$_4$) and concentrated to give a colorless oil. It was then dissolved in CH$_2$Cl$_2$ (10 mL) and TFA (2.5 mL) was added. The reaction mixture was stirred at rt. for overnight. TFA and solvent were evaporated to give a white solid as final product as TFA salt. (2.6 g, 86% yield); MS m/129(MH$^+$). 1H NMR (500 MHz, CHLOROFORM-D) δ ppm 1.41 (d, J=6.41 Hz, 6H) 2.87 (s, 3H) 3.38-3.56 (m, 4 H) 3.71-3.90 (m, 2H).

Intermediate 22

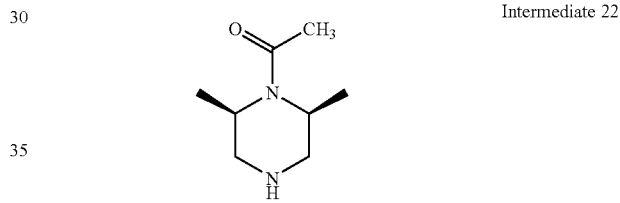

(2S,6R) and (2R,6S)-1-(-2,6-Dimethylpiperazin-1-yl)ethanone. To a solution of cis-3,5-dimethylpiperazine-1-carboxylic acid t-butylester (1.0 g, 4.666 mmol) in CH$_2$Cl$_2$ (10 mL), TEA (0.715 mL, 5.133 mmol) and acetyl chloride (0.364 mL, 5.133 mmol) were added. The reaction mixture was stirred at rt. for 2 hr. Then it was quenched with water and acidified with 1N HCl solution. Extracted with CH$_2$Cl$_2$ (2× 50 mL) and the organic layers were combined, dried (MgSO$_4$) and concentrated to give a yellowish solid. It was then dissolved in CH$_2$Cl$_2$ (10 mL) and TFA (2 mL) was added. The reaction mixture was stirred at rt. for 3 hr. TFA and solvent were evaporated to give a yellowish thick oil as final product as TFA salt. (1.1 g, 93% yield). MS m/z 157(MH$^+$), Retention time: 0.208 min. 1H NMR (500 MHz, CHLOROFORM-D) δ ppm 1.38 (d, J=7.02 Hz, 6H) 2.09 (s, 3H) 3.06 (dd, J=12.97, 5.04 Hz, 2H) 3.25 (d, J=13.43 Hz, 2H) 4.27-4.73 (m, 2H).

Intermediate 23

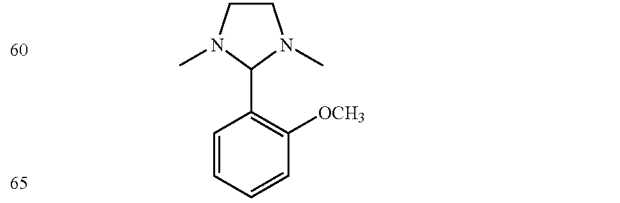

2-(2-methoxyphenyl)-1,3-dimethylimidazolidine. A solution of o-anisaldehyde (9.0 g, 66 mmol) and N,N'-dimethylethylenediamine (7.9 mL, 73 mmol) in ethanol (180 mL) was stirred at r.t. for overnight. MgSO₄ (30 g) was added and the mixture was stirred for 20 min. The reaction mixture was filtered and washed with ether. The solvent was removed in vacuo to afford 2-(2-methoxyphenyl)-1,3-dimethylimidazolidine as a light yellow solid, 12 g, yield 88%. 1H NMR (500 MHz, CHLOROFORM-D) δ ppm 2.21 (s, 6H) 2.57-2.72 (m, 2H) 3.34 (d, J=2.75 Hz, 2H) 3.82 (s, 3H) 4.13 (s, 1H) 6.88 (d, J=8.24 Hz, 1H) 7.00 (t, J=7.48 Hz, 1H) 7.25-7.30 (m, 1H) 7.67 (d, J=7.63 Hz, 1H).

Intermediate 24

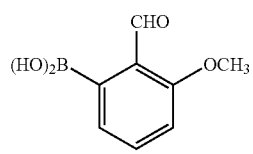

3-methoxy-2-formylphenylboronic acid. A solution of t-butyl lithium (9.0 mL, 1.7 M in pentane) was added to a stirred solution of 2-(2-methoxyphenyl)-1,3-dimethylimidazolidine (2.0 g, 9.8 mmol) in THF (5 mL) at −10° C. under N₂ and stirred at 0-5° C. for 2 hours. The reaction mixture was cooled to −50° C. and triisopropylborate (3.5 mL, 15 mmol) was added. The solution was slowly warmed to 0° C. in 3 hrs. HCl (120 mL of 2N) was added at 0° C. and let it stirred for 30 min. The mixture was warmed to room temperature and was diluted with ethyl acetate. The organic layer was washed ( 2× HCl (1 N), brine), dried ( sodium sulfate) and concentrated to afford yellow crude product which purified by reverse phase HPLC chromatography. Upon removal of solvent 3-methoxy-2-formylphenylboronic acid crystallized as a light yellow solid, 1.3 g (yield 75%). ESI-MS m/e 177 (MH⁺).

Intermediate 25

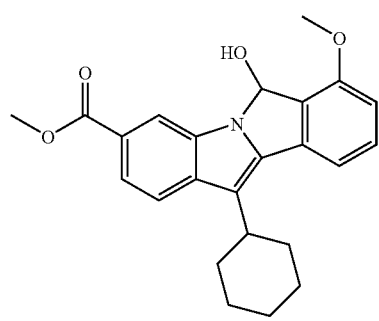

Methyl 11-cyclohexyl-6-hydroxy-7-methoxy-6H-isoindolo[2,1,-a]indole-3-carboxylate. A stirred mixture of methyl 2-Bromo-3-cyclohexyl-1H-indole-6-carboxylate (1.27 g, 7.0 mmol), 3-methoxy-2-formylphenylboronic acid (2.37 g, 7.0 mmol), LiCl (1.18 g, 28 mmol) and Pd(PPh₃)₄ (200 mg, 0.17 mmol) in 1M Na₂CO₃ (25 mL, 25 mmol) and 1:1 ethaol-toluene (100 mL). The reaction mixture was heated under nitrogen at 80° C. for overnight. The reaction mixture was then diluted with ethyl acetate and water, and then acidified with an excess of dilute HCl (1N). The ethyl acetate layer was then collected and washed with water, brine and then dried (NaSO₄). Evaporation of solvents afforded crude product which was triturated with DCM and hexanes to provide the title compound as a white solid, (1.9 g, 68% yield). LC-MS: m/e 390 (M–H)⁻; 374( M–H)⁺.

Intermediate 26

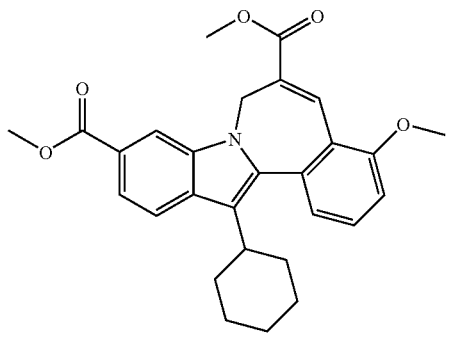

Dimethyl 13-cyclohexyl-4-methoxy-7H-indolo[2,1,-a][2] benzazepine-6,10-dicarboxylate. A stirred suspension of Methyl 11-cyclohexyl-6-hydroxy-7-methoxy-6H-isoindolo [2,1,-a]indole-3-carboxylate (1.9 g, 4.9 mmol), cesium carbonate (2.4 g, 7.3 mmol) and trimethyl 2-phosphonoacetate (1.4 g, 7.3 mmol) in an.DMF (10 mL) was heated at 65° C. for 20 hr. The mixture was poured into ice-water and acidified with dilute HCl to precipitate the crude product. The solid was collected, dried and purified by Biotage chromatograph system eluent with ethyl acetate and Hexanes (1:6). Homogeneous fractions were combined and to afford the designated compound as a pale yellow solid (2.0 g, 89% yield). MS m/z 460 (MH⁺), ¹H NMR (500 MHz, CHLOROFORM-D) δ ppm 1.12-2.21 (m, 10H) 2.85-2.94 (m, 1H) 3.82 (s, 3H) 3.92-3.99 (m, 6H) 4.20 (d, J=14.65 Hz, 1H) 5.70 (d, J=14.65 Hz, 1H) 6.97-7.05 (m, 1H) 7.19 (d, J=7.63 Hz, 1H) 7.49 (t, J=7.93 Hz, 1H) 7.72-7.79 (m, 1H) 7.84-7.91 (m, 1H) 8.12 (s, 1H) 8.31 (s, 1H).

Intermediate 27

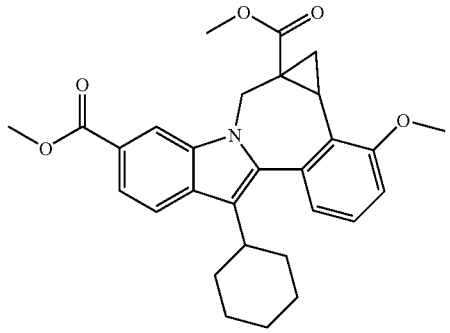

Dimethyl 8-cyclohexyl-12-methoxy-1,12b-dihydrocyclopropa[d]indolo[2,1-a][2]benzazepine-1a,5(2H)-dicarboxylate. DMSO (5 mL) was added to a mixture of trimethylsulfoxonium iodide (660 mg, 3.0 mmol) and NaH (120 mg in 60% oil dispersion, 3.0 mmol) in a round-bottomed flask. Thereaction mixture was stirred at r.t. for 0.5 hr. Dimethyl 13-cyclohexyl-4-methoxy-7H-indolo[2,1,-a][2]benzazepine-6,10-dicarboxylate (460 mg, 1.0 mmol) was then added and the reaction mixture was stirred at rt. for 3 hr. The reaction was then quenched with water and acidified with 1N HCl solution. The crude product then precipitated as a light yellow solid which was collected by filtration and air dried, (470 mg, 99% yield). 10 mg of this material was then purified by Prep. HPLC to afford the title compound as a light yellow solid (7 mg). MS m/z 474 (MH+), $^{1}$H NMR (500 MHz, CHLOROFORM-D) δ ppm 0.26-0.33 (m, 0.25H) 1.00-1.07 (m, 0.75H) 1.12-2.62 (m, 12H) 2.76-2.86 (m, 0.25H) 2.87-2.97 (m, 0.75H) 3.44-3.57 (m, 3H) 3.92-3.99 (m, 6H) 4.01-4.16 (m, 1H) 5.14-5.23 (m, 0.25H) 5.39-5.48 (m, 0.75H) 6.91-7.02 (m, 2H) 7.27-7.40 (m, 1H) 7.67-7.73 (m, 0.75H) 7.73-7.79 (m, 0.25H) 7.80-7.88 (m, 1H) 8.12-8.16 (m, 0.25H) 8.34-8.39 (m, 0.75H).

Intermediate 28

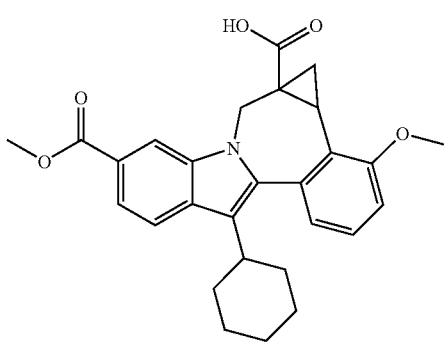

8-Cyclohexyl-12-methoxy-5-(methoxycarbonyl)-1,12b-dihydrocyclopropa[d]indolo[2,1-a][2]benzazepine-1a(2H)-carboxylic acid. A 1N NaOH solution (5.0 mL) was added to a solution of dimethyl 8-cyclohexyl-12-methoxy-1,12b-dihydrocyclopropa[d]indolo[2,1-a][2]benzazepine-1a,5(2H)-dicarboxylate (470 mg, 1.0 mmol) in a THF/Methanol mixture (10 mL/10 mL) and let it shaked at r.t. for 10 hrs. The pH was adjusted to 4-5 using 1N HCl solution. The resultant mixture was then extracted with ethyl acetate and the organic layer was dried (NaSO$_4$), filtered and concentrated in vacuo. The crude was then purified by Prep. Reverse phase HPLC to afford the pure title compound as a light yellow solid (230 mg, 50% yield). MS m/z 460 (MH+), $^{1}$H NMR (500 MHz, CHLOROFORM-D) δ ppm 0.25-0.41 (m, 0.35H) 1.02-1.14 (m, 0.63H) 1.14-2.72 (m, 12H) 2.75-2.88 (m, 0.35H) 2.86-2.99 (m, 0.65H) 3.89-3.99 (m, 6H) 4.00-4.16 (m, 1H) 5.10-5.22 (m, 0.35H) 5.35-5.48 (m, 0.65H) 6.88-7.04 (m, 2H) 7.27-7.41 (m, 1H) 7.66-7.90 (m, 2H) 8.08-8.16 (m, 0.35H) 8.30-8.39 (m, 0.65H).

Intermediate 29

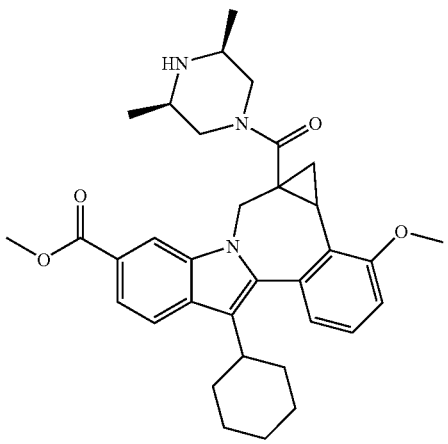

Methyl 8-cyclohexyl-1a[[[3R,5S]-3,5-dimethyl-1-piperizinyl]carbonyl]-12-methoxy-1,1a,2,12b-tetrahydrocyclopropa[d]indolo[2,1,-a][2]benzazepine-5-carboxylate. To the 8-cyclohexyl-12-methoxy-5-(methoxycarbonyl)-1,12b-dihydrocyclopropa [d]indolo[2,1-a][2]benzazepine-1a(2H)-carboxylic acid(70 mg, 0.15 mmol) in 1.0 mL of an. DMF in a 3 dram vial equipped with a Teflon lined screw cap was added DIPEA (0.1 mL, 0.57 mmol), 2-(1H-Benzotriazole-1-yl)-1,1,3,3,-Tetramethyluronium Tetrafluoroborate (TBTU, 67 mg, 0.21 mmol) followed by 2,6-dimethyl piperizine (21 mg, 0.18 mmol). The reaction was shaken on an Innova 2000 orbital shaker at 240 rpm overnight at room temperature. The reaction solution was filtered and purified by Prep HPLC (Acetonitrile/water with TFA buffer) to yield the title compound as yellow solid (70 mg, 85% yield). MS m/e 556 (MH+).

Intermediate 30

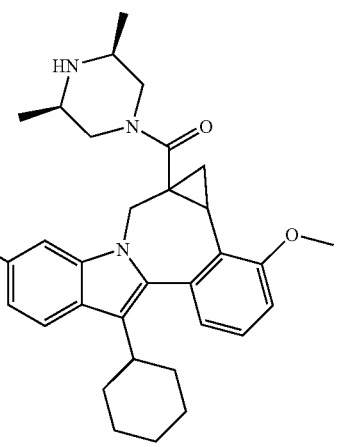

8-Cyclohexyl-1a[[[3R,5S]-3,5-dimethyl-1-piperizinyl]carbonyl]-12-methoxy-1,1a,2,12b-tetrahydrocyclopropa[d]indolo[2,1,-a][2]benzazepine-5-carboxylic acid A 1N NaOH solution (2.0 mL) was added to a solution of Methyl 8-cyclohexyl-1a[[[3R,5S]-3,5-dimethyl-1-piperizinyl]carbonyl]-12-methoxy-1,1a,2,12b-tetrahydrocyclopropa[d]indolo[2,1,-a][2]benzazepine-5-carboxylate (70 mg, 0.13 mmol) in a THF/Methanol mixture (1 mL/1 mL) and let it shaked at r.t. for 3 hrs. The pH was adjusted to 4-5 using 1N HCl solution.

The resultant mixture was then extracted with ethyl acetate and the organic layer was dried (NaSO$_4$), filtered and concentrated in vacuo. The crude was then purified by Prep. Reverse phase HPLC to afford the pure title compound as a light yellow solid (68 mg, 100% yield). ESI-MS m/e 542 (MH$^+$), $^1$H NMR (500 MHz, CD$_3$OD) δ ppm 1H 1.06-2.41 (m, 20H) 2.97-3.09 (m, 1H) 3.21-3.79 (m, 6H) 3.94-4.02 (m, 3H) 4.91-4.99 (m, 0.2H) 5.07-5.16 (m, 0.8H) 7.01-7.08 (m, 1H) 7.12-7.18 (m, 0.8H) 7.20-7.26 (m, 0.2H) 7.38-7.52 (m, 1H) 7.71-7.81 (m, 1H) 7.88-7.96 (m, 1H) 8.06-8.10 (m, 0.8H) 8.19-8.24 (m, 0.2H).

Intermediate 31

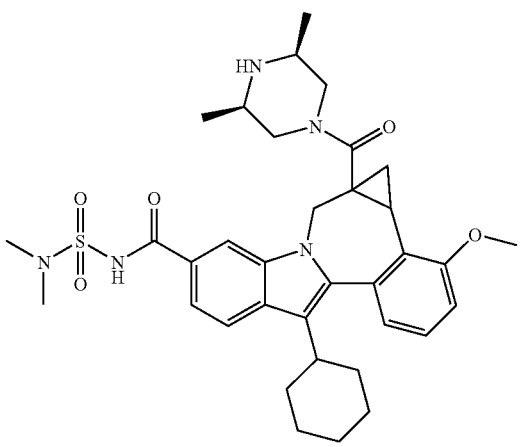

(+/−)8-cyclohexyl-1a[[[3R,5S]-3,5-dimethyl-1-piperizinyl]carbonyl]-N-(dimethylsulfamoyl)-12-methoxy-1,1a,2,12b-tetrahydrocyclopropa[d]indolo[2,1,-a][2]benzazepine-5-carboxamide A mixture of 8-cyclohexyl-1a[[[3R,5S]-3,5-dimethyl-1-piperizinyl]carbonyl]-12-methoxy-1,1a,2,12b-tetrahydrocyclopropa[d]indolo[2,1,-a][2]benzazepine-5-carboxylic acid (54 mg, 0.1 mmol), and carbonyldiimidazole (49 mg, 0.3 mmol) in anhydrous THF was heated at 60° C. for 1 hr and allowed to cool to rt. Then N,N-dimethylsulfonamide (37 mg, 0.3 mmol) and 1,8-diazabicyclo[5.4.0]undec-7-ene (46 mg, 0.3 mmol) were added consecutively. The resultant mixture was heated at 60° C. for 2 hr. After acidic aqueous workup, the isolated crude product was purified by Prep HPLC to afford the title compound as light yellow solid (39 mg, 60%). MS m/z 648 (MH$^+$), $^1$H NMR (500 MHz, CD$_3$OD) δ ppm 1.05-1.59 (m, 12H) 1.69-1.88 (m, 3H) 1.91-2.17 (m, 4.2H) 2.27-2.35 (m, 0.8H) 2.51-2.64 (m, 1H) 3.01-3.07 (m, 6H) 3.10-3.63 (m, 4.2H) 3.71-3.78 (m, 0.8H) 3.94-3.98 (m, 2.4H) 3.98-4.02 (m, 0.6H) 4.13-4.19 (m, 0.2H) 4.25-4.37 (m, 0.8H) 4.90-4.97 (m, 0.2H) 5.08-5.15 (m, 0.8H) 7.01-7.09 (m, 1H) 7.12-7.18 (m, 0.8H) 7.22-7.27 (m, 0.2H) 7.41-7.51 (m, 1H) 7.56-7.62 (m, 0.8H) 7.63-7.67 (m, 0.2H) 7.89-7.98 (m, 1H) 7.99-8.03 (m, 0.8H) 8.07-8.13 (m, 0.2H).

Intermediate 32

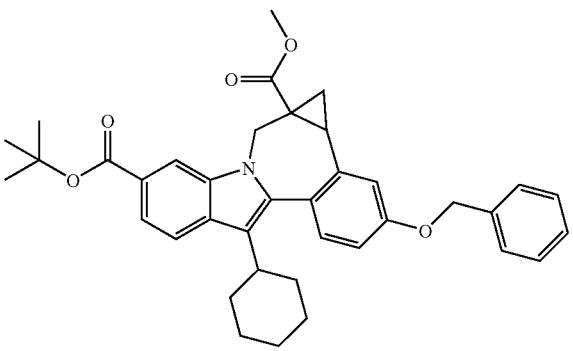

5-Tert-butyl 1a-methyl 11-(benzyloxy)-8-cyclohexyl-1,12b-dihydrocyclopropa[d]indolo[2,1-a][2]benzazepine-1a,5(2H)-dicarboxylate. Trimethylsulfoxonium iodide (8.51 g, 38.7 mMol) was suspended in 100 ml of anhydrous DMSO and placed under a blanket of nitrogen atmosphere. Sodium hydride, 95% (937 mg, 37.1 mMol) was added to the reaction. The reaction was stirred for approximately 30 minutes under a nitrogen atmosphere until the reaction mixture was clear and homogenous. 10-tert-butyl 6-methyl 3-(benzyloxy)-13-cyclohexyl-7H-indolo[2,1-a][2]benzazepine-6,10-dicarboxylate (10.63 g, 18.4 mMol) was added to the reaction and the reaction was heated a nitrogen atmosphere at 65 C for 18 hr.

The reaction was cooled and partitioned between dichloromethane and 1N aqueous hydrochloric acid. The aqueous phase was extracted with dichloromethane and the organic phases combined and washed with 1N aqueous hydrochloric acid and dried over sodium sulfate. Crude product (11.17 g) as a brown foam was obtained and purified by silica gel chromatography eluting with dichloromethane to yield 9.3 g of the title compound as a light orange foam. $^1$H NMR (500 MHz, CHLOROFORM-D) δ ppm 0.40 (t, J=6.10 Hz, 0.5H) 1.09-1.31 (m, 2.1H) 1.32-1.48 (m, 2.8H) 1.48-1.61 (m, 2.1H) 1.61-1.66 (m, 9.0H) 1.66-1.85 (m, 3.5H) 1.86-2.18 (m, 4.3H) 2.63 (t, J=8.39 Hz, 0.5H) 2.78 (s, 0.5H) 2.84-2.97 (m, 1.1H) 3.42 (d, J=14.95 Hz, 0.5H) 3.49-3.63 (m, 1.5H) 3.73-3.86 (m, 1.4H) 4.06 (d, J=15.26 Hz, 0.5H) 5.06-5.24 (m, 2.6H) 5.42 (d, J=14.95 Hz, 0.5H) 6.93-7.04 (m, 1.0H) 7.10 (s, 0.5H) 7.22 (s, 0.6H) 7.26-7.31 (m, 0.9H) 7.31-7.39 (m, 1.1H) 7.39-7.53 (m, 4.2H) 7.68 (dd, J=20.29, 8.39 Hz, 1.1H) 7.80 (t, J=8.39 Hz, 1.0H) 8.02-8.13 (m, 0.5H) 8.18-8.32 (m, 0.5H). HPLC analysis: Shimadzu Analytical HPLC using Discovery VP software: % A=10% methanol, 90% water, 0.1% trifluoroacetic acid; % B=90% methanol, 10% water, 0.1% trifluoroacetic acid; Initial % B=50; Final % B=100; Gradient=5 min; Runtime=7 min; Flow rate=5 ml/min; Wavelength=220 nm; Column=Phenomenex Luna 3.0 mm×50 mm S10; Retention Time=5.17 min, purity 99%; Flow injection Mass Spectrometry: MS m/z 592(MH$^+$).

Intermediate 33

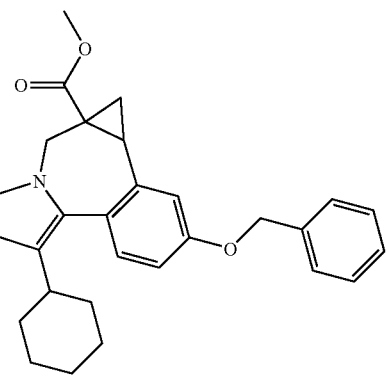

11-(benzyloxy)-8-cyclohexyl-1a-(methoxycarbonyl)-1,1a,2,12b-tetrahydrocyclopropa[d]indolo[2,1-a][2]benzazepine-5-carboxylic acid. 5-Tert-butyl 1a-methyl 11-(benzyloxy)-8-cyclohexyl-1,12b-dihydrocyclopropa[d]indolo[2,1-a][2]benzazepine-1a,5(2H)-dicarboxylate (3.0 g, 5.1 mMol) was dissolved in 1,2-dichloroethane (50 mL) and trifluoroacetic acid (50 mL) was added over a 5 minutes to the reaction using an addition funnel. The reaction was stirred for 1.25 hrs at room temperature. Reaction volatiles were removed in vacuuo and benzene was repeatedly added and subsequently removed in vacuuo to aid in the removal of trace trifluoroacetic acid. The title compound was isolated (2.82 g) as an amorphous off-white solid. $^1$H NMR (500 MHz, CHLOROFORM-D) δ ppm 0.43 (t, J=6.26 Hz, 0.4H) 1.06-1.16 (m, 0.3H) 1.18-1.33 (m, 2.4H) 1.33-1.50 (m, 2.7H) 1.58 (d, J=13.12 Hz, 0.5H) 1.65-1.72 (m, 0.7H) 1.71-1.85 (m, 2.7H) 1.93 (d, J=7.63 Hz, 1.3H) 1.96-2.18 (m, 2.9H) 2.61-2.70 (m, 0.4H) 2.80 (t, J=12.21 Hz, 0.5H) 2.86-2.99 (m, 1.2H) 3.45 (d, J=15.26 Hz, 0.6H) 3.53-3.64 (m, 1.8H) 3.76-3.86 (m, 1.1H) 4.10 (d, J=15.26 Hz, 0.4H) 5.09-5.19 (m, 2.0H) 5.22 (d, J=15.26 Hz, 0.4H) 5.38-5.51 (m, 0.6H) 6.95-7.05 (m, 1.0H) 7.11 (d, J=2.14 Hz, 0.4H) 7.22-7.26 (m, 0.7H) 7.26-7.31 (m, 1.1H) 7.33-7.40 (m, 1.2H) 7.43 (m, 2.1H) 7.44-7.50 (m, 2.1H) 7.72-7.93 (m, 2.0H) 8.21 (s, 0.4H) 8.37-8.50 (m, 0.6H). HPLC analysis: Shimadzu Analytical HPLC using Discovery VP software: % A=10% methanol, 90% water, 0.1% trifluoroacetic acid; % B=90% methanol, 10% water, 0.1% trifluoroacetic acid; Initial % B=50; Final % B=100; Gradient=5 min; Runtime=6 min; Flow rate=5 ml/min; Wavelength=220 nm; Column=Phenomenex Luna 3.0 mm×50 mm S10; Retention Time=4.32, purity 97%; Flow injection Mass Spectrometry: MS m/z 536(MH$^+$), m/z 534(MH$^-$).

sodium sulfate and volatiles removed in vacuuo to yield 3.85 g of a yellow amorphous foam. Proton NMR in deuterochloroform revealed approximate 0.8 mole equivalent of dimethylsulfamide(δ ppm=2.8) the reaction product. The product was dissolved in approximately 200 mL of dichloromethane and washed 1× with 1N aqueous hydrochloric acid and 3× with 0.1N aqueous hydrochloric acid. The total volume of aqueous washings for this manipulation was approximately 1000 mL. The organic phase was dried over sodium sulfate and solvent removed in vacuuo to yield 3.21 g of a yellow amorphous solid. $^1$H NMR (500 MHz, CHLOROFORM-D) δ ppm 0.33-0.41 (m, 0.3H) 1.08 (m, 0.2 H) 1.18-1.33 (m, 2.6H) 1.33-1.47 (m, 3.3H) 1.57 (d, J=12.21 Hz, 0.8H) 1.65-1.83 (m, 4.4H) 1.89-2.12 (m, 4.8H) 2.64 (dd, J=10.22, 6.87 Hz, 0.5H) 2.74-2.83 (m, 0.6H) 2.84-2.97 (m, 1.4H) 3.08 (s, 6.0H) 3.43 (d, J=14.95 Hz, 0.7H) 3.53-3.56 (m, 1.6H) 3.81 (s, 1.3H) 4.09 (d, J=15.26 Hz, 0.5H) 5.08-5.21 (m, 2.7H) 5.40 (d, J=14.65 Hz, 0.6H) 6.94-7.04 (m, 1.2H) 7.11 (d, J=2.44 Hz, 0.5H) 7.20-7.25 (m, 0.8H) 7.26-7.29 (m, 0.9H) 7.32-7.52 (m, 6.9H) 7.80-7.90 (m, 1.1H) 7.97 (s, 0.5H) 8.20 (s, 0.6H) 8.51 (d, J=22.58 Hz, 1.0H). HPLC analysis: Shimadzu Analytical HPLC using Discovery VP software: % A=10% methanol, 90% water, 0.1% trifluoroacetic acid; % B=90% methanol, 10% water, 0.1% trifluoroacetic acid; Initial % B=50; Final % B=100; Gradient=5 min; Runtime=6 min; Flow rate=5 ml/min; Wavelength=220 nm; Column=Phenomenex Luna 3.0 mm×50 mm S10; Retention Time=4.06, purity 97%; Flow injection Mass Spectrometry: MS m/z 642(MH$^+$), m/z 640 (MH$^-$).

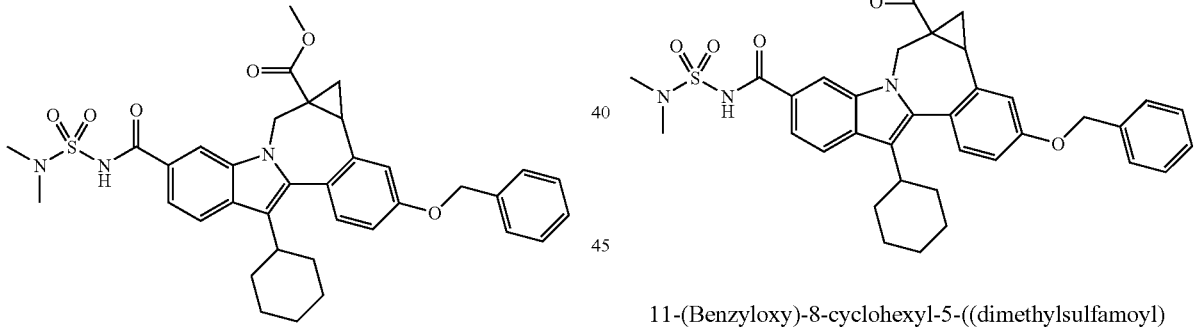

Intermediate 34

Intermediate 35

Methyl 11-(benzyloxy)-8-cyclohexyl-5-((dimethylsulfamoyl)carbamoyl)-1,12b-dihydrocyclopropa[d]indolo[2,1-a][2]benzazepine-1a(2H)-carboxylate. 11-(Benzyloxy)-8-cyclohexyl-1a-(methoxycarbonyl)-1,1a,2,12b-tetrahydrocyclopropa[d]indolo[2,1-a][2]benzazepine-5-carboxylic acid (2.79 g, 5.21 mMol) was suspended in 70 mL of anhydrous THF and carbonyldiimidazole (1.10 g, 6.79 mMol) added to the reaction. The reaction was stirred at room temperature under a nitrogen atmosphere for 1 hr resulting in a transparent homogenous yellow solution. The reaction was heated to reflux under a nitrogen atmosphere for 1 hr then cooled. Dimethylsulfamide (3.30 g, 26.6 mMol) was added to the reaction followed by DBU (856 uL, 5.73 mMol). The reaction was heated to 60-65 C under nitrogen for 20 hrs. The reaction was partitioned between 1N aqueous hydrochloric acid and dichloromethane. The aqueous phase was extracted with dichloromethane. The organic phases were combined and washed 2× with 1N aqueous hydrochloric acid, dried over 11-(Benzyloxy)-8-cyclohexyl-5-((dimethylsulfamoyl)carbamoyl)-1,12b-dihydrocyclopropa[d]indolo[2,1-a][2]benzazepine-1a(2H)-carboxylic acid. Methyl 11-(benzyloxy)-8-cyclohexyl-5-((dimethylsulfamoyl)carbamoyl)-1,12b-dihydrocyclopropa[d]indolo[2,1-a][2]benzazepine-1a (2H)-carboxylate (3.02 g, 4.70 mMol) was dissolved in 24 mL of THF and a 1M solution of tetrabutylammonium hydroxide (24 mL, 24 mMol) in methanol was added to the reaction. The reaction was capped under nitrogen and stirred at room temperature for 18.5 hrs. The reaction was partitioned between 1N aqueous hydrochloric acid and dichloromethane. The aqueous phase was extracted with dichloromethane. The organic washes were combined and washed 2× with 1N aqueous hydrochloric acid, dried over sodium sulfate and solvents removed in vacuuo to yield 3.17 g of a yellow amorphous foam. The material was used without further purification. HPLC analysis: Shimadzu Analytical HPLC using Discovery VP software: % A=10% acetonitrile, 90% water, 0.1% TFA % B=90% acetonitrile, 10% water, 0.1% TFA; Initial % B=50; Final % B=100; Gradient=6 min; Runtime=6 min; Flow rate=4 ml/min; Wavelength=220 nm; Column=Waters Sunfire 4.6 mm×50 mm S5; Retention Time=3.29 min, purity 89%.

Intermediate 36

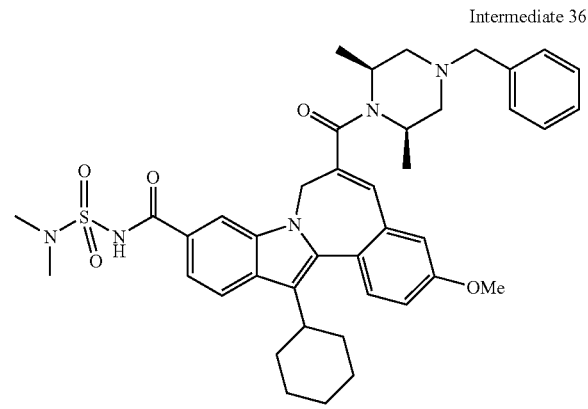

rel-6-(((2R,6S)-4-benzyl-2,6-dimethyl-1-piperazinyl)carbonyl)-13-cyclohexyl-N-((dimethylamino)sulfonyl)-3-methoxy-7H-indolo[2,1-a][2]benzazepine-10-carboxamide. To a stirred solution of 13-cyclohexyl-10-(((dimethylamino)sulfonyl)carbamoyl)-3-methoxy-7H-indolo[2,1-a][2]benzazepine-6-carboxylic acid (200 mg, 0.37 mmol), (3R,5S)-1-benzyl-3,5-dimethylpiperazine (115 mg, 0.56 mmol) and diisopropylethylamine (0.26 mL) in DMF (4 mL) was added HATU (212 mg, 0.56 mmol). The reaction mixture was stirred at rt for 2 h, treated with additional (3R,5S)-1-benzyl-3,5-dimethylpiperazine (100 mg, 0.49 mmol) and stirred at 100° C. for 3 h. The reaction was cooled to rt, diluted with $H_2O$ (30 mL) and 1M HCl (aq.) (1.5 mL) and extracted with EtOAc (20 mL). The organic layer was separated, washed with brine (10 mL), dried ($MsSO_4$), filtered and concentrated. The residue was diluted with MeOH (5 mL) and purified by preparative HPLC ($H_2O/CH_3CN$ with 10 mM $NH_4OAc$ buffer) to yield rel-6-(((2R,6S)-4-benzyl-2,6-dimethyl-1-piperazinyl)carbonyl)-13-cyclohexyl-N-((dimethylamino)sulfonyl)-3-methoxy-7H-indolo[2,1-a][2]benzazepine-10-carboxamide (38 mg, 0.052 mmol, 14%) as an orange solid. $^1$HNMR (300 MHz, $CD_3OD$) δ 1.02-2.22 (m, 20H), 2.58-3.03 (m, 3H), 3.05 (s, 6H), 3.27-3.40 (m, 2H), 3.92 (s, 3H), 4.34-4.56 (m, 1H), 4.99-5.19 (m, 1H), 6.89 (s, 1H) 7.08 (d, J=2.6 Hz, 1H), 7.14 (dd, J=8.8, 2.6 Hz, 1H), 7.19-7.33 (m, 5H), 7.55 (d, J=8.4 Hz, 1H), 7.65 (d, J=8.4 Hz, 1H), 7.90 (d, J=8.4 Hz, 1H), 8.17 (s, 1H). LCMS: m/e 724 $(M+H)^+$, ret time 3.37 min, column B, 4 minute gradient.

Intermediate 37

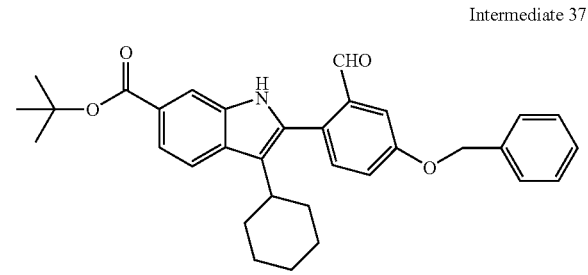

1H-Indole-6-carboxylic acid, 3-cyclohexyl-2-[2-formyl-4-(phenylmethoxy)phenyl]-, 1,1-dimethylethyl ester. tert-Butyl 2-bromo-3-cyclohexyl-1H-indole-6-carboxylate (55 g, 0.145 m) was dissolved in a 1:1 mixture of toluene and ethanol (550 mL) and degasified. LiCl (18.3 g, 0.43 m) was added, followed by Sodium carbonate (550 mL, 1.0 M solution degasified separately,) and Pd-tetrakis (7.7 g, 0.008 m). After stirring for 0.25 h, 4-(benzyloxy)-2-formylphenylboronic acid (44.6 g, 0.17 m) was added and the reaction mixture was heated to 85° C. for 4 h. and monitored by TLC, (Hexane-Ethyl acetate 80:20, $R_f$ (Product)=0.45). On completion the reaction mixture was cooled to rt and water (1.0 L) was added followed by ethyl acetate (1.0 L). The mixture was then stirred for a short period afterwhich the layers separated. The organic layer was collected, washed with brine and then dried over sodium sulfate. The mixture was then filtered and the filtrate was concentrated under vacuum to afford the title compounds as a yellow solid, 60 g (80%). $^1$H NMR (DMSO-$d_6$) (400 MHz) δ 1.40-1.42 (m, 3H, cyc.Hexyl), 1.53 (s, 9H, t-Bu), 1.76-1.82 (m, 7H, cyc.Hexyl part), 3.15 (m, 1H, CH of cyc.Hexyl-benzylic), 5.15 (s, 2H, $OCH_2Ph$), 6.49 (s, 1H, aryl $H_{2'}$), 7.10-7.71 (set of multiplets, 11H, aryl+indole part+NH), 8.01 (s, 1H, CHO).

Intermediate 38

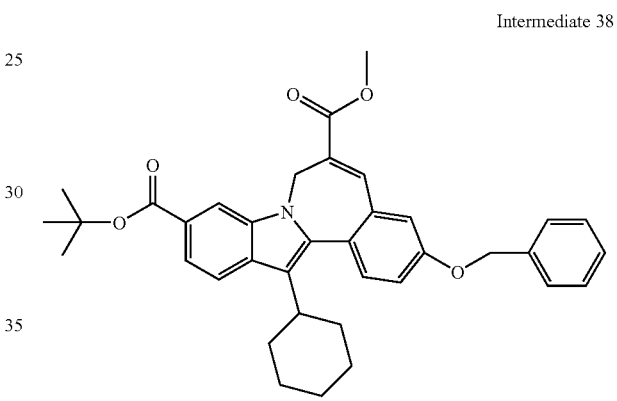

7H-Indolo[2,1-a][2]benzazepine-6,10-dicarboxylic acid, 13-cyclohexyl-3-(phenylmethoxy)-, 10-(1,1-dimethylethyl) 6-methyl ester. 1H-Indole-6-carboxylic acid, 3-cyclohexyl-2-[2-formyl-4-(phenylmethoxy)phenyl]-, 1,1-dimethylethyl ester (32.5 g, 0.06 m) was dissolved in dry DMF (0.7 L) and stirred mechanically. Cesium carbonate (24.8 g, 0.07 m) and 2-propenoic acid, 2-(dimethoxyphosphinyl)-, methyl ester (65-70% GC pure, 37.2 g, 0.19 m) were added and the reaction mixture was heated to 65° C. for 4 h. and the reaction monitored by tlc, (Hexane-Ethyl acetate 80:20, $R_f$(Product)= 0.6). On completion, the mixture was cooled to rt and quenched with water (1.0 L). The separated yellow solid was collected by filtration then dried. Further removal of solvent by slurring in methanol and filtration, followed by air drying gave 35 g of the title compound, (95%). HPLC: 99.7% (Max Chromatogram of (190-400 nm) (RT=7.17 min), Column: C18 BDS (4.6×50 mm), Mobile Phase: Gradient of 0.1% TFA in water : ACN (30→100→30), Flow rate 0.8 mL/min. LCMS : 99.8% (RT=6.90 min), Column: Geneis, C18 (50×4.6 mm), Mobile Phase: Gradient of 0.1% Formic acid in water: ACN (90→95→90), Flow rate: 1.0 mL/min; M+1=578.2. $^1$H NMR ($CDCl_3$) (400 MHz) δ 1.26-1.40 (m, 6H, cyc.Hexyl), 1.66 (s, 9H, t-Bu), 1.78-2.06 (m, 5H, cyc.Hexyl part), 2.80 (m, 1H, CH of cyc.Hexyl-benzylic), 3.87 (s, 3H, $COOCH_3$), 4.30 & 5.40 (two br. peak., 1H each, allylic $CH_2$), 5.18 (s, 2H, $OCH_2Ph$), 7.09 (s, 1H, aryl $H_{6'}$), 7.17-7.86 (sets of multiplets 10H, aryl+indole part) 8.24 (s, 1H, indole-$H_7$). $^{13}$C NMR ($CDCl_3$) (100.0 MHz) δ 166.91, 165.69, 158.20, 142.26, 136.44, 136.40 135.55, 134.64, 132.49, 132.04, 129.74, 128.76, 128.29, 127.56, 125.05, 124.73, 120.38, 119.43, 119.11, 116.42, 115.96, 111.31, 80.27, 70.30, 60.41, 52.52, 39.11, 36.82, 33.42, 32.98, 28.40, 27.17, 26.31, 21.07, 14.23.

EXAMPLE 1

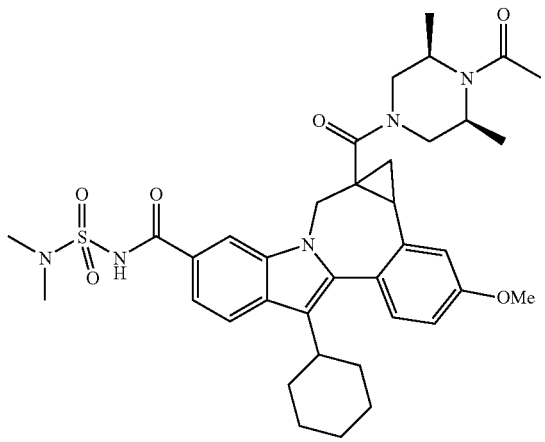

(+/−) Cycloprop[d]indolo[2,1-a][2]benzazepine-5-carboxamide, 1a-[[(3a,5a)-4-acetyl-3,5-dimethyl-1-piperazinyl]carbonyl]-8-cyclohexyl-N-[(dimethylamino)sulfonyl]-1,1a,2,12b-tetrahydro-11-methoxy-, (1aR,12bS)-rel-. MS m/z 690 (MH+), Retention time: 3.661 min. 1H NMR (500 MHz, MeOD) δ ppm 0.22 (m, 0.32H) 1.10-2.19 (m, 20.68H) 2.58 (m, 0.32H) 2.68 (m, 0.68H) 2.79-3.40 (m, 11H) 3.64 (d, J=15.26 Hz, 0.68H) 3.91 (s, 2.04H) 3.93 (s, 0.96H) 4.02-4.24 (m, 2.32H) 4.81-4.85 (m, 0.32H) 5.05 (d, J=15.26 Hz, 0.68H) 7.01-7.06 (m, 1H) 7.19 (d, J=2.44 Hz, 0.32H) 7.22 (d, J=2.75 Hz, 0.68H) 7.33 (d, J=8.54 Hz, 0.68H) 7.35 (d, J=8.55 Hz, 0.32H) 7.56 (d, J=8.55 Hz, 0.68H) 7.64 (d, J=8.55 Hz, 0.32H) 7.85-7.96 (m, 1.68H) 8.15 (s, 0.32H).

EXAMPLE 2

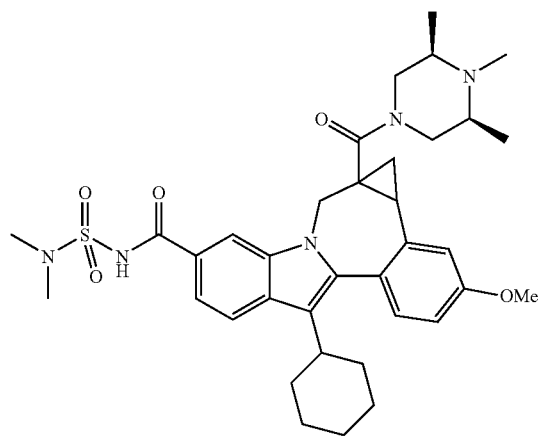

(+/−) Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[(3a,5a)-3,4,5-trimethyl-1-piperazinyl]carbonyl]-. MS m/z 662 (MH+), Retention time: 3.396 min. 1H NMR (500 MHz, MeOD) δ ppm 0.24 (m, 0.28H) 1.13 (m, 0.28H) 1.20-1.64 (m, 10.44H) 1.68-2.18 (m, 7H) 2.57 (m, 0.28H) 2.62 (m, 0.72H) 2.74-3.27 (m, 14H) 3.69 (d, J=15.56 Hz, 0.72H) 3.91 (s, 2.16H) 3.93 (s, 0.84H) 4.06-4.23 (m, 1.28H) 4.38-4.52 (m, 1H) 4.88-4.92 (m, 0.28H) 5.12 (d, J=15.56 Hz, 0.72H) 7.01-7.08 (m, 1H) 7.19 (d, J=2.44 Hz, 0.28H) 7.20 (d, J=2.44 Hz, 0.72H) 7.36 (d, J=8.55 Hz, 0.72H) 7.37 (d, J=8.54 Hz, 0.28H) 7.58 (d, J=8.55 Hz, 0.72H) 7.64 (d, J=8.55 Hz, 0.28H) 7.90 (d, J=8.54 Hz, 0.72H) 7.94 (d, J=8.55 Hz, 0.28H) 8.03 (s, 0.72H) 8.11 (s, 0.28H).

EXAMPLE 3

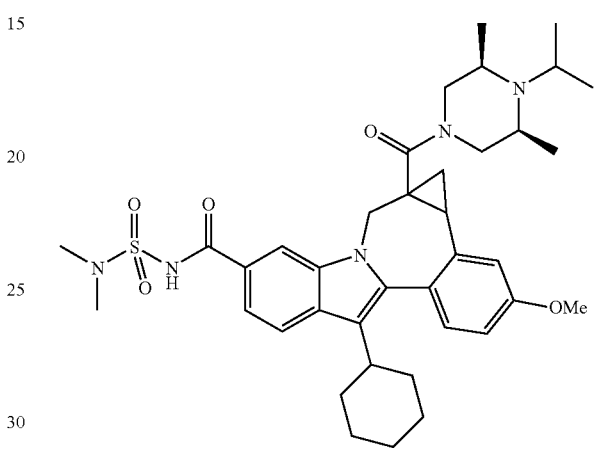

(+/−) Cycloprop[d]indolo[2,1-a][2]benzazepine-5-carboxamide, 8-cyclohexyl-N-[(dimethylamino)sulfonyl]-1a-[[(3a,5a)-3,5-dimethyl-4-(1-methylethyl)-1-piperazinyl]carbonyl]-1,1a,2,12b-tetrahydro-11-methoxy-. MS m/z 690 (MH+), Retention time: 2.493 min. 1H NMR (300 MHz, MeOD) δ ppm 0.25 (m, 0.29H) 1.06-2.22 (m, 23.71H) 2.60 (m, 0.29H) 2.68 (m, 0.71H) 2.77-4.49 (m, 17H) 4.92-4.98 (m, 1.29H) 5.12 (d, J=15.37 Hz, 0.71H) 6.96-7.11 (m, 1H) 7.20 (d, J=2.56 Hz, 1H) 7.35 (d, J=8.42 Hz, 1H) 7.57 (dd, J=8.42, 1.46 Hz, 0.71H) 7.62 (dd, J=8.42, 1.10 Hz, 0.29H) 7.85-7.96 (m, 1H) 7.99 (s, 0.71H) 8.12 (s, 0.29H).

EXAMPLE 4

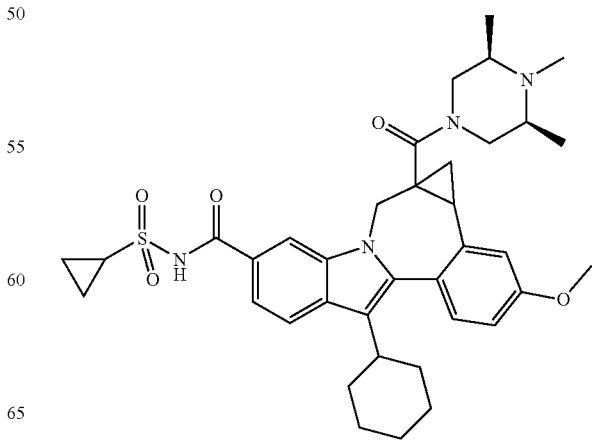

(+/−) 8-cyclohexyl-N-(cyclopropylsulfonyl)-1,1a,2,12b-tetrahydro-11-methoxy-1a-[(3S,5R)-3,4,5-trimethylpiperazine-1-carbonyl]-cycloprop[d]indolo[2,1-a][2]benzazepine-5-carboxamide. LC/MS: Retention time: 1.712 min; m/e 659 (MH+). ¹H NMR (400 MHz, CDCl₃): Compound was observed to exist as inter-converting rotamers, as evidenced from the compound's NMR spectrum.

EXAMPLE 5

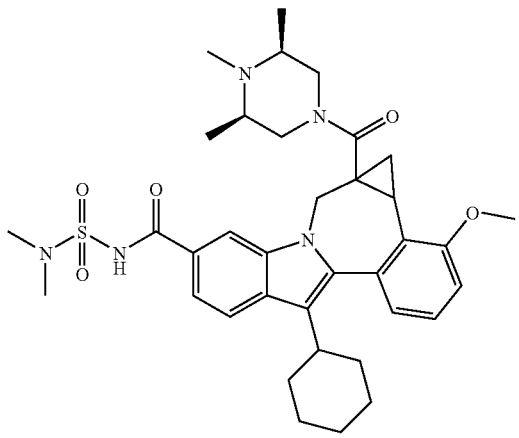

(+/−)8-Cyclohexyl-N-(dimethylsulfamoyl)-12-methoxy-1a[[[3R,5S]-3,4,5-trimethyl-1-piperizinyl]carbonyl]-1,1a,2,12b-tetrahydrocyclopropa[d]indolo[2,1,-a][2]benzazepine-5-carboxamide. To a MeOH solution (2 mL) of (+/−)8-cyclohexyl-1a[[[3R,5S]-3,5-dimethyl-1-piperizinyl] carbonyl]-N-(dimethylsulfamoyl)-12-methoxy-1,1a,2,12b-tetrahydrocyclopropa[d]indolo[2,1,-a][2]benzazepine-5-carboxamide (28 mg, 0.043 mmol), paraformaldhyde (4.0 mg, 0.13 mmol) and zinc chloride (18 mg, 0.13 mmol) were added sodium cyanoborohydride (8.2 mg, 0.13 mmol). The reaction mixture was heated at 60° C. for 0.5 hr. After acidic aqueous workup, the isolated crude product was purified by Prep HPLC to afford the title compound as white solid (22 mg, 77%). MS m/z 662 (MH+), ¹H NMR (500 MHz, CD₃OD) δ ppm 1.02-1.62 (m, 12H) 1.68-1.88 (m, 3H) 1.90-2.17 (m, 4.2H) 2.22-2.34 (m, 0.8H) 2.73-3.61 (m, 8H) 3.03 (s, 6H) 3.73 (d, J=15.26 Hz, 1H) 3.96 (s, 2.4H) 4.00 (s, 0.6H) 4.07-4.20 (m, 0.2H) 4.37-4.47 (m, 0.8H) 4.90-4.97 (m, 0.2H) 5.11 (d, J=15.26 Hz, 0.8H) 6.99-7.09 (m, 1H) 7.15 (d, J=8.55 Hz, 0.8H) 7.24 (d, J=8.55 Hz, 0.2H) 7.39-7.49 (m, 1H) 7.58 (d, J=8.24 Hz, 0.8H) 7.64 (d, J=8.55 Hz, 0.2H) 7.89-7.98 (m, 1H) 8.05 (s, 0.8H) 8.10 (s, 0.2H).

EXAMPLE 6

Rac-11-(benzyloxy)-8-cyclohexyl-N-((dimethylamino)sulfonyl)-1a-(((3R,5S)-3,4,5-trimethyl-1-piperazinyl) carbonyl)-1,1a,2,12b-tetrahydrocyclopropa[d]indolo[2,1-a][2]benzazepine-5-carboxamide. 11-(Benzyloxy)-8-cyclohexyl-5-((dimethylsulfamoyl)carbamoyl)-1,12b-dihydrocyclopropa[d]indolo[2,1-a][2]benzazepine-1a(2H)-carboxylic acid (1.89 g, 3.01 mMol) was dissolved in 30 mL of DMF and TBTU (1.28 g, 3.98 mMol) added. The reaction was stirred under a nitrogen atmosphere at room temperature for 30 minutes then DMAP (1.83 g, 14.98 mMol) dissolved followed by (2R,6S)-1,2,6-trimethylpiperazine bis(trifluoroacetic acid) salt (1.49 g, 4.18 mMol). The reaction was stirred under nitrogen atmosphere at room temperature for 16 hrs. The reaction was poured into 300 mL of water and extract using dichloromethane and dried over sodium sulfate. Solvent was removed in vacuuo to yield 1.79 g of a yellow solid. The crude product was recrystallized from approximately 20 ml of acetonitrile containing 4 ml of water and 1 ml of methanol. Filter off a colorless precipitate and rinse with a small volume of 20% (v/v) water in acetonitrile. Drying the product in vacuuo over phosphorous pentoxide at room temperature yielded 1.35 g (61%) of the title compound. ¹H NMR (500 MHz, CHLOROFORM-D) δ ppm 0.34 (t, J=5.04 Hz, 0.5H) 0.96-1.32 (m, 8.5H) 1.32-1.48 (m, 3.1H) 1.57 (d, J=13.43 Hz, 1.1H) 1.76 (d, J=10.07 Hz, 3.8H) 1.85-2.08 (m, 6.7H) 2.24-2.44 (m, 3.3H) 2.63 (d, J=5.80 Hz, 0.9H) 2.73-2.86 (m, 0.9H) 2.89-3.00 (m, 1.0H) 3.05 (d, J=4.58 Hz, 6.0H) 3.63 (d, J=14.95 Hz, 0.6H) 4.13 (d, J=13.73 Hz, 0.7H) 4.68 (d, J=14.65 Hz, 0.5H) 5.09-5.19 (m, 2.0H) 6.94-7.05 (m, 1.2H) 7.12 (s, 0.6H) 7.20 (t, J=3.20 Hz, 0.6H) 7.26-7.39 (m, 2.4H) 7.39-7.44 (m, 2.4H) 7.44-7.50 (m, 2.4H) 7.83-7.90 (m, 1.0H) 7.95 (br.s, 0.8H). HPLC analysis: Shimadzu Analytical HPLC using Discovery VP software: % A=10% methanol, 90% water, 0.1% trifluoroacetic acid % B=90% methanol, 10% water, 0.1% trifluoroacetic acid; Initial % B=50; Final % B=100; Gradient=5 min; Runtime=6 min; Flow rate=5 ml/min; Wavelength=220 nm; Column=Phenomenex Luna 3.0 mm×50 mm S10; Retention Time=2.70 min, purity 99%; Flow injection Mass Spectrometry: MS m/z 738(MH+), m/z 736(MH−).

EXAMPLE 7

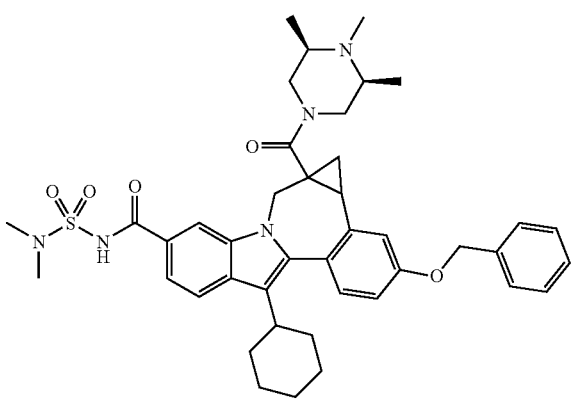

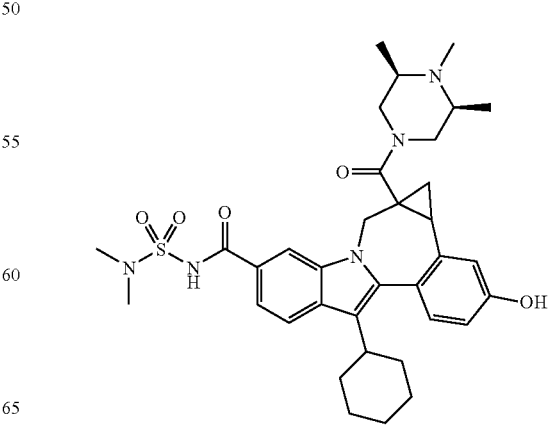

Rac-8-cyclohexyl-N-((dimethylamino)sulfonyl)-11-hydroxy-1a-(((3R,5S)-3,4,5-trimethyl-1-piperazinyl) carbonyl)-1,1a,2,12b-tetrahydrocyclopropa[d]indolo[2,1-a][2]benzazepine-5-carboxamide. Rac-11-(benzyloxy)-8-cyclohexyl-N-((dimethylamino)sulfonyl)-1a-(((3R,5S)-3,4,5-trimethyl-1-piperazinyl)carbonyl)-1,1a,2,12b-tetrahydrocyclopropa[d]indolo[2,1-a][2]benzazepine-5-carboxamide (1.35 g, 1.87 mMol) was dissolved in 75 mL of methanol and 35 mL of THF added. The reaction was placed under a nitrogen atmosphere and 10% palladium on carbon (208 mg) was added. The reaction was placed under a hydrogen atmosphere( 1 atm, balloon) and ther reaction stirred at room temperature for 17 hrs. The reaction was filtered through a celite plug and the celite rinsed with methanol. Volatiles from the filtrate were removed in vacuuo to yield 1.177 g (97%) of a pale yellow slightly green solid. Both proton NMR and HPLC show title compound to exhibit rotomeric species. $^1$H NMR (500 MHz, CHLOROFORM-D) δ ppm 0.35 (br.s, 0.9H) 0.92-1.45 (m, 11.6H) 1.55 (d, J=11.60 Hz, 0.9H) 1.74 (d, J=8.55 Hz, 3.0H) 1.83-2.08 (m, 4.9H) 2.10-2.48 (br. m, 5.1H) 2.50-2.62 (m, 0.9H) 2.77 (t, J=12.05 Hz, 1.2H) 2.84-2.99 (m, 1.3H) 3.03 (d, J=3.66 Hz, 6.0H) 3.57 (d, J=15.26 Hz, 0.4H) 4. 10 (d, J=9.46 Hz, 0.9H) 4.35 (s, 0.5H) 4.65 (d, J=14.34 Hz, 0.6H) 4.98 (s, 0.3H) 6.82 (dd, J=8.24, 1.83 Hz, 0.7H) 6.87 (dd, J=8.24, 2.14 Hz, 0.4H) 6.93-7.08 (m, 1.1H) 7.13 (d, J=8.24 Hz, 0.8H) 7.21 (d, J=8.24 Hz, 0.6H) 7.45 (d, J=8.24 Hz, 1.0H) 7.83 (t, J=8.55 Hz, 1.1H) 7.87-8.08 (br.s, 1.0H). LC-MS analysis: Shimadzu Analytical HPLC using Discovery VP software: % A=10% methanol, 90% water, 0.1% trifluoroacetic acid % B=90% methanol, 10% water, 0.1% trifluoroacetic acid; Initial % B=0; Final % B=100; Gradient=2 min; Runtime=3 min; Flow rate=4 ml/min; Wavelength=220 nm; Column=Phenomenex Luna 3.0 mm×50 mm S10; Retention Time=1.67 min and 1.74 min (rotomers) MS m/z=648(M+H)$^+$.

EXAMPLE 8

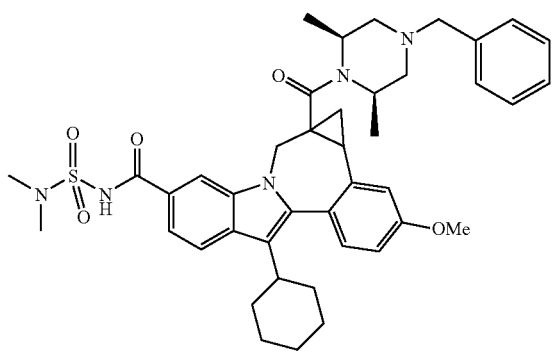

N-(aminosulfonyl)-1a-(rel-6-(((2R,6S)-4-benzyl-2,6-dimethyl-1-piperazinyl)carbonyl))-8-cyclohexyl-11-methoxy-1,1a,2,12b-tetrahydrocyclopropa[d]indolo[2,1-a][2]benzazepine-5-carboxamide. To slurry of sodium hydride (60% dispersion in mineral oil, 10 mg, 0.25 mmol) in DMSO (0.2 mL) stirring under N$_2$ was added trimethylsulfoxonium iodide (50 mg, 0.23 mmol). The reaction mixture was stirred at rt for 30 min and then rel-6-(((2R,6S)-4-benzyl-2,6-dimethyl-1-piperazinyl)carbonyl)-13-cyclohexyl-N-((dimethylamino)sulfonyl)-3-methoxy-7H-indolo[2,1-a][2]benzazepine-10-carboxamide (33 mg, 0.046 mmol) in DMSO (0.5 mL) was added (flask rinsed with DMSO (0.3 mL)). The reaction mixture was stirred 1 h at rt, heated at 100° C. for 2 h and then cooled and neutralized with 1N HCl. The reaction mixture was diluted with MeOH (0.5 mL) and purified by preparative HPLC (H$_2$O/CH$_3$CN with 10 mM NH$_4$OAc buffer) to yield an inseparable mixture of desired product and starting material. The mixture was resubmitted to the reaction conditions described above and heated at 100° C. for 3 h and then cooled. The reaction was concentrated to ~½ volume, diluted with MeOH (1 mL) neutralized with HCl (3 drops) and purified by preparative HPLC (H$_2$O/CH$_3$CN with 10 mM NH$_4$OAc buffer) to yield N-(aminosulfonyl)-1a-(rel-6-(((2R, 6S)-4-benzyl-2,6-dimethyl-1-piperazinyl)carbonyl))-8-cyclohexyl-11-methoxy-1,1a,2,12b-tetrahydrocyclopropa[d]indolo[2,1-a][2]benzazepine-5-carboxamide (9 mg, 0.01, 25%) as a yellow solid. LCMS: m/e 738 (M+H)$^+$, ret time 3.27 min, column B, 4 minute gradient.

EXAMPLE 9

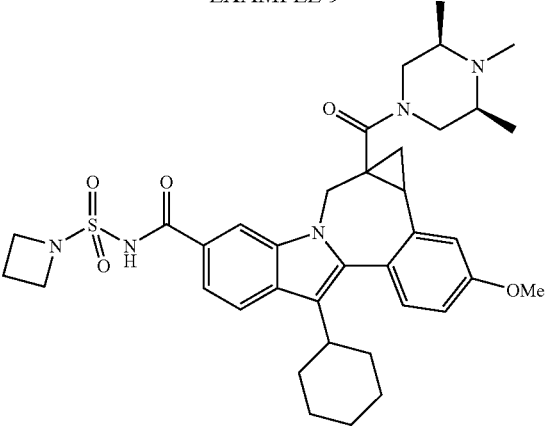

Cycloprop[d]indolo[2,1-a][2]benzazepine-5-carboxamide, N-(1-azetidinylsulfonyl)-8-cyclohexyl-1,1a,2,12b-tetrahydro-11-methoxy-1a-[[(3R,5S)-3,4,5-trimethyl-1-piperazinyl]carbonyl]-. HATU (0.083 mmol, 1.5 eq.) and DIPEA (0.083. 1.5 eq.) were added to a solution of cycloprop[d]indolo[2,1-a][2]benzazepine-1a(2H)-carboxylic acid, 5-[[(1-azetidinylsulfonyl)amino]carbonyl]-8-cyclohexyl-1,12b-dihydro-11-methoxy- (0.055 mmol, 1 eq.) in anhydrous DMF. The mixture was stirred for 2 minutes at room temperature prior to the addition of 1,2,6-trimethylpiperazine (0.083 mmol, 1.5 eq.) The resultant solution was stirred for 14 h and was then fractionated by direct injection onto a reverse phase preparative HPLC. Instrumentation: MassLynx 4.0 SP4 LC-MS software; CTC-Leap HTS-PAL autosampler; Agilent 1100 binary pump; Agilent 1100 photodiode array; Polymer Lab 2100 ELS detector (Evap. Temp.=45° C., Neb. Temp.=35° C.); Waters ZQ with ESCi mass spectrometer; Column: Waters x-Bidge C18 150×4.6 mm 5 micron; Eluant: A=Water, 10 mM NH4OAc; B=ACN: Flow Rate=1 mL/min; Gradient: T=0 min, 90% A: 10% B; T=11 min,5% A: 95% B; T=13 min, 5% A: 195% B; T=13.5 min, 90% A: 10% B. Homogeneous fractions were combined and evaporated to give the title compound. m/e 674.24 (M+H)$^+$, Rt=8.4 min, 92% purity.

EXAMPLE 10

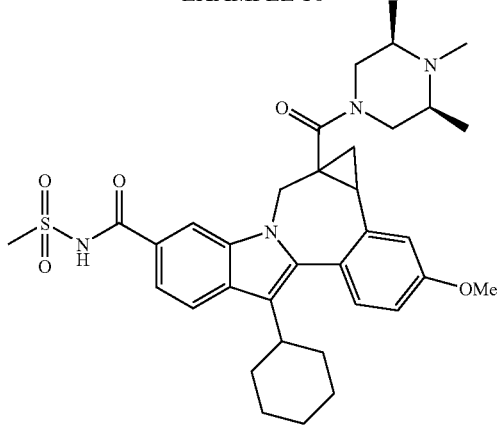

Cycloprop[d]indolo[2,1-a][2]benzazepine-5-carboxamide, 8-cyclohexyl-1,1a,2,12b-tetrahydro-11-methoxy-N-(methylsulfonyl)-1a-[[(3R,5S)-3,4,5-trimethyl-1-piperazinyl]carbonyl]-. HATU (0.083 mmol, 1.5 eq.) and DIPEA (0.083. 1.5 eq.) were added to a solution of cycloprop[d]indolo[2,1-a][2]benzazepine-1a(2H)-carboxylic acid, 8-cyclohexyl-1,12b-dihydro-11-methoxy-5-[[(methylsulfonyl)amino]carbonyl]-(0.055 mmol, 1 eq.) in anhydrous DMF. The mixture was stirred for 2 minutes at room temperature prior to the addition of 1,2,6-trimethylpiperazine (0.083 mmol, 1.5 eq.). The resultant solution was stirred for 14 h and was then fractionated by direct injection onto a reverse phase preparative HPLC. Instrumentation: Masslynx 4.0 SP4; CTC-Leap HTS-PAL autosampler with Harney 4-port injection module; Waters 1525 binary pump; Waters 2488 UV detector; Polymer Lab 1000 ELS detector (Evap. Temp.=90° C., Neb. Temp.=80° C.); Waters LCT mass spectrometer with 4 way MUX source. Column: Waters Xbridge 2.1×50 mm 5 um C18; Eluant: A=5:95 ACN:Water; B=95:5 ACN:Water; Modifier=10 mM NH4OAc; Flow Rate=1 mL/min; Gradient: T=0 min, 100% A: 0% B; T=0.1 min,100% A:0% B; T=2.0 min, 0% A: 100% B; T=3.0 min, 0% A: 100% B; T=3.05 min 100% A: 0% B; T=3.5 min 100% A: 0% B. Homogeneous fractions were combined and evaporated to give the title compound. m/e 620.15 (M+H)$^+$, Rt=8.4 min, 96% purity.

EXAMPLE 11

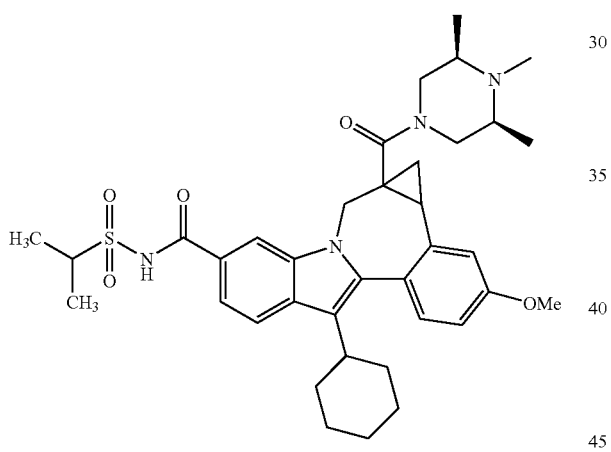

Cycloprop[d]indolo[2,1-a][2]benzazepine-5-carboxamide, 8-cyclohexyl-1,1a,2,12b-tetrahydro-11-methoxy-N-(2-propylsulfonyl)-1a-[[(3R,5S)-3,4,5-trimethyl-1-piperazinyl]carbonyl]-. Prepared as a member of a library using the following general procedure. The acid (0.055 mmol, 1 eq.) was dissolved in dried DMF and followed by adding HATU (0.083 mmol, 1.5 eq.) and DIPEA(0.083. 1.5 eq.). The solution was stirred for 2 minutes and added into pre-weighted amine (0.083 mmol, 1.5 eq.) at room temperature. The mixture was stirred 14 h and purified by prep-HPLC using the method described below. Homogeneous fractions were combined and evaporated to give 20.47 mg of the title compound. m/e 661.24 (M+H)$^+$, Rt=6.32 min, 96.7% purity. LCMS method: Start % B: 0, Final % B: 100; Gradient time: 2 min; Stop time: 4 min; Flow rate: 1 ml/min; wavelenth: 220 nm; Solvent A: 5% acetonitrile/95% water; Solvent B: 95% acetonitrile/5% water/10 mM ammonium acetate; Column: XBridge 2.1×50 mm 5 μm C18. 1H NMR (Flow) (600 MHz, CDCl$_3$-DMSO-$_{d6}$) δ 8.36 bs, 8.28 s, 8.16 s, 8.00 s, 7.85 (dd, J=~6 Hz), 7.69 (dd, J=~6 Hz), 7.31 (d, J=~6 Hz), 5.06 (bd, J=12 Hz), 4.87 (bd, J=~12 Hz), 4.11 (bd, J=~6 Hz), 3.95 (m), 3.92 (s), 3.64 (d, J=18 Hz), 2.96 (s) 2.80 (s), 2.60 (s), 2.56 (s), 2.31 (bs), 2.2-1.9 (m), 1.78 (bs), 1.65 (bd, J=~5 Hz), 1.54 (bd, J=18 Hz), 1.39 (d, J=24 Hz), 1.3-0.90 (m).

EXAMPLE 12

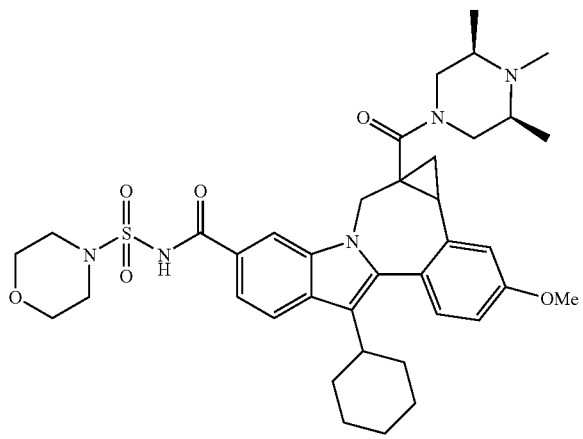

The TFA salt of the product (0.0323 g, 47%) was prepared from the acid using HBTU and triethylamine in dichloromethane. LCMS method: Start % B: 0, Final % B: 100; Gradient time: 3 min; Stop time: 4 min; Flow rate: 4 ml/min; Wavelenth: 220; Solvent A: 10% MeOH/90% H$_2$O/0.1% Trifluoroacetic Acid; Solvent B: 10% H2O/90% MeOH/0.1% Trifluoroacetic Acid; Column: XBridge 4.6×50 mm S5. LC-MS retention time: 3.023; MS m/z (M+H) 704.

We claim:
1. A compound of formula I

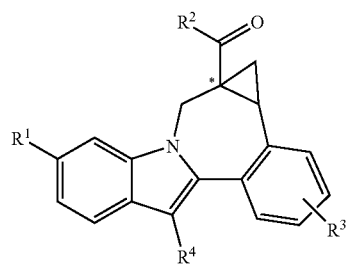

where:

$R^1$ is $CO_2R^5$ or $CONR^6R^7$;

$R^2$ is piperidinyl or piperazinyl and is substituted with 3 substituents selected from the group consisting of alkyl, haloalkyl, alkoxyalkyl, (phenyl)alkyl, alkylCO, haloalkylCO, alkoxyCO, (amino)CO, (alkylamino)CO, and (dialkylamino)CO;

$R^3$ is hydrogen, halo, alkyl, alkenyl, hydroxy, benzyloxy, or alkoxy;

$R^4$ is cycloalkyl;

$R^5$ is hydrogen or alkyl;

$R^6$ is hydrogen, alkyl, alkylSO$_2$, cycloalkylSO$_2$, haloalkylSO$_2$, $(R^7)(R^8)NSO_2$, or $(R^9)SO_2$;

$R^7$ is hydrogen or alkyl;

$R^8$ is hydrogen or alkyl;

$R^9$ is azetidinyl, pyrrolidinly, piperidinyl, N—($R^{10}$) piperazinyl, morpholinyl, thiomorpholinyl, homopiperidinyl, or homomorpholinyl;

$R^{10}$ is hydrogen or alkyl; and the carbon bearing the asterisk is of the (R) configuration or the (S) configuration;

or a pharmaceutically acceptable salt thereof.

2. A compound of claim 1 where $R^1$ is CONHR$^6$ and $R^6$ is alkylSO$_2$, cycloalkylSO$_2$, haloalkylSO$_2$, ($R^7$)($R^8$)NSO$_2$, or ($R^9$)SO$_2$.

3. A compound of claim 1 where $R^2$ is

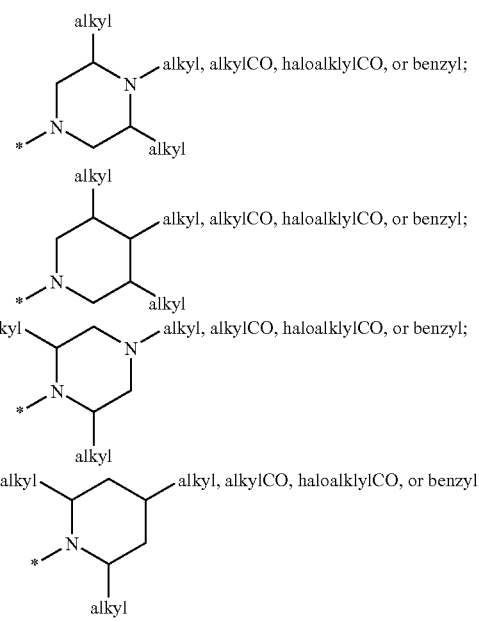

4. A compound of claim 1 where $R^3$ is hydrogen.
5. A compound of claim 1 where $R^3$ methoxy.
6. A compound of claim 1 where $R^4$ is cyclohexyl.
7. A compound of claim 1 where $R^6$ is alkylSO$_2$, ($R^7$)($R^8$)NSO$_2$, or ($R^9$)SO$_2$.
8. A compound of claim 1 where the carbon bearing the asterisk is of the (R) configuration.
9. A compound of claim 1 where the carbon bearing the asterisk is of the (S) configuration.
10. A compound of claim 1 selected from the group consisting of

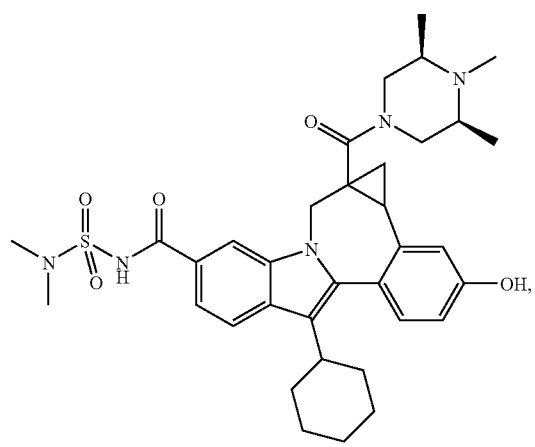

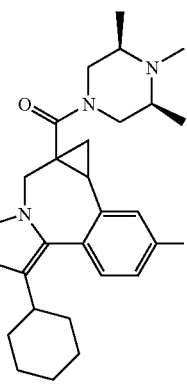

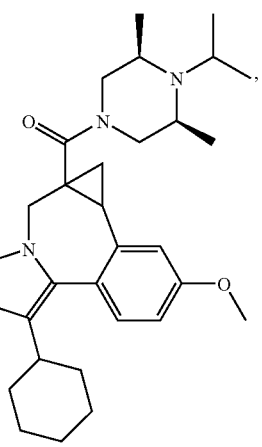

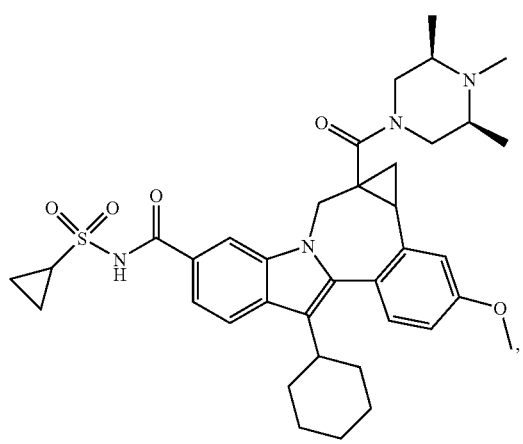

79
-continued
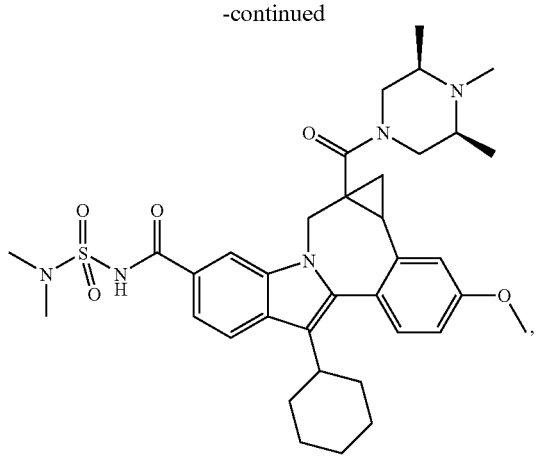
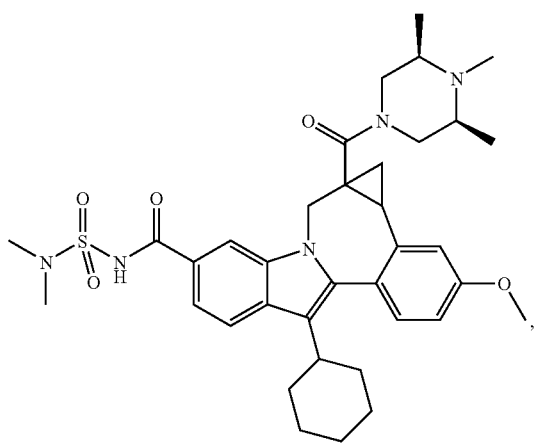
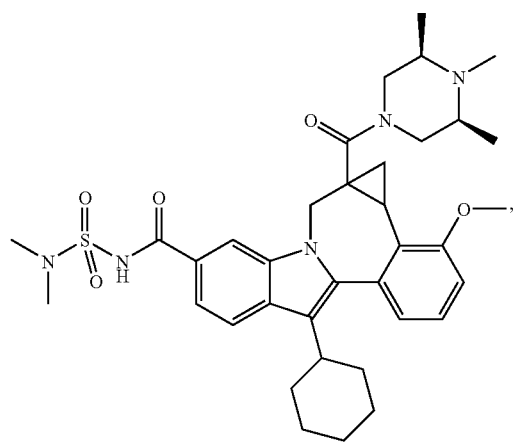
80
-continued
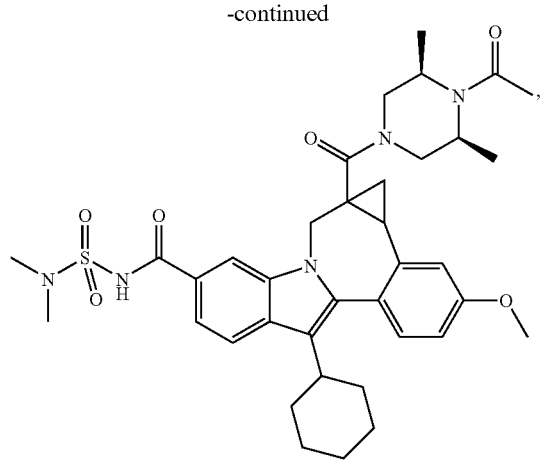
Chiral
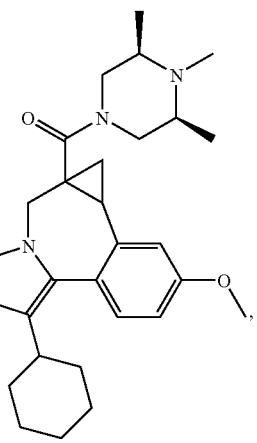

-continued

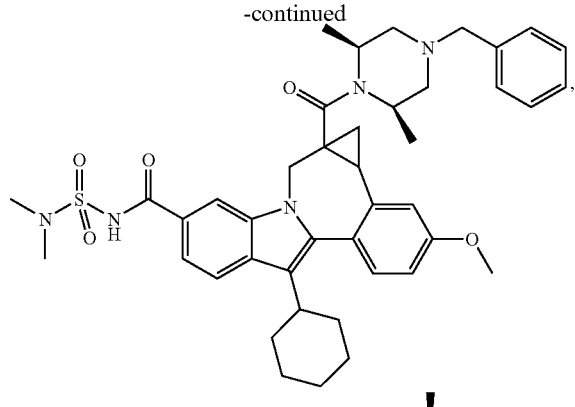

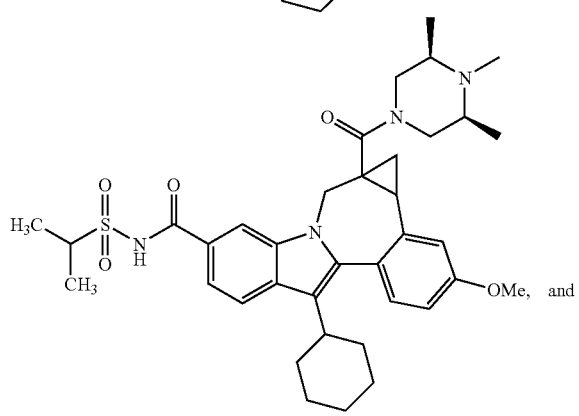

-continued

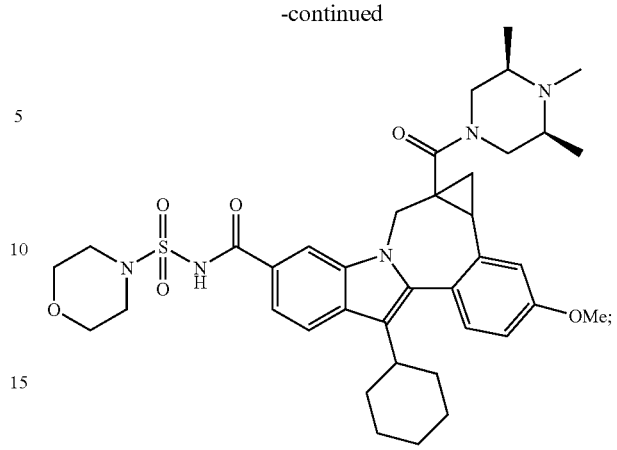

or a pharmaceutically acceptable salt thereof.

11. A composition comprising a compound of claim 1, or a pharmaceutically acceptable salt thereof, and a pharmaceutically acceptable carrier.

12. A method of treating hepatitis C infection comprising administering a therapeutically effective amount of a compound of claim 1, or a pharmaceutically acceptable salt thereof, to a patient.

* * * * *

UNITED STATES PATENT AND TRADEMARK OFFICE
CERTIFICATE OF CORRECTION

PATENT NO. : 7,521,441 B2
APPLICATION NO. : 11/745090
DATED : April 21, 2009
INVENTOR(S) : Robert G. Gentles et al.

It is certified that error appears in the above-identified patent and that said Letters Patent is hereby corrected as shown below:

Claim 1:
    Column 77, line 1, change "pyrrolidinly" to -- pyrrolidinyl --.

Claim 5:
    Column 77, line 40, after "$R_3$", insert -- is --.

Signed and Sealed this
Twenty-sixth Day of April, 2011

David J. Kappos
*Director of the United States Patent and Trademark Office*